(12) United States Patent
Wu et al.

(10) Patent No.: US 7,612,181 B2
(45) Date of Patent: Nov. 3, 2009

(54) DUAL VARIABLE DOMAIN IMMUNOGLOBULIN AND USES THEREOF

(75) Inventors: Chengbin Wu, Shrewsbury, MA (US); Tariq Ghayur, Holliston, MA (US); Richard W. Dixon, Jefferson, MA (US); Jochen G. Salfeld, North Grafton, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/507,050

(22) Filed: Aug. 18, 2006

(65) Prior Publication Data

US 2007/0071675 A1 Mar. 29, 2007

Related U.S. Application Data

(60) Provisional application No. 60/709,911, filed on Aug. 19, 2005, provisional application No. 60/732,892, filed on Nov. 2, 2005.

(51) Int. Cl.
*C12P 21/08* (2006.01)
*C07K 10/00* (2006.01)
*A61K 39/00* (2006.01)

(52) U.S. Cl. ............... 530/387.3; 530/388.1; 530/391.3; 530/391.7; 424/178.1; 424/181.1; 424/183.1

(58) Field of Classification Search ........................ None
See application file for complete search history.

(56) References Cited

U.S. PATENT DOCUMENTS

| | | | |
|---|---|---|---|
| 4,526,938 A | 7/1985 | Churchill et al. | |
| 4,699,784 A * | 10/1987 | Shih et al. ................ | 424/181.1 |
| 4,816,567 A | 3/1989 | Cabilly et al. | |
| 4,880,078 A | 11/1989 | Inoune et al. | |
| 4,943,533 A | 7/1990 | Mendelsohn et al. | |
| 4,946,778 A | 8/1990 | Ladner et al. | |
| 4,980,286 A | 12/1990 | Morgan et al. | |
| 5,128,326 A | 7/1992 | Balazs et al. | |
| 5,223,409 A | 6/1993 | Ladner et al. | |
| 5,225,539 A | 7/1993 | Winter | |
| 5,258,498 A | 11/1993 | Huston et al. | |
| 5,290,540 A | 3/1994 | Prince et al. | |
| 5,403,484 A | 4/1995 | Ladner et al. | |
| 5,427,908 A | 6/1995 | Dower et al. | |
| 5,500,362 A | 3/1996 | Robinson et al. | |
| 5,516,637 A | 5/1996 | Huang et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,571,698 A | 11/1996 | Ladner et al. | |
| 5,580,717 A | 12/1996 | Dower et al. | |
| 5,585,089 A | 12/1996 | Queen et al. | |
| 5,624,821 A | 4/1997 | Winter et al. | |
| 5,627,052 A | 5/1997 | Schrader et al. | |
| 5,641,870 A | 6/1997 | Rinderknecht et al. | |
| 5,648,260 A | 7/1997 | Winter et al. | |
| 5,658,727 A | 8/1997 | Barbas et al. | |
| 5,677,171 A | 10/1997 | Hudziak et al. | |
| 5,679,377 A | 10/1997 | Bernstein et al. | |
| 5,693,762 A | 12/1997 | Queen et al. | |
| 5,698,426 A | 12/1997 | Huse et al. | |
| 5,714,350 A | 2/1998 | Co et al. | |
| 5,714,352 A | 2/1998 | Jakobovits et al. | |
| 5,723,323 A | 3/1998 | Kauffman et al. | |
| 5,733,743 A | 3/1998 | Johnson et al. | |
| 5,736,137 A | 4/1998 | Anderson et al. | |
| 5,750,753 A | 5/1998 | Kimae et al. | |
| 5,766,886 A | 6/1998 | Studnicka et al. | |
| 5,780,225 A | 7/1998 | Wigler et al. | |
| 5,814,476 A | 9/1998 | Kauffman et al. | |
| 5,817,483 A | 10/1998 | Kauffman et al. | |
| 5,821,047 A | 10/1998 | Garrard et al. | |
| 5,824,514 A | 10/1998 | Kauffman et al. | |
| 5,855,913 A | 1/1999 | Hanes et al. | |
| 5,874,064 A | 2/1999 | Edwards et al. | |
| 5,891,996 A | 4/1999 | Mateo de Acosta del Rio et al. | |
| 5,912,015 A | 6/1999 | Bernstein et al. | |
| 5,916,597 A | 6/1999 | Lee et al. | |
| 5,916,771 A | 6/1999 | Hori et al. | |
| 5,934,272 A | 8/1999 | Lloyd et al. | |
| 5,939,598 A | 8/1999 | Kucherlapati et al. | |
| 5,969,108 A | 10/1999 | McCafferty et al. | |
| 5,976,862 A | 11/1999 | Kauffman et al. | |
| 5,985,309 A | 11/1999 | Edwards et al. | |
| 6,066,719 A | 5/2000 | Zapata | |
| 6,214,984 B1 | 4/2001 | Zapata | |
| 2002/0004587 A1 | 1/2002 | Miller et al. | |
| 2002/0127231 A1* | 9/2002 | Schneck et al. .......... | 424/178.1 |
| 2002/0136719 A1 | 9/2002 | Shenoy et al. | |

FOREIGN PATENT DOCUMENTS

| | | |
|---|---|---|
| WO | WO 90/02809 | 3/1990 |
| WO | WO 90/14424 | 11/1990 |

(Continued)

OTHER PUBLICATIONS

Li, Q., Carr, A.L., Donald, E.J., Skitzki, J.J., Okuyama, R., Stoolman, L.M., and Chang, A.E. Synergistic effects of IL-12 and IL-18 in skewing tumor-reactive T-cell responses towards a type I pattern. Cancer Research, 2005. vol. 65, pp. 1063-1070.*

(Continued)

*Primary Examiner*—David J. Blanchard
*Assistant Examiner*—Anne M. Gussow
(74) *Attorney, Agent, or Firm*—Tara Seshadri; Kenneth Zwicker; Yankwich & Associates, P.C.

(57) ABSTRACT

The present invention relates to engineered multivalent and multispecific binding proteins, methods of making, and specifically to their uses in the prevention and/or treatment of acute and chronic inflammatory and other diseases.

43 Claims, 1 Drawing Sheet

| | | |
|---|---|---|
| WO | WO 90/14430 | 11/1990 |
| WO | WO 90/14443 | 11/1990 |
| WO | WO 91/55548 | 5/1991 |
| WO | WO 91/09967 | 7/1991 |
| WO | WO 91/10737 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/03461 | 3/1992 |
| WO | WO 92/09690 | 6/1992 |
| WO | WO 92/11272 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/11236 | 6/1993 |
| WO | WO 94/02602 | 2/1994 |
| WO | WO 94/18219 | 8/1994 |
| WO | WO 95/15982 | 6/1995 |
| WO | WO 95/20045 | 7/1995 |
| WO | WO 95/20401 | 8/1995 |
| WO | WO 95/24918 | 11/1995 |
| WO | WO 96/20698 | 7/1996 |
| WO | WO 96/33735 | 10/1996 |
| WO | WO 96/34096 | 10/1996 |
| WO | WO 96/40210 | 12/1996 |
| WO | WO 97/20032 | 6/1997 |
| WO | WO 97/29131 | 8/1997 |
| WO | WO 97/32572 | 9/1997 |
| WO | WO 97/44013 | 11/1997 |
| WO | WO 98/16654 | 4/1998 |
| WO | WO 98/24893 | 6/1998 |
| WO | WO 98/31346 | 7/1998 |
| WO | WO 98/31700 | 7/1998 |
| WO | WO 98/50433 | 11/1998 |
| WO | WO 99/06834 | 2/1999 |
| WO | WO 99/15154 | 4/1999 |
| WO | WO 99/20253 | 4/1999 |
| WO | WO 99/23221 | 5/1999 |
| WO | WO 99/25044 | 5/1999 |
| WO | WO 99/45031 | 9/1999 |
| WO | WO 99/53049 | 10/1999 |
| WO | WO 99/54342 | 10/1999 |
| WO | WO 99/66903 | 12/1999 |
| WO | WO 00/09560 | 2/2000 |
| WO | WO 00/37504 | 6/2000 |
| WO | WO 00/56772 | 9/2000 |
| WO | WO 01/58956 | 8/2001 |
| WO | WO 01/62931 A2 | 8/2001 |
| WO | WO 01/77342 | 10/2001 |
| WO | WO 01/77342 A1 | 10/2001 |
| WO | WO 01/83525 A2 | 11/2001 |
| WO | WO 01/88138 A1 | 11/2001 |
| WO | WO 02/02773 | 1/2002 |
| WO | WO 02/072636 A2 | 9/2002 |
| WO | WO 02/097048 A2 | 12/2002 |
| WO | WO 03/016466 A2 | 2/2003 |
| WO | WO 03/035835 A2 | 5/2003 |
| WO | WO 2004/078140 A2 | 9/2004 |
| WO | WO 2005/100584 A2 | 10/2005 |

OTHER PUBLICATIONS

Margolin, A.L. and Navia, M.A. Protein crystals as novel catalytic materials. Angew. Chem. Int. Ed., 2001. vol. 40, pp. 2204-2222.*

Ames et al., Journal of Immunological Methods, (1995), "Conversion of murine Fabs isolated from a combinatorial phage display to full length immunoglobulins." 184: 177-186.

Aoki et al., Journal of the American College of Cardiology, (2005), "Endothelial Progenitor Cell Capture by Stents Coated With Antiobody Against CD34" 45(10): 1574-1579.

Arancio O. et al., EMBO Journal, (2004), "RAGE potentiates AB-induced perturbation of neurol function in transgenic mice" 23: 4096-4105.

Arndt, M. et al., Methods in Molecular Biology, (2003), "Bispecific Diabodies for Cancer Therapy" 207: 305-321.

Azzazy H. et al., Clinical Biochemistry, (2002), "Phage display technology: clinical applications and recent innovations" 35: 425-445.

Babcock, J.S. et al, Proc. Natl. Acad. Sci. USA, (1996), "A novel strategy for generating monoclonal antibodies from single, isolated lymphocytes producing antibodies of defined specificities" 93: 7843-7848.

Barbas, C.F. et al., Proc. Natl. Acad. Sci. USA, (1991), "Assembly of combinatorial antibody libraries on phage surfaces: The gene III site" 88: 7978-7982.

Barbas, C.F. et al., Proc. Natl. Acad. Sci. USA, (1994), "In vitro evolution of a neutralizing human antibody to human immunodeficiency virus type 1 to enhance affinity and broaden strain cross-reactivity" 91: 3809-3813.

Dickson, B.J. et al., Science, (2002), "Molecular Mechanisms of Axon Guidance" 298: 1959-1964.

Better et al. Science, (1988), "Secretion of an Active Chimeric Antibody Fragment" 240: 1041-1043.

Biewanga et al. Clinical Exp. Immunology, (1983), "IgA1 half moleculed in human multiple myeloma and the in vitro production of similar fragments from intact IgA1 molecules" 51: 395-400.

Bird et al. Science, (1988), "Single- Chain Antigen-Binding Proteins", 242: 423-426.

Bornemann KD et al., American Journal of pathology, (2001), "AB-Induced Inflammatory Processes in Microglia Cells of APP23 Transgenic Mice", 158(1): 63-73.

Boyce et al., Journal of Experimental Medicine, (2005), "No audible wheezing: nuggets and conundrums from mouse asthma models", 201(12): 1869-1873.

Brand DD., Comparative Medicine, (2005), "Rodent Models of Rheumatoid Arthritis", 55(2): 114-122.

Brennan, M. et al., Science, (1985), "Preparation of Bispecific Antibodies by Chemical Recombination of Monclonal Immunoglobulin G1 fragments", 229: 81-83.

Brinkman et al., Journal of immunological Methods, (1995), "Phage display of disulfide-stabilized FV Fragments", 182: 41-50.

Buchwald et al., Surgery, (1980), "Long-term, continuous IV heparin admin. By an implantable infusion pump in ambulatory pts w/ recurrent thrombosis", 88: 507-516.

Buras J.A. et al., Nat Rev. Drug. Discovery, (2005), "Animal models of sepsis: setting the stage", 4: 854-65.

Burke, Sandra E. et al., Advanced Drug Delivery Reviews, (2006), 58(3): 437-446.

Burton et al, Advances in Immunology, (1994), "Human Antibodies from Combinatorial Libraries", 57: 191-280.

CE Shepherd et al., Neuropathology and Applied Neurobiology, (2005), "Novel "inflammatory plaque" pathology in presenilin-1 Alzheimer's disease", 31: 503-511.

Calandra T, et al., Nature medicine, (2000), "Protection from septic shock by neutralization of macrophage migration inhibitory factor", 6(2): 164-170.

Carter et al., Proc. Natl. Acad. Sci. USA, (1992), "Humanization of an anti-p185 antibody for human cancer therapy" 89: 428-4289.

Chothia, C. et al., Journal of Molecular Biology, (1987), "Canonical Structures for the Hypervariable Regions of Immunolglobulins", 196: 901-917.

Chothia et al., Nature, (1989), "Conformations of immunoglobulin hypervariable regions", 342: 877-883.

Clackson et al., Letters to nature, (1991), "Making antibody fragments using phage display libraries", 352: 624-628.

Cleek et al., Pro Intl Symp. Control. Rel. Bioact. Mater., (1997), "Biodegradable Polymeric Carriers for a bFGF Antibody for Cardiovascular Application", 24: 853-854.

Co. M.S. et al., Mol. Immun., (1993), "Genetically Engineered Degylcosylation of the variable domain increases the affinity of an anti-CD33 monoclonal antibody", 30(15): 1361-1367.

Coffman et al., Journal of Experimental Medicine, (2005), "Nonhuman primate models of asthma", 201(12): 1875-1879.

Dall'Acqua et al., Biochemistry, (1998), "Contribution of domain interface residues to the stability of antibody CH3 domain homodimers", 37: 9266-9273.

D'Andrea, A. et al., Journal of Experimental Medicine, (1992), "Production of Natural Killer Cell Stimulatory Factor (Interleukin 12) by Peripheral Blood Mononuclear Cells", 17: 1387-1398.

Deane R, et al., Nature Medicine, (2003), "RAGE mediates amyloidB peptide transport across the blood-brain barrier and acculation in brain", 9(7): 907-913.

Descotes J., Develop. Biol. Standard., (1992), "Immunotoxicology of immunomodulators", 77: 99-102.

During et al., American Neuological Association, (1989), "Controlled Release of dopamine from a polymeric brain implant", 25. 351-356.

Dourcher et al., Nucleic Acids Research, (2002), "High-level and high-throughput recombinant protein production by transient transfection of suspension-growing human 293-EBNA1 cells" 30(2): 1-9.

Economides, A.N. et al., Nature Medicine, (2003), "Cytokine traps: multi-component, high-affinity blockers of cytokine action", 9(1): 47-52.

Eliezer Masliah, et al. Neuron (2005) "Effects of a-Synuclein Immunization in a Mouse Model of Parkinson's Disease", 46 857-868.

Felicia Yu Hsuan Teng, et al, Journal Neuroscience research, (2005), "Mini Review", 79: 273-278.

Finotto, et al., International immunology, (2005), "Asthmatic changes in mice lacking t-bet are mediated by il-13", 17(8): 993-1007.

Fuchs et al., Bio/Technology, (1991), "Targeting recombinant antibodies to the surface of *Escherichia coli*", 9: 1370-1372.

Gang, Xu et al., Journal of Neurochemistry, (2004), "Rapid communication", 91: 1018-1023.

Garrad et al., Bio/Technology, (1991), "Assembly and enrichment in a monovalent phage display system", 9: 1373-1377.

Gavilondo J.V. and Larrick J.W., BioTechniques, (2000), "Antibody Engineering at the Millennium", 29: 128-145.

Genain CP, et al., Journal of Molecular Medicine, (1997), "Creation of a model for multiple sclerosis in Callithrix jacchus marmosets", 75(3): 187-197.

Genovese Mc et al., NE Journal of medicine, (2005), "Abatacept for Rhematoid arthritis refractory to tumor necrosis factor", 353: 1114-1123.

Glennie, M.J. et al., Journal of immunology, (1987), "Preparation and performance of Bispecific F(aby) antibody containing thioether-linked fab fragments", 139(7): 2367-2376.

Goldspiel et al., Clinical Pharmacy, (1993), "Clinical Frontiers", 12: 488-505.

Gracie J.A. et al., Journal of Clinical investigation, (1999), "A proinflammatory role for IL-18 in rheumatoid arthritis", 104(10): 1393-1401.

Gram et al., PNAS, (1992), "In vitro selection and affinity maturation of antibodies from a naïve combinatorial imm. Library", 89: 3576-3580.

Green and Jakobovits, Journal of experimental medicine, "Regulation of B cell development by variable gene complexity in mice reconstituted with Human immunoglobulin yeast artificial chromosomes", (1998), 188(3): 483-495.

Green et al., Nature Genetics, (1994), "Antigen-specific human monoclonal antibodies from mice engineered w/ human Ig heavy and light chain" 7: 13-21.

Griffin et al., Journal of Immun., (2000), "Blockade of t cell activation using a surface-linked single-chain antibody to CTLA-4 (CD152)" 164: 4433.

Griffiths et al., EMBO journal, (1993), "Human anti-self antibodies w/ high specificity from phage display libraries" 12: 725-734.

Harriman G, Harper LK, Schiable TF., Ann Rhem Dis., "Summary of clinical trials in rheumatoid arthritis using infliximab, an anti-TNFa treatment", (1999), 58(1):I 61-64.

Hart et al., Journal of Allergy and Clinical Immunology, (2001), "Preclinical efficiency and safety of mepolizumab (SB-240563), a humanized monoclonal antibody to IL-5, in cynomolgus monkeys", 108(2): 250-257.

Hawkins et al., Journal of Molecular Biology, (1992), "Selection of Phage Antibodies by Binding Affinity Mimicking Affinity Maturation", 226: 889-896.

Hay et al., Human Antibody Hybridomas, (1992), "Bacteriphage cloning and *Escherichia coli* expression of a human IgM fab.", 3: 81-85.

Hidelbrand, H.F. et al., Surface and Coatings Technology, (2006), "Surface coatings for biological activation and functionalization of medical devices", 200(22-23): 6318-6324.

Holliger, p., and G. Winter, Cancer Immunol Immunother, (1997), "Diabodies: small bispecific antibody fragments", 45(3-4): 128-130.

Holliger, P., et al., PNAS USA, (1993), "Diabodies small bivalent and bispecific antibody fragments", 90: 6444-6448.

Hoogenboom et al. Nuc acid Res, (1991), "Multi-subunit proteins on the surface of filamentous phage: methodologies for displaying antibody (Fab) heavy and light chains", 19: 4133-4137.

Hoogenboom, H, and Chames P., Immunology Today, (2000), "Natural and designer binding sites" 21: 371-378.

Hoogenboom, H.R.TIB Tech, (1997), Designing and optimizing library selection strategies for generating high-affinity antibodies:, 15: 62-70.

Howard et al., Journal Neurosurgery, "Intracerebral drug delivery in rats with lesion induced memory deficits", 7(1): 105.

Huber et al., Nature (1976), "Crystallographic structure studies of an IgG molecule and an Fc fragment", 264, 415-420.

Huse et al., Science, (1989), "Generation of a Ig combinatorial library of Immunolglobulin Repertoire in Phage Lamda", 246: 1275-1281.

Huston, et al., PNAS USA, (1988), "Protein engineering of antibody binding sites", 85: 5879-5883.

Huston, et al., Methods in Enzymology, (1991), "Protein engineering of antibody binding sites: Recovery of specific activity in an anti-digoxin single-chain Fv analogue produced in *Escherichia coli*", 203: 46-88.

Hwang et al., Journal of Immunology, (2002), "Cutting Edge" 163: 633-637.

Igor Klyubin et al., Nature medicine, (2005), "letters" 11: 556-561.

Ito, A et al., Journal of immunology, (2003), "transfer of sever experimental autoimmune encephalomyelitis by il-12 and il-18 potentiated t cells is estrogen sensitive", 170(9): 4802-4809.

Jackson et al., Journal of immunology, (1995), "in vitro antibody maturation", 154(7): 3310-3319.

Johnsson B et al., Anal. Biochem, (1991), "Immobilization of proteins to a caroxymethyldextran modified gold surface for biospecific interaction analysis in surface plasmon resonance sensors" 198: 268-277.

Johnsson B et al., Journal of Molecular Recognition, (1995), "Comparison of methods for Immobilization to carboxymethyl dextran sensor surfaces", 8: 125-131.

Joliot et al., PNAS USA, (1991), "Antennapedia homeobox peptide regulates neural morphgenesis" 88: 1864-1868.

Jones et al., Nature, (1986), "Letters to Nature" 321: 522-525.

Jonsson, U et al., Biotechniques BioFeature, (1991), "Immobilization of Proteins to a Carboxymethyldextran-Modified gold surface for biospecific interaction anaylsis in surface plasmon resonance sensors", 11: 620-627.

Jonsson, U et al., Ann. Biol. Clin., (1993), "Advances in Clinical Biology", 51: 19-26.

Joosten, L.A. et al., Arthritis Rheum, (1996), "A comparative study" 39(5): 797-809.

Jungbluth et al., PNAS, (2003), "Medical Sciences" 100(2): 634-644.

Kabat et al., Ann. NY Acad. Sci., (1971), Attempts to locate complementary determining residues in the variable positions of light and heavy chains, 190: 382-391.

Karni, A., et al., Journal of Neuroimmunology, (2002), "IL-18linked to raise INF-y in multiple sclerosis", 125(1-2): 134-140.

Kellerman S-A. and Green L.L., Current Opinion in Biotechnology, (2002), "Antibody discovery", 13: 593-597.

Kettleborough et al., Protein Eng., (1991), "Humanization of a mouse monoclonal antibody by CDR-grafting: the importance of framework residues on loop conformation", 4(7): 773-783.

Kettleborough et al., Eur. Journal of Immunol., (1994), "Isolation of tumor cell-specific single-chain Fv from immunized mice", 24: 952-958.

Kim et al., Eur. Journal of Immunol.. (1994), "Identifying amino acid residues that influence plasma clearance of murine IgG1 fragments by site-directed mutagenesis", 24: 542-548.

Kipriyanov, S.M., et al., Int. Journal of Cancer, (1998), "Bispecific CD3XCD19 diabody for t cell-mediated lysis of malignant human b cells", 77(5): 763-772.

Konishi, K. et al., journal of immunol. Methods, (1997), "A simple and sensitive bioassay for the detection of human interleukin-18/ interferon-y-inducing factor using human myelomonocytic KG-1 cells", 209(2): 187-91.

Kostelny, S.A. M.S. Cole, and JY Tso, Journal of Immunology, (1992), "Formation of a biospecific antibody by the use of leucine zippers", 148(5): 1547-1553.

Kriangham, J. et al., Biomol Eng, (2001), "Bispecific and Bifunctional single chain recombinant antibodies", 18(2): 31-40.

Lam et al., Proceed. Int'l Symp. Control Rel. Bioact. Mater., (1997), "Microencapsulation of recombinant monoclonal antibody for local delivery", 24: 759-760.

Langer, Science, (1990), "New Methods of Drug Delivery" 249: 1527-1533.

Le Gall, F., et al., FEBS letters, (1999), "Di-, tri- and tetrameric single chain Fv antibody fragments against human CD19: effect of valency on cell binding", 453(1-2): 164-168.

Le Gall, F., et al., Journal of Immunological methods, (2004), "Immunosuppresive properties of anti-CD3 single-chain Fv and diabody", 285(1).

Leung, BP et al., Journal of immunol., (2000), "Combined effects of Il-12 and Il-18 on the induction of Collagen-Induced Arthritis", 164(12): 6495-6502.

Levy et al., Science, (1985), "Inhibition of Calcification of Bioprosthetic Heart valves by local controlled- release diphosphonate", 228: 190-192.

Little M. et al., Immunology Today, (2000), "Of mice and men: hybridoma and recombinant antibodies", 21: 364-370.

Lloyd, Clare M et al., Advances in Immunology, (2001), "Mouse Models of Allergic Airway Disease", 7:7 263-295.

Lu D., et al., Journal of Biological Chemistry, (2004), "Simultaneous blockade of both the epidermal growth factor receptor and the insulin like growth factor receptor signaling pathways in cancer cells with a fully human recombinant bispecific antibody", 279(4): 2856-2865.

Lublin, FD et al., Springer Semin Immunopathol., (1985), "Relapsing experimental allergic encephalomyelitis and autoimmune model of multiple sclerosis", 8(3): 197-208.

Luster et al., Toxicology, (1994), "Use of animal studies in risk assessment for immunotoxicology", 92(1-3): 229-243.

MacCullum, Journal of Mol. Biol., (1996), "Antibody-antigen Interactions: Contact analysis and binding site topography", 262(5): 7332-745.

Mack M et al., PNAS USA, (1995), "A small biospecific antibody construct expressed as a functional single-chain molecule w/ high tumor cell cytotoxicity", 92(15): 7021-7025.

Marchalonis et al., Adv. Exp. Med. Biol., (2001), "Evolutionary factors in the emergence of the combinatorial germline antibody repertoire", 484: 13-30.

Marco Domeniconi, et al., Journal of Neurological Science, (2005), "Overcoming inhibitors in myelin to promote axonal regeneration", 233: 43-47.

Marks et al., BioTechnology (1992), 10: 779-783, "By-passing immunization building high affinity human antibodies by chain shuffling".

Marques, AP et al., Biodegradable Systems in tissue Engineering and Regenerative medicine (2005) 377-397 "Mediation of the cytokine network in the implantation of orthopedic devices".

Mateo et al., (1997) Immunotechnology. "Humanization of a mouse monoclonal antibody that blocks the epidermal growth factor receptor", 3(1): 71-81.

Mccafferty et al., Letters to Nature (1990) "Phage antibodies", 348: 552-554.

McDonnell, et al., Progress in Respiratory Research (2001) 31: "New drugs for Asthma, allergy and COPD", 247-250.

McGee, AW et al., Trends Neuroscience (2003) "The Nogo-66 receptor", 26: 193-198.

McIntosh JK. Et al., Journal of Immunol. (1989), 143(1): 162-167, "In vivo induction of the Il-6 by administration of exogenous cytokines and detection of de novo serum levels of IL-6 in tumor-bearing mice".

Mendez et al., Nature genetics (1997) "Functional transplant of megabase human Immunoglobulin loci recapitulates human antibody response in mice", 15: 146-156.

Merchant AM et al., Nature Biotechnology (1998), 16(7): 677-681, "An efficient route to human bispecific IgG".

Michelle C Janelsins, et al., Journal of Neuroinflammation(2005) "Open access", 2: 1-12.

Milan Makwanal, et al., FEBS Journal (2005), "Molecular mechanisms in successful peripheral regeneration" 272: 2628-2638.

Miller, K et al., Journal of Immunol. (2003), 170(9): 4854-4861, "Design, Construction, and In vitro analyses of multivalent".

Milstein, C. and A.C. Cuello, Nature, (1983) 305(5934): p. 537-40; "Hybrid hybridomas and their use in immunohistochemistry".

Mizushima, S. and Nagata, S., Nucleic acids Research (1990), 18:17, "A powerful mammalian expression vector".

Modjtahedi et al, Br J Cancer, (1996), 73(2): 228-35; "Phase 1 trial and tumor localisation of the anti-EGFR monoclonal antibody ICR62 in head and neck or lung cancer".

Modjtahedi et al, 2003, Int J Cancer, 105(2): 273-80, "Targeting of cells expressing wild-type EGFR and type-III mutant EGFR".

Modjtahedi et al., 1993, Br J Cancer. 67(2): 247-53;"The human EGF receptor as a target for cancer therapy: six new rat mAbs against the receptor on the breast carcinoma".

Modjtahedi et al., 1993, J. Cell Biophys. 22(1-3): 129-46, "Antitumor Activity of Combinations of Antibodies Directed Against Different Epitopes on the extracellular domain of the human EGF receptor".

Morgan and Anderson et al., (1993), Ann. Rev. Biochem. 62:191-217; "Human gene therapy".

Mulligan et al., Science 260:926-932 (1993); "The basic science of gene therapy".

Mullinax et al., BioTechniques 12(6): 864-869 (1992); "Expression of a heterodimeric fab antibody protein in one cloning step".

Murthy et al., (1987), Arch Biochem Biophys. 252(2): 549-60; "Binding of an antagonistic monoclonal antibody to an intact and fragmented EGF receptor polypeptide".

Nakanishi, K. et al.,. Annu Rev Immunol, (2001),19: 423-74; "Interleukin-18 regulates both TH1 and TH2 responses".

Nelson RB et al., Curr Pharm Des. (2005), 11: 3335; "The Dualistic nature of immune modulation in alzheimers disease".

Ning et al. , (1996), Radiotherapy &Oncology 39:179-189; "Intratumoral radioimmunotherapy of a human colon cancer xenograft using a sustained release gel".

Okamoto H. and Kamatani N. et al., (2004), N Engl J Med. 351:1909; "Rituximab for Rheumatoid arthritis".

Owens T. et al., (1995) Neurol Clin.13(1):51-73; "The immunology of MS and its animal model".

Padilla et al., Journal of Immunology (2005), 174(12): 8097-8105; "Regulates the immune response to inhales antigens".

Padlan et al., FASEB J. 9:133-139 (1995); "Indentification of specifity determining residues in antibodies".

Padlan et al., Molecular Immunology, 28(4/5): 489-498 (1991); "A possible procedure for reducing the immungenicty of antibody variable domains while preserving their ligand-binding properties".

Peipp, M. and T. Valerius et al., Biochem Soc Trans, (2002) 30(4): p. 507-11; "Bispecifc antibodies targeting cancer cells".

Peng SL et al., Methods Mol Med.(2004), 102: 227-72; "Experimental use of murine lupus models".

Persic et al., Gene 187 9-18 (1997); "An integrated vestor system for the eukaryotic expression of antibodies or their fragments after selection from phage display libraries".

Pluckthun, A. and P. Pack et al., Immunotechnology, (1997). 3(2): 83-105; "New protein engineering approaches to multivalent and bispecific antibody fragments".

Poljak, R.J., et al. (1994), Structure 2:1121-1123; "Production and Structure of diabodies".
Presta et al., J. Immunol. 151:2623 (1993), "Humanization of an Antibody directed against IgE".
Presta LG et al., (2005) J Allergy Clin Immunol. 116:731-6; "Selection, design and engineering of therapeutic antibodies".
R. Jefferis et al., Biotechnol. Prog.(2005), 21: 11-16; "Glycosylation of Recombinant antibody therapeutics".
R.J. Kaufman and P.A. Sharp et al., Mol. Biol. (1982), 159:601-621; "Amplification and expression of sequences cotransfected with a modular dihydrofolate reductase complementary DNA gene".
R. Langer and Peppas et al., (1983), J., Macromol. Sci. Rev. Macromol. Chem. 23:61; "Chemical and Physical structure of polymers as carriers for controlled release of bioactive agents".
Ridgway, J.B., et al., Protein Eng, (1996), 9(7): 617-21; "Knobs-into-holes engineering of antibody CH3 domains for heavy chain heterdimerzation".
Riechmann et al., Nature 332:323 (1988); "Reshaping human antibodies for therapy".
Roberts, R.W. and Szostak, J.W. et al., (1997), Proc. Natl. Acad. Sci. USA 94:12297-12302; "RNA peptide fusions for the in vitro selection of pepides and proteins".
Rodeck et al., (1987), J Cell Biochem. 35(4):315-20; "Interactions between growth factor receptors and corresponding monoclonal antibodies in human tumors".
Roguska et al., PNAS 91:969-973 (1994); "Humanization of murine monoclonal antibodies through variable domain resurfacing".
Saudek et al., (1989), N. Engl. J. Med. 321:574; "A preliminary trial of the programmable implantatable medication system for insulin delivery".
Sawai et al., AJRI 34:26-34 (1995); Direct production of Fab fragment derived from the sperm immobilizing antibody using polymerase chain reaction and cDNA expression vectors.
Schier et al. Gene 169:147-155 (1995); "Identification of functional and structural amino-acid residues by parsimonious mutagenesis".
Sefton et al., (1987), CRC Crit. Ref. Biomed. Eng. 14:20 "Implantable pumps".
Seligman et al., (1978) Ann Immunol 129: 855-70; "Immunochemical study".
Sfikakis PP et al., (2005), Curr Opin Rheumatol 17:550-7; "Lessons from lupus animal models".
Shapiro et al., Crit. Rev. Immunol. 22(3): 183-200 (2002); "DNA target motifs of somatic mutagenesis in antibody genes".
Shields, R. L. et al., J. Biol. Chem. (2002), 277:26733-26740; "Lack of fucose on human IgG1".
Shu et al., PNAS 90:7995-7999 (1993); "Secretion of a single-gene-encoded immunoglobulin from myeloma cells".
Sims et al., J. Immunol. 151: 2296 (1993); "A humanized CD18 antibody can block function without without cell destruction".
Skerra et al., Science 240:1038-1040 (1988); "Assembly of a functional immunoglobulin Fv fragment in *Escherichia coli*".
Snibson K J et al., Journal of the British Society for Allergy and Clinical Immunology (2005), 35(2), 146-52; "Airway remodeling and inflammation in sheep lungs after chronic airway challenge with house dust mite".
Soloman B. et al., Curr Alzheimer Res. (2004), 1:149; "Alzheimer's disease and immunotherapy".
Song et al., (1995), PDA Journal of Pharmaceutical Science &Technology 50:372-397; (Antibody mediated lung targeting of long-circulating emulsions).
Staerz, U.D., et al., Nature, (1985). 314(6012): p. 628-31; "Hybrid antibodies can target sites for attack by T-cells".
Steinman L, et al., (2005) Trends Immunol. 26(11):565-71; "Virtues and pitfalls of EAE the development of therapies for MS".
Studnicka et al., Protein Engineering (1994) 7(6): 805-814, "Human-engineering monoclonal antibodies retain full specific binding activity by perserving non-CDR complenmentarity modulating residues".
Hart BA, et al., (2005) J Immunol 175(7):4761-8; "Supression of ongoing disease in a non-human primate model of MS by a human anti human IL-12p40 antibody".
Tara Karnezis, et al., Nature Neuroscience (2004), 7: 736; "The neurite outgrowth inhibitor Nogo A is involved in autoimmune mediated demyelination".

Taylor, L. D., et al., Nucl. Acids Res.(1992), 20:6287-6295; "A transgenic mouse that expresses a diversity of human sequence heavy and light chain immunoglobulins".
Tolstoshev et al., (1993), Ann. Rev. Pharmacol. Toxicol. 32:573-596; "Gene therapy concepts current trials and future directions".
Tuohy VK, et al., (1999) J Exp Med. 189(7):1033-42, "Spontaneous regression of primary autoreactivity during chronic progression of experimental autoimmune encephalomyelitis and MS".
Umana et al., (1999) Nat. Biotech. 17:176-1; "Engineered glycoforma of an autoineuroblastoma IgG1 with optimized antibody dependent cellular cytotoxic activity".
Urlaub and Chasin, (1980) Proc. Natl. Acad. Sci. USA , 77:4216-4220, "Isolation of chinese hamster cell mutants deficient in dihydrofolate reductase activity".
Verhoeyen et al., Science 239:1534 (1988); "Reshaping human antibodies grafting an antilysozyme activity".
Von Mehren M. et al., Annu Rev Med. (2003), 54:343-69; "Monoclonal antibody therapy for cancer".
Wallick, S.C., et al., Exp. Med. (1988), 168:1099-1109; "Glycosylation of a Vh residue of a monoclonal antibody against dextran increases its affinity for antigen".
Ward et al., (1989) Nature 341:544-546; "Binding activites of a repertoire of single immunoglobulin variable domains secreted from *Escherichia coli*".
West et al., Biochemistry, (2000), "Crystal structure and immunglobulin G Binding Properties of the human major histocompatibilty complex related fc receptor", 39: 9698-708.
William L. Klein, Neurochem Int., (2002), "AB toxicity in alzheimers disease globular oligomers as new vaccine and durg targets", 41:345.
Wright, A., et al., EMBO J., (1991), "Antibody variable region glycosylation position effects on antigen binding and carbohydrate structure", 10:2717 2723.
Wu and Wu et al., Biotherapy (1987), "Delivery sytems for gene therapy", 3:87-95.
Wu and Wuet al., J. Biol. Chem. (1987), "Receptor mediated in vitro gene transformation by a soluble DNA carrier system", 262:4429-4432.
Wu, A.M. et al., Immunotechnology, (1996), "Tumor localization of anti-CEA single-chain Fvs: improved targeting by non-covalent dimers", 2(1): 21-36.
Wu, A.M. et al., Immunotechnology (1996), "Tumor localization of anti-CEA single-chain Fvs: improved targeting by non-covalent dimers", 2(1): 21-36.
Wu, Peng; Grainger, David W. et al, Biomaterials, (2006), "Drug/device combinations for local drug therapies and infection prophylaxis", 27(11): 2450-2467.
Yelton et al., J. Immunol., (1995); "Affinity maturation of the BR96 Anti-Carcinoma antibody by codon based mutagenesis", 155:1994-2004.
Zapata et al., Protein Eng., (1995), "Engineering linear fragments for efficient production in *Escherichia coli*anf enhanced antiproliferative activity", 8(10):1057-1062.
Thies et al., J. Mol. Biol., (1999), "Folding and Association of the Antibody Domain CH3: Prolyl Isomerization Preceeds Dimerization", 293: 67-79.
Alderson et al., International Immunology, 6(11): 1799-1806 (1994).
Alt et al., FEBS Letters, 454: 90-94 (1999).
Coloma et al., *Nature Biotechnology* vol. 15, 159-163 (1996).
Hanasaki et al., The Journal of Biological Chemistry, 270(13): 7543-7550 (1995).
Hoogenboom, H. R., *Nature Biotechnology* vol. 15, 126 (1997).
Plückthun et al., Immunotechnology, 3: 83-105 (1997).
Santos et al., Clinical Cancer Research, 5: 3118s-3123s (1999).
Wu et al., Nature Biotechnology (Advance Online Publication), 2007 Nature Publishing Group, 1-8, http://www.nature.com/naturebiotechnology.
Yonehara et al., International Immunology, 6(12): T849-1856 (1994).
Presta, *Current Opinion in Immunology*, 20: 460-470 (2008).
Morrison, *Nature Biotech.*, 25(11): 1233-1234 (2007).
International Search Report, Aug. 18, 2008, for international application No. PCT/US06/032398.

Written Opinion, Aug. 18, 2008, for international application No. PCT/US06/032398.

Alt et al., *FEBS Lett.*, 454(1-2): 90-94 (1999).

Li et al., *Protein Engineering*, 12(9): 787-796 (1999).

Kuby, *Immunology, 2nd ed.*, (W. H. Freeman and Company, New York, 1994) (ISBN 0-7167-2643-2) Fig. 5-6, p. 115.

Bäckström et al., "Signaling Efficiency of the T Cell Receptor Controlled by a Single Amino Acid in the β Chain Constant Region," *J. Exp. Med.*, 186 (11): 1933-1938 (1997).

Brüsselbach et al., "Enzyme recruitment and tumor cell killing in vitro by a secreted bispecific single-chain diabody," *Tumor Targeting*, 4: 115-123 (1999).

Li et al., "Structural mutations in the constant region of the T-cell antigen receptor (TCR)β chain and their effect on TCRα and β chain interaction," *Immunol.*, 88: 524-530 (1996).

Lu et al., "Di-diabody: a novel tetravalent bispecific antibody molecule by design," *J. Immunol. Methods*, 279: 219-232 (2003).

Lu et al., "A Fully Human Recombinant IgG-like Bispecific Antibody to Both the Epidermal Growth Factor Receptor and the Insulin-like Growth Factor Receptor for Enhanced Antitumor Activity," *J. Biol. Chem.*, 280 (20): 19665-19672 (2005).

Wileman et al., "Association between Subunit Ectodomains Promote T Cell Antigen Receptor Assembly and Protect against Degradation in the ER," *J. Cell Biol.*, 122 (1): 67-78 (1993).

Taiwan Patent Office Search Report for Taiwanese patent application No. 095130565.

Kontermann, "Recombinant bispecific antibodies for cancer therapy," *Acta Pharmacologica Sinica*, 26(1): 1-9 (Jan. 2005).

Marvin et al., "Recombinant approaches to IgG-like bispecific antibodies," *Acta Pharmacologica Sinica*, 26(6): 649-658 (Jun. 2005).

\* cited by examiner

DUAL VARIABLE DOMAIN IMMUNOGLOBULIN AND USES THEREOF

CROSS-REFERENCE TO RELATED APPLICATION

This application claims the benefit of priority to U.S. provisional application No. 60/709,911 filed Aug. 19, 2005, and to U.S. provisional application No. 60/732,892 filed Nov. 2, 2005.

FIELD OF THE INVENTION

The present invention relates to multivalent and multispecific binding proteins, methods of making, and specifically to their uses in the prevention and/or treatment of acute and chronic inflammatory, cancer, and other diseases.

BACKGROUND OF THE INVENTION

Engineered proteins, such as multispecific antibodies capable of binding two or more antigens are known in the art. Such multispecific binding proteins can be generated using cell fusion, chemical conjugation, or recombinant DNA techniques.

Bispecific antibodies have been produced using the quadroma technology (see Milstein, C. and A. C. Cuello, Nature, 1983. 305(5934): p. 537-40) based on the somatic fusion of two different hybridoma cell lines expressing murine monoclonal antibodies with the desired specificities of the bispecific antibody. Because of the random pairing of two different Ig heavy and light chains within the resulting hybrid-hybridoma (or quadroma) cell line, up to ten different immunogloblin species are generated of which only one is the functional bispecific antibody. The presence of mispaired by-products, and significantly reduced production yields, means sophisticated purification procedures are required.

Bispecific antibodies can be produced by chemical conjugation of two different mAbs (see Staerz, U. D., et al., Nature, 1985. 314(6012): p. 628-31). This approach does not yield homogeneous preparation. Other approaches have used chemical conjugation of two different monoclonal antibodies or smaller antibody fragments (see Brennan, M., et al., Science, 1985. 229(4708): p. 81-3). Another method is the coupling of two parental antibodies with a hetero-bifunctional crosslinker, but the resulting preparations of bispecific antibodies suffer from significant molecular heterogeneity because reaction of the crosslinker with the parental antibodies is not site-directed. To obtain more homogeneous preparations of bispecific antibodies two different Fab fragments have been chemically crosslinked at their hinge cysteine residues in a site-directed manner (see Glennie, M. J., et al., J Immunol, 1987. 139(7): p. 2367-75). But this method results in Fab'2 fragments, not full IgG molecule.

A wide variety of other recombinant bispecific antibody formats have been developed in the recent past (see Kriangkum, J., et al., Biomol Eng, 2001. 18(2): p. 3140). Amongst them tandem single-chain Fv molecules and diabodies, and various derivatives there of, are the most widely used formats for the construction of recombinant bispecific antibodies. Routinely, construction of these molecules starts from two single-chain Fv (scFv) fragments that recognize different antigens (see Economides, A. N., et al., Nat Med, 2003. 9(1): p. 47-52). Tandem scFv molecules (taFv) represent a straightforward format simply connecting the two scFv molecules with an additional peptide linker. The two scFv fragments present in these tandem scFv molecules form separate folding entities. Various linkers can be used to connect the two scFv fragments and linkers with a length of up to 63 residues (see Nakanishi, K., et al., Annu Rev Immunol, 2001. 19: p. 423-74). Although the parental scFv fragments can normally be expressed in soluble form in bacteria, it is, however, often observed that tandem scFv molecules form insoluble aggregates in bacteria. Hence, refolding protocols or the use of mammalian expression systems are routinely applied to produce soluble tandem scFv molecules. In a recent study, in vivo expression by transgenic rabbits and cattle of a tandem scFv directed against CD28 and a melanoma-associated proteoglycan was reported (see Gracie, J. A., et al., J Clin Invest, 1999. 104(10): p. 1393-401). In this construct, the two scFv molecules were connected by a CH1 linker and serum concentrations of up to 100 mg/L of the bispecific antibody were found. Various strategies including variations of the domain order or using middle linkers with varying length or flexibility were employed to allow soluble expression in bacteria. A few studies have now reported expression of soluble tandem scFv molecules in bacteria (see Leung, B. P., et al., J Immunol, 2000. 164(12): p. 6495-502; Ito, A., et al., J Immunol, 2003. 170(9): p. 4802-9; Karni, A., et al., J Neuroimmunol, 2002. 125(1-2): p. 134-40) using either a very short Ala3 linker or long glycine/serine-rich linkers. In a recent study, phage display of a tandem scFv repertoire containing randomized middle linkers with a length of 3 or 6 residues was employed to enrich for those molecules that are produced in soluble and active form in bacteria. This approach resulted in the isolation of a preferred tandem scFv molecule with a 6 amino acid residue linker (see Arndt, M. and J. Krauss, Methods Mol Biol, 2003. 207: p. 305-21). It is unclear whether this linker sequence represents a general solution to the soluble expression of tandem scFv molecules. Nevertheless, this study demonstrated that phage display of tandem scFv molecules in combination with directed mutagenesis is a powerful tool to enrich for these molecules, which can be expressed in bacteria in an active form.

Bispecific diabodies (Db) utilize the diabody format for expression. Diabodies are produced from scFv fragments by reducing the length of the linker connecting the VH and VL domain to approximately 5 residues (see Peipp, M. and T. Valerius, Biochem Soc Trans, 2002. 30(4): p. 507-11). This reduction of linker size facilitates dimerization of two polypeptide chains by crossover pairing of the VH and VL domains. Bispecific diabodies are produced by expressing, two polypeptide chains with, either the structure VHA-VLB and VHB-VLA (VH-VL configuration), or VLA-VHB and VLB-VHA (VL-VH configuration) within the same cell. A large variety of different bispecific diabodies have been produced in the past and most of them cab be expressed in soluble form in bacteria. However, a recent comparative study demonstrates that the orientation of the variable domains can influence expression and formation of active binding sites (see Mack, M., G. Riethmuller, and P. Kufer, Proc Natl Acad Sci USA, 1995. 92(15): p. 7021-5). Nevertheless, soluble expression in bacteria represents an important advantage over tandem scFv molecules. However, since two different polypeptide chains are expressed within a single cell inactive homodimers can be produced together with active heterodimers. This necessitates the implementation of additional purification steps in order to obtain homogenous preparations of bispecific diabodies. One approach to force the generation of bispecific diabodies is the production of knob-into-hole diabodies (see Holliger, P., T. Prospero, and G. Winter, Proc Natl Acad Sci USA, 1993. 90(14): p. 6444-8.18). This was demonstrated for a bispecific diabody directed against HER2 and CD3. A large knob was introduced in the VH domain by exchanging Val37 with Phe and Leu45 with Trp and a complementary hole was produced in the VL domain by mutating Phe98 to Met and Tyr87 to Ala, either in the anti-HER2 or the anti-CD3 variable domains. By using this approach the production of bispecific diabodies could be increased from 72% by the parental diabody to over 90% by the knob-into-hole diabody. Importantly, production yields did only slightly decrease as a result of these mutations. However, a reduction in antigen-binding activity was observed for several analyzed constructs. Thus, this rather elaborate approach requires the analysis of various constructs in order to identify those mutations that produce heterodimeric molecule with unaltered binding activity. In addition, such approach requires mutational modification of the immunoglobulin sequence at the constant region, thus creating non-native and non-natural form of the antibody sequence, which may result in increased immunogenicity, poor in vivo stability, as well as undesirable pharmacokinetics.

Single-chain diabodies (scDb) represent an alternative strategy to improve the formation of bispecific diabody-like molecules (see Holliger, P. and G. Winter, Cancer Immunol Immunother, 1997. 45(3-4): p. 128-30; Wu, A. M., et al., Immunotechnology, 1996. 2(1): p. 21-36). Bispecific single-chain diabodies are produced by connecting the two diabody-forming polypeptide chains with an additional middle linker with a length of approximately 15 amino acid residues. Consequently, all molecules with a molecular weight corresponding to monomeric single-chain diabodies (50-60 kDa) are bispecific. Several studies have demonstrated that bispecific single chain diabodies are expressed in bacteria in soluble and active form with the majority of purified molecules present as monomers (see Holliger, P. and G. Winter, Cancer Immunol Immunother, 1997. 45(34): p. 128-30; Wu, A. M., et al., Immunotechnology, 1996. 2(1): p. 21-36; Pluckthun, A. and P. Pack, Immunotechnology, 1997. 3(2): p. 83-105; Ridgway, J. B., et al., Protein Eng, 1996. 9(7): p. 617-21). Thus, single-chain diabodies combine the advantages of tandem scFvs (all monomers are bispecific) and diabodies (soluble expression in bacteria).

More recently diabody have been fused to Fc to generate more Ig-like molecules, named di-diabody (see Lu, D., et al., J Biol Chem, 2004. 279(4): p. 2856-65). In addition, multivalent antibody construct comprising two Fab repeats in the heavy chain of an IgG and capable of binding four antigen molecules has been described (see WO 0177342A1, and Miller, K., et al., J Immunol, 2003. 170(9): p. 4854-61).

There is a need in the art for improved multivalent binding proteins capable of binding two or more antigens. The present invention provides a novel family of binding proteins capable of binding two or more antigens with high affinity.

SUMMARY OF THE INVENTION

This invention pertains to multivalent binding proteins capable of binding two or more antigens. The present invention provides a novel family of binding proteins capable of binding two or more antigens with high affinity.

In one embodiment the invention provides a binding protein comprising a polypeptide chain, wherein said polypeptide chain comprises VD1-(X1)n-VD2-C-(X2)n, wherein VD1 is a first variable domain, VD2 is a second variable domain, C is a constant domain, X1 represents an amino acid or polypeptide, X2 represents an Fc region and n is 0 or 1. In a preferred embodiment the VD1 and VD2 in the binding protein are heavy chain variable domains. More preferably the heavy chain variable domain is selected from the group consisting of a murine heavy chain variable domain, a human heavy chain variable domain, a CDR grafted heavy chain variable domain, and a humanized heavy chain variable domain. In a preferred embodiment VD1 and VD2 are capable of binding the same antigen. In another embodiment VD1 and VD2 are capable of binding different antigens. Preferably C is a heavy chain constant domain. More preferably X1 is a linker with the proviso that X1 is not CH1. Most preferably X1 is a linker selected from the group consisting of AKTTPKLEEGEFSEAR (SEQ ID NO:118); AKTTPKLEE-GEFSEARV (SEQ ID NO:119); AKTTPKLGG (SEQ ID NO:120); SAKTTPKLGG; (SEQ ID NO:121); SAKTTP (SEQ ID NO:122); RADAAP (SEQ ID NO:123); RADAAPTVS (SEQ ID NO:124); RADAAAAGGPGS (SEQ ID NO:125); RADAAAA($G_4S$)$_4$ (SEQ ID NO:126); SAKTTPKLEEGEFSEARV (SEQ ID NO:127); ADAAP (SEQ ID NO:40); ADAAPTVSIFPP (SEQ ID NO:103); TVAAP (SEQ ID NO:44); TVAAPSVFIFPP (SEQ ID NO:50); QPKAAP (SEQ ID NO:88); QPKAAPSVTLFPP (SEQ ID NO:92); AKTTPP (SEQ ID NO:38); AKTTPPSVT-PLAP (SEQ ID NO:128); AKTTAP (SEQ ID NO:129); AKT-TAPSVYPLAP (SEQ ID NO:99); ASTKGP (SEQ ID NO:42); ASTKGPSVFPLAP (SEQ ID NO:48), GGGSGGGGSGGGGS (SEQ ID NO:130); GENKVEYA-PALMALS (SEQ ID NO:131); GPAKELTPLKEAKVS (SEQ ID NO:132); and GHEAAAVMQVQYPAS (SEQ ID NO:133). Preferably X2 is an Fc region. More preferably X2 is a variant Fc region.

In a preferred embodiment the binding protein disclosed above comprises a polypeptide chain, wherein said polypeptide chain comprises VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, and X2 is an Fc region.

In another embodiment VD1 and VD2 in the binding protein are light chain variable domains. Preferably the light chain variable domain is selected from the group consisting of a murine light chain variable domain, a human light chain variable domain, a CDR grafted light chain variable domain, and a humanized light chain variable domain. In one embodiment VD1 and VD2 are capable of binding the same antigen. In another embodiment VD1 and VD2 are capable of binding different antigens. Preferably C is a light chain constant domain. More preferably X1 is a linker with the proviso that X1 is not CL1. Preferably X1 is a linker selected from the group consisting of AKTTPKLEEGEFSEAR (SEQ ID NO:118); AKTTPKLEEGEFSEARV (SEQ ID NO:119); AKTTPKLGG (SEQ ID NO:120); SAKTTPKLGG (SEQ ID NO:121); SAKTTP (SEQ ID NO:122); RADAAP (SEQ ID NO:123); RADAAPTVS (SEQ ID NO:124);; RADAAAAG-GPGS (SEQ ID NO:125); RADAAAA($G_4S$)$_4$ (SEQ ID NO:126); SAKTTPKLEEGEFSEARV(SEQ ID NO:127); ADAAP (SEQ ID NO:40); ADAAPTVSIFPP (SEQ ID NO:103); TVAAP (SEQ ID NO:44); TVAAPSVFIFPP (SEQ ID NO:50); QPKAAP (SEQ ID NO:88); QPKAAPS-VTLFPP (SEQ ID NO:92); AKTTPP (SEQ ID NO:38); AKT-TPPSVTPLAP (SEQ ID NO:128); AKTTAP (SEQ ID NO:129); AKTTAPSVYPLAP (SEQ ID NO:99); ASTKGP (SEQ ID NO:42); and ASTKGPSVFPLAP (SEQ ID NO:48); Preferably the binding protein does not comprise X2.

In a preferred embodiment the binding protein disclosed above comprises a polypeptide chain, wherein said polypeptide chain comprises VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region.

In another preferred embodiment the invention provides a binding protein comprising two polypeptide chains, wherein said first polypeptide chain comprises VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, and X2 is an Fc region; and said second polypeptide chain comprises VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region. Most preferably the Dual Variable Domain (DVD) binding protein comprises four polypeptide chains wherein the first two polypeptide chains comprises VD1-(X1)n -VD2-C-(X2)n, respectively wherein VD1 is a first heavy chain variable domain, VD2 is a second heavy chain variable domain, C is a heavy chain constant domain, X1 is a linker with the proviso that it is not CH1, and X2 is an Fc region; and the second two polypeptide chain comprises VD1-(X1)n-VD2-C-(X2)n, respectively, wherein VD1 is a first light chain variable domain, VD2 is a second light chain variable domain, C is a light chain constant domain, X1 is a linker with the proviso that it is not CH1, and X2 does not comprise an Fc region. Such a Dual Variable Domain (DVD) protein has four antigen binding sites.

In another preferred embodiment the binding proteins disclosed above are capable of binding one or more targets. Preferably the target is selected from the group consisting of cytokines, cell surface proteins, enzymes and receptors. Preferably the binding protein is capable of modulating a biological function of one or more targets. More preferably the binding protein is capable of neutralizing one or more targets. The binding protein of the invention is capable of binding cytokines selected from the group consisting of lymphokines, monokines, and polypeptide hormones. In a specific embodiment the binding protein is capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-17; and TNF and IL-15; TNF and VEGF; VEGFR and EGFR; IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2. In another embodiment the binding protein of the invention is capable of binding pairs of targets selected from the group consisting of CD138 and CD20; CD138 and CD40; CD19 and CD20; CD20 and CD3; CD38 & CD138; CD38 and CD20; CD38 and CD40; CD40 and CD20; CD-8 and IL-6; CSPGs and RGM A; CTLA4 and BTNO2; IGF1 and IGF2; IGF1/2 and Erb2B; IL-12 and TWEAK; IL-13 and IL-1β; MAG and RGM A; NgR and RGM A; NogoA and RGM A; OMGp and RGM A; PDL-1 and CTLA4; RGM A and RGM B; Te38 and TNFα ; TNFα and Blys; TNFα and CD-22; TNFα and CTLA-4; TNFα and GP130; TNFα and IL-12p40; and TNFα and RANK ligand.

In one embodiment, the binding protein capable of binding human IL-1α and human IL-1β comprises a DVD heavy chain amino acid sequence selected from the group consisting of SEQ ID NO. 33, SEQ ID NO. 37, SEQ ID NO. 41, SEQ ID NO. 45, SEQ ID NO. 47, SEQ ID NO. 51, SEQ ID NO. 53, SEQ ID NO. 55, SEQ ID NO. 57, and SEQ ID NO. 59; and a DVD light chain amino acid sequence selected from the group consisting of SEQ ID NO. 35, SEQ ID NO. 39, SEQ ID NO. 43, SEQ ID NO. 46, SEQ ID NO. 49, SEQ ID NO. 52, SEQ ID NO. 54, SEQ ID NO. 56, SEQ ID NO. 58, and SEQ ID NO. 60. In another embodiment, the binding protein capable of binding murine IL-1α and murine IL-1β comprises a DVD heavy chain amino acid sequence SEQ ID NO. 105, and a DVD light chain amino acid sequence SEQ ID NO. 109.

In one embodiment, the binding protein capable of binding IL-12 and IL-18 comprises a DVD heavy chain amino acid sequence selected from the group consisting of SEQ ID NO. 83, SEQ ID NO. 90, SEQ ID NO. 93, SEQ ID NO. 95, and SEQ ID NO. 114; and a DVD light chain amino acid sequence selected from the group consisting of SEQ ID NO. 86, SEQ ID NO. 91, SEQ ID NO. 94, SEQ ID NO. 46, SEQ ID NO. 96, and SEQ ID NO. 116.

In one embodiment the binding protein capable of binding CD20 and CD3 comprises a DVD heavy chain amino acid sequence is SEQ ID NO. 97, and a DVD light chain SEQ ID NO. 101.

In another embodiment the binding protein of the invention is capable of binding one, two or more cytokines, cytokine-related proteins, and cytokine receptors selected from the group consisting of BMP1, BMP2, BMP3B (GDF10), BMP4, BMP6, BMP8, CSF1(M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, FIGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

The binding protein of the invention is capable of binding one or more chemokines, chemokine receptors, and chemokine-related proteins selected from the group consisting of CCL1(I-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1(GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HIF1A, IL8, PRL, RGS3, RGS13, SDF2, SLIT2, TLR2, TLR4, TREM1, TREM2, and VHL. The binding protein of the invention is capable of binding cell surface protein selected from the group consisting of integrins. The binding protein of the invention is capable of binding enzyme selected from the group consisting of kinases and proteases. The binding protein of the invention is capable of binding receptor selected from the group consisting of lymphokine receptor, monokine receptor, and polypeptide hormone receptor.

In a preferred embodiment the binding protein is multivalent. More preferably the binding protein is multispecific. The multivalent and or multispecific binding proteins described above have desirable properties particularly from a therapeutic standpoint. For instance, the multivalent and or multispecific binding protein may (1) be internalized (and/or catabolized) faster than a bivalent antibody by a cell expressing an antigen to which the antibodies bind; (2) be an agonist antibody; and/or (3) induce cell death and/or apoptosis of a cell expressing an antigen which the multivalent antibody is capable of binding to. The "parent antibody" which provides at least one antigen binding specificity of the multivalent and or multispecific binding proteins may be one which is internalized (and/or catabolized) by a cell expressing an antigen to which the antibody binds; and/or may be an agonist, cell death-inducing, and/or apoptosis-inducing antibody, and the multivalent and or multispecific binding protein as described herein may display improvement(s) in one or more of these properties. Moreover, the parent antibody may lack any one or more of these properties, but may be endowed with them when constructed as a multivalent binding protein as herein-described.

In another embodiment the binding protein of the invention has an on rate constant (Kon) to one or more targets selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$, as measured by surface plasmon resonance. Preferably, the binding protein of the invention has an on rate constant (Kon) to one or more targets between $10^2 M^{-1}s^{-1}$ to $10^3 M^{-1}s^{-1}$; between $10^3 M^{-1}s^{-1}$ to $10^4 M^{-1}s^{-1}$; between $10^4 M^{-1}s^{-1}$ to $10^5 M^{-1}s^{-1}$; or between $10^5 M^{-1}s^{-1}$ to $10^6 M^{-1}s^{-1}$, as measured by surface plasmon resonance.

In another embodiment the binding protein has an off rate constant (Koff) for one or more targets selected from the group consisting of: at most about $10^{-3} s^{-1}$; at most about $10^{-4} s^{-1}$; at most about $10^{-5} s^{-1}$; and at most about $10^{-4} s^{-1}$, as measured by surface plasmon resonance. Preferably, the binding protein of the invention has an off rate constant (Koff) to one or more targets of $10^{-3} s^{-1}$ to $10^{-4} s^{-1}$; of $10^{-4} s^{-1}$ to $10^{-5} s^{-1}$; or of $10^{-5} s^{-1}$ to $10^{-4} s^{-1}$, as measured by surface plasmon resonance.

In another embodiment the binding protein has a dissociation constant ($K_D$) to one or more targets selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M. Preferably, the binding protein of the invention has a dissociation constant ($K_D$) to IL-12 or IL-23 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of 11 M to $10^{-12}$ M; or of $10^{-12}$ to M $10^{-13}$ M.

In another embodiment the binding protein described above is a conjugate further comprising an agent selected from the group consisting of; an immunoadhension molecule, an imaging agent, a therapeutic agent, and a cytotoxic agent. Preferably the imaging agent is selected from the group consisting of a radiolabel, an enzyme, a fluorescent label, a luminescent label, a bioluminescent label, a magnetic label, and biotin. More preferably the imaging agent is a radiolabel selected from the group consisting of: $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. Preferably the therapeutic or cytotoxic agent is selected from the group consisting of; an anti-metabolite, an alkylating agent, an antibiotic, a growth factor, a cytokine, an anti-angiogenic agent, an anti-mitotic agent, an anthracycline, toxin, and an apoptotic agent.

In another embodiment the binding protein described above is a crystallized binding protein and exists as a crystal. Preferably the crystal is a carrier-free pharmaceutical controlled release crystal. More preferably the crystallized binding protein has a greater half life in vivo than the soluble counterpart of said binding protein. Most preferably the crystallized binding protein retains biological activity.

In another embodiment the binding protein described above is glycosylated. Preferably the glycosylation is a human glycosylation pattern.

One aspect of the invention pertains to an isolated nucleic acid encoding any one of the binding protein disclosed above. A further embodiment provides a vector comprising the isolated nucleic acid disclosed above wherein said vector is selected from the group consisting of pcDNA; pTT (Durocher et al., *Nucleic Acids Research* 2002, Vol 30, No. 2); pTT3 (pTT with additional multiple cloning site; pEFBOS (Mizushima, S. and Nagata, S., (1990) *Nucleic acids Research* Vol 18, No. 17); pBV; pJV; pcDNA3.1 TOPO®, pEF6 TOPO® and pBJ.

In another aspect a host cell is transformed with the vector disclosed above. Preferably the host cell is a prokaryotic cell. More preferably the host cell is *E. Coli*. In a related embodiment the host cell is an eukaryotic cell. Preferably the eukaryotic cell is selected from the group consisting of protist cell, animal cell, plant cell and fungal cell. More preferably the host cell is a mammalian cell including, but not limited to, CHO and COS; or a fungal cell such as *Saccharomyces cerevisiae*; or an insect cell such as Sf9.

Another aspect of the invention provides a method of producing a binding protein disclosed above comprising culturing any one of the host cells also disclosed above in a culture medium under conditions sufficient to produce the binding protein. Preferably 50%-75% of the binding protein produced by this method is a dual specific tetravalent binding protein. More preferably 75%-90% of the binding protein produced by this method is a dual specific tetravalent binding protein. Most preferably 90%-95% of the binding protein produced is a dual specific tetravalent binding protein.

Another embodiment provides a binding protein produced according to the method disclosed above.

One embodiment provides a composition for the release of a binding protein wherein the composition comprises a formulation which in turn comprises a crystallized binding protein, as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The invention also provides a pharmaceutical composition comprising a binding protein, as disclosed above and a pharmaceutically acceptable carrier. In a further embodiment the pharmaceutical composition comprises at least one additional therapeutic agent for treating a disorder. Preferably the additional agent is selected from the group consisting of: Therapeutic agent, imaging agent, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-IL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for treating a human subject suffering from a disorder in which the target, or targets, capable of being bound by the binding protein disclosed above is detrimental, comprising administering to the human subject a binding protein disclosed above such that the activity of the target, or targets in the human subject is inhibited and treatment is achieved. Preferably the disorder is selected from the group comprising arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/ HIV neuropathy, Hodgkin's disease, hyperkinetic movement disorders, hypersentitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia—reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue.

In another aspect the invention provides a method of treating a patient suffering from a disorder comprising the step of administering any one of the binding proteins disclosed above before, concurrent, or after the administration of a second agent, as discussed above. In a preferred embodiment the second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1βmonoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adensosine agonists, antithrombotic agents, complement inhibitors, adrenergic agents, IRAK, NIK, IKK, p38, MAP kinase inhibitors, IL-1β converting enzyme inhibitors, TNFαconverting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1R1, sIL-1R11, sIL-6R, antiinflammatory cytokines, IL-4, IL-10, IL-11, IL-13 and TGFβ.

In a preferred embodiment the pharmaceutical compositions disclosed above are administered to the subject by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one anti-idiotype antibody to at least one binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

In another embodiment the binding proteins of the invention are capable of binding one or more targets selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL 22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21 Wap1/Cip1); CDKN1B (p27Kip1); CDKN1C; CDKN2A (p16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYD1); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB21P; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF1; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; HLA-A; HLA-DRA; HM74; HMOX1; HUMCYT2A; ICEBERG; ICOSL; ID2; IFN-a; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP10; TDGF1; TEK; TGFA; TGFB1; TGFB1I1; TGFB2; TGFB3; TGFB1; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

DETAILED DESCRIPTION OF THE INVENTION

Figure 1:
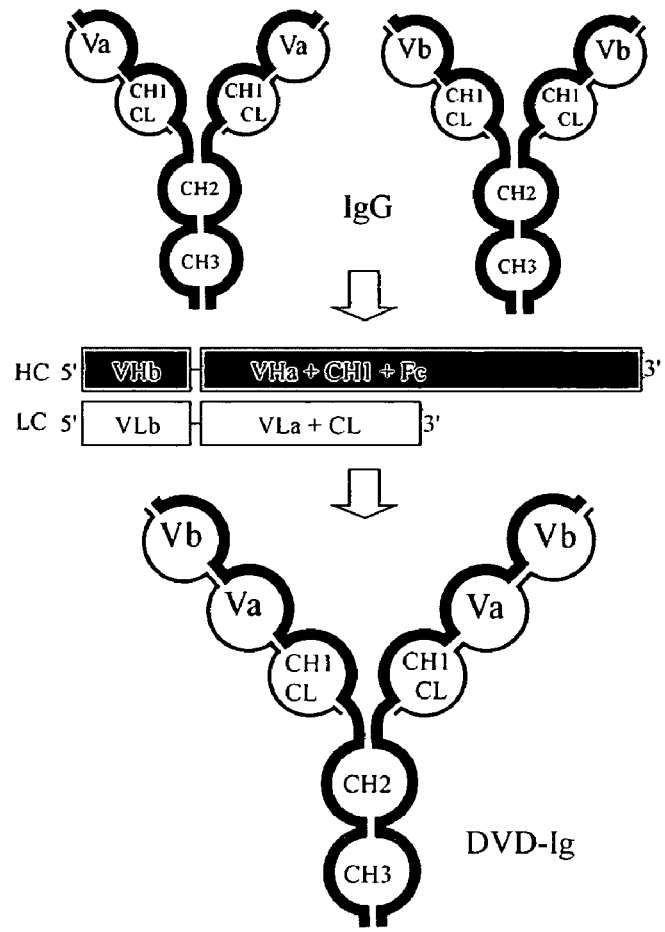
FIG. 1A is a schematic representation of Dual Variable Domain (DVD)-Ig constructs and shows the strategy for generation of a DVD-Ig from two parent antibodies.
FIG. 1B, is a schematic representation of constructs DVD1-Ig, DVD2-Ig, and two chimeric mono-specific antibodies from hybridoma clones 2D13.E3 (anti-IL-1α) and 13F5.G5 (anti-IL-1β).
Figure 1:
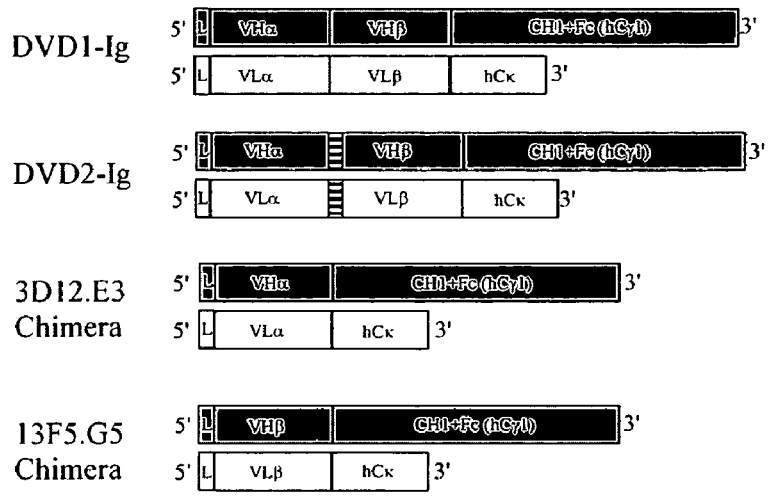

This invention pertains to multivalent and/or multispecific binding proteins capable of binding two or more antigens. Specifically, the invention relates to dual variable domain immunoglobulins (DVD-Ig), and pharmaceutical compositions thereof, as well as nucleic acids, recombinant expression vectors and host cells for making such DVD-Igs. Methods of using the DVD-Igs of the invention to detect specific antigens, either in vitro or in vivo are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

"Biological activity" as used herein, refers to all inherent biological properties of the antigen. Biological properties include but are not limited to binding receptor; induction of cell proliferation, inhibiting cell growth, inductions of other cytokines, induction of apoptosis, and enzymatic activity.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc region to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγR5 and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al. Nature; 264: 415-20; Thies et al 1999 J Mol Biol; 293: 67-79.). Mutation of cysteine residues within the hinge regions to prevent heavy chain-heavy chain disulfide bonds will destabilize dimeration of CH3 domains. Residues responsible for CH3 dimerization have been identified Dall' Acqua 1998 Biochemistry 37: 9266-73.). Therefore, it is possible to generate a monovalent half-Ig. Interestingly, these monovalent half Ig molecules have been found in nature for both IgG and IgA subclasses (Seligman 1978 Ann Immunol 129: 855-70.; Biewenga et al 1983 Clin Exp Immunol 51: 395-400). The stoichiometry of FcRn: Ig Fc region has been determined to be 2:1 (West et al. 2000 Biochemistry 39: 9698-708), and half Fc is sufficient for mediating FcRn binding (Kim et al 1994 Eur J Immunol; 24: 542-548.). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2—CH3 domains. However the half Ig molecule may have certain advantage in tissue penetration due to its smaller size than that of a regular antibody. In one embodiment at least one amino acid residue is replaced in the constant region of the binding protein of the invention, for example the Fc region, such that the dimerization of the heavy chains is disrupted, resulting in half DVD Ig molecules.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-54041354-5). In addition single chain antibodies also include "linear antibodies" comprising a pair of tandem Fv segments (VH-CH1-VH-CH1) which, together with complementary light chain polypeptides, form a pair of antigen binding regions (Zapata et al. Protein Eng. 8(10): 1057-1062 (1995); and U.S. Pat. No. 5,641,870).

The term "multivalent binding protein" is used throughout this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins of the invention comprise two or more antigen binding sites and are tetravalent or multivalent binding proteins. DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

The term "bispecific antibody", as used herein, refers to full-length antibodies that are generated by quadroma technology (see Milstein, C. and A. C. Cuello, Nature, 1983. 305(5934): p. 537-40), by chemical conjugation of two different mAbs (see Staerz, U. D., et al., Nature, 1985. 314 (6012): p. 628-31), or by knob-into-hole or similar approaches which introduces mutations in the Fc region (see Holliger, P., T. Prospero, and G. Winter, Proc Natl Acad Sci USA, 1993. 90(14): p. 6444-8.18), resulting in multiple different immunogloblin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is mono-valent for each antigen it binds to.

The term "dual-specific antibody", as used herein, refers to full-length antibodies that can bind two different antigens (or epitopes) in each of its two binding arms (a pair of HC/LC) (see PCT publication WO 02/02773). Accordingly a dual-specific binding protein has two identical antigen binding arms, with identical specificity and identical CDR sequences, and is bi-valent for each antigen it binds to.

A "functional antigen binding site" of a binding protein is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

The term "cytokine" is a generic term for proteins released by one cell population, which act on another cell population as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-1 and -11; erythropoietin (EPO); osteoinductive factors; interferons such as interferon-alpha, -beta and -gamma colony stimulating factors (CSFs) such as macrophage-CSF (M-CSF); granulocyte macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-10, IL-11, IL-12, IL-13, IL-15, IL-18, IL-23; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The term "Linker" is used to denote polypeptides comprising two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). Preferred linker include, but are not limited to, AKTTP-KLEEGEFSEAR (SEQ ID NO:118); AKTTPKLEEGEF-SEARV (SEQ ID NO:119); AKTTPKLGG (SEQ ID NO:120); SAKTTPKLGG (SEQ ID NO:121); SAKTTP NO:122); RADAAP (SEQ ID NO:123); RADAAPTVS (SEQ ID NO:124); RADAAAAGGPGS (SEQ ID NO:125); RADAAAA($G_4S$)$_4$ (SEQ ID NO:126); SAKTTPKLEEGEF-SEARV (SEQ ID NO:127); ADAAP (SEQ ID NO:40); ADAAPTVSIFPP (SEQ ID NO:103); TVAAP (SEQ ID NO:44); TVAAPSVFIFPP (SEQ ID NO:50); QPKAAP(SEQ ID NO:88); QPKAAPSVTLFPP (SEQ ID NO:92); AKTTPP (SEQ ID NO:38); AKTTPPSVTPLAP (SEQ ID NO:128); AKTTAP (SEQ ID NO:129); AKTTAPSVYPLAP (SEQ ID NO:99); ASTKGP (SEQ ID NO:42); ASTKGPSVFPLAP (SEQ ID NO:48).

An immunoglobulin constant domain refers to a heavy or light chain constant domain. Human IgG heavy chain and light chain constant domain amino acid sequences are known in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-

370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. BidlTechnology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

As used herein, the term "neutralizing" refers to neutralization of biological activity of a cytokine when a binding protein specifically binds the cytokine. Preferably the neutralizing binding protein binds the cytokine and reduces its biologically activity by at least about 20%, 40%, 60%, 80%, 85% or more.

The term "activity" includes activities such as the binding specificity/affinity of a DVD-Ig for two or more antigens.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of a cytokine). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of a cytokine). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, polypeptides, nucleic acids, carbohydrates, or any other molecules that bind to the antigen.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of the antigen. Antagonists and inhibitors of antigens may include, but are not limited to, proteins, nucleic acids, carbohydrates, or any other molecules, which bind to the antigen.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Generation of DVD Binding Protein

The invention pertains to Dual Variable Domain binding proteins capable of binding one or more targets and methods of making the same. Preferably the binding protein comprises a polypeptide chain, wherein said polypeptide chain comprises VD1-(X1)n-VD2-C-(X2)n, wherein VD1 is a first variable domain, VD2 is a second variable domain, C is a constant domain, X1 represents an amino acid or polypeptide, X2 represents an Fc region and n is 0 or 1. The binding protein of the invention can be generated using various techniques. The invention provides expression vectors, host cell and methods of generating the binding protein.

A. Generation of Parent Monoclonal Antibodies

The variable domains of the DVD binding protein can be obtained from parent antibodies, including polyclonal and monoclonal antibodies capable of binding antigens of interest. These antibodies may be naturally occurring or may be generated by recombinant technology.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Hybridomas are selected, cloned and further screened for desirable characteristics, including robust hybridoma growth, high antibody production and desirable antibody characteristics, as discussed in Example 1 below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art. In a preferred embodiment, the hybridomas are mouse hybridomas. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an antibody capable of binding a specific antigen.

Recombinant monoclonal antibodies are also generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) Proc. Natl. Acad. Sci. USA 93:7843-7848. In this method, single cells secreting antibodies of interest, e.g., lymphocytes derived from an immunized animal, are identified, and, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to the antigen of interest. The amplified immunoglobulin sequences further can be manipulated in vitro, such as by in vitro affinity maturation methods such as those described in PCT Publication WO 97/29131 and PCT Publication WO 00/56772.

Monoclonal antibodies are also produced by immunizing a non-human animal comprising some, or all, of the human immunoglobulin locus with an antigen of interest. In a preferred embodiment, the non-human animal is a XENOMOUSE® transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE® transgenic mouse produces an adult-like human repertoire of fully human antibodies, and generates antigen-specific human Mabs. The XENOMOUSE® transgenic mouse contains approximately 80% of the human antibody repertoire through introduction of megabase sized, germline configuration YAC fragments of the human heavy chain loci and x light chain loci. See Mendez et al., *Nature*

*Genetics* 15:146-156 (1997), Green and Jakobovits *J. Exp. Med.* 188:483-495 (1998), the disclosures of which are hereby incorporated by reference.

In vitro methods also can be used to make the parent antibodies, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

Parent antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

Alternative to screening of recombinant antibody libraries by phage display, other methodologies known in the art for screening large combinatorial libraries can be applied to the identification of parent antibodies. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the parent antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the parent antibodies include those disclosed in Wittrup, et al. U.S. Pat. No. 6,699,658 incorporated herein by reference.

The antibodies described above can be further modified to generate CDR grafted and Humanized parent antibodies. CDR-grafted parent antibodies comprise heavy and light chain variable region sequences from a human antibody wherein one or more of the CDR regions of VH and/or VL are replaced with CDR sequences of murine antibodies capable of binding antigen of interest. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs have at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing such antibodies are known in the art (see EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352).

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.s-ciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.html; www.library.thinkquest.org/12429/Immune/Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/Immunology.html.www.immunologylink.com/; pathbox.wustl.edu/.about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Eli sa.html; www.biodesign.com/table.asp; www.icnet.uk/axp/facs/davies/lin-ks.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.aboutjraats/linksl.html; www.recab.uni-hd.de/immuno.bme.nwu.edu/; www.mrc-cpe.cam.ac.uk/imt-doc/pu-blic/INTRO.html; www.ib-t.unam.mx/virV_-mice.html; imgt.cnusc.fr:8104/; www.bio-chem.ucl.ac.uk/.about.martin/abs/index.html; antibody.bath.ac.uk/; abgen.cvm.tamu.edu/lab/wwwab-gen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.bio-sci.missouri.edu/smithgp/index.html; www.cryst.bioc.ca-m.ac.uk/.abo-ut.fmolina/Webpages/Pept/spottech.html; www.jerini.de/fr roducts.htm; www.patents.ibm.con/ibm.ht-ml.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

Parent monoclonal antibodies may be selected from various monoclonal antibodies capable of binding specific targets and well known in the art. These include, but are not limited to anti-TNF antibody (U.S. Pat. No. 6,258,562), anti-IL-12 and or anti-IL-12p40 antibody (U.S. Pat. No. 6,914,128); anti-IL-18 antibody (US 2005/0147610 A1), anti-C5, anti-CBL, anti-CD147, anti-gp120, anti-VLA4, anti-CD11a, anti-CD18, anti-VEGF, anti-CD40L, anti-Id, anti-ICAM-1, anti-CXCL13, anti-CD2, anti-EGFR, anti-TGF-beta 2, anti-E-selectin, anti-Fact VII, anti-Her2/neu, anti-F gp, anti-CD11/18, anti-CD14, anti-ICAM-3, anti-CD80, anti-CD4, anti-CD3, anti-CD23, anti-beta2-integrin, anti-alpha4beta7, anti-CD52, anti-HLA DR, anti-CD22, anti-CD20, anti-MIF, anti-CD64 (FcR), anti-TCR alpha beta, anti-CD2, anti-Hep B, anti-CA 125, anti-EpCAM, anti-gp120, anti-CMV, anti-gpIbIIIa, anti-IgE, anti-CD25, anti-CD33, anti-HLA, anti-VN-Rintegrin, anti-IL-1alpha, anti-IL-1beta, anti-IL-1 receptor, anti-IL-2 receptor, anti-IL-4, anti-IL4 receptor, anti-IL5, anti-IL-5 receptor, anti-IL-6, anti-IL-8, anti-IL-9, anti-IL-13, anti-IL-13 receptor, anti-IL-17, and anti-IL-23 (see Presta LG. 2005 Selection, design, and engineering of therapeutic antibodies J Allergy Clin Immunol. 116:731-6 and Clark, M., "Antibodies for Therapeutic Applications," Department of Pathology, Cambridge University, UK, 15 Oct. 2000, published online at M. Clark's home page at the website for the Department of Pathology, Cambridge University).

Parent monoclonal antibodies may also be selected from various therapeutic antibodies approved for use, in clinical trials, or in development for clinical use. Such therapeutic antibodies include, but are not limited to, RITUXAN®, IDEC/Genentech/Roche) (see for example U.S. Pat. No. 5,736,137), a chimeric anti-CD20 antibody approved to treat Non-Hodgkin's lymphoma; HUMAX-CD20®, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"), trastuzumab (HERCEPTIN®, Genentech) (see for example U.S. Pat. No. 5,677,171), a humanized anti- Her2/neu antibody approved to treat breast cancer; pertuzumab (rhuMab-2C4, OMNITARG®), currently being developed by Genentech; an anti-Her2 antibody described in U.S. Pat. No. 4,753,894; cetuximab (ERBITUX®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HUMAX-EGFR™ (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); ICR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraCIM hR3 (YM Biosciences, Canada and Centro de Immunologia Molecular, Cuba (U.S. Pat. No. 5,891,996; U.S. Pat. No. 6,506,883; Mateo et al, 1997, Immunotechnology, 3(1):71-81); mAb-806 (Ludwig Institute for Cancer Research, Memorial Sloan-Kettering) (Jungbluth et al. 2003, Proc Natl Acad Sci USA. 100(2):639-44); KSB-102 (KS Biomedix); MR1-1 (IVAX, National Cancer Institute) (PCT WO 0162931A2); and SC100 (Scancell) (PCT WO 01/88138); alemtuzumab (CAMPATH®, Millennium), a humanized monoclonal antibody currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (ZEVALIN®), an anti-CD20 antibody developed by IDEC/Schering AG, gemtuzumab ozogamicin (MYLOTARG®), an anti-CD33 (p67 protein) antibody developed by Celltech/Wyeth, alefacept (AMEVIVE®), an anti-LFA-3 Fc fusion developed by Biogen), abciximab (REOPRO®), developed by Centocor/Lilly, basiliximab (SIMULECT®), developed by Novartis, palivizumab (SYNAGIS®), developed by Medimmune, infliximab (REMICADE®), an anti-TNFalpha antibody developed by Centocor, adalimumab (HUMIRA®), an anti-TNFalpha antibody developed by Abbott, HUMICADE®, an anti-TNFalpha antibody developed by Celltech, etanercept (ENBREL®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, ANTEGREN® (natalizumab), an anti-alpha-4-beta-1 (VLA4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β2 antibody being developed by Cambridge Antibody Technology, J695, an anti-IL-12 antibody being developed by Cambridge Antibody Technology and Abbott, CAT-192, an anti-TGFβ1 antibody being developed by Cambridge Antibody Technology and Genzyme, CAT-213, an anti-Eotaxin1 antibody being developed by Cambridge Antibody Technology, LYMPHOSTAT-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., AVASTIN® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, XOLAIR® (Omalizumab), an anti-IgE antibody being developed by Genentech, RAPTIVA® (Efalizumab), an anti-CD11a antibody being developed by Genentech and Xoma, MLN-02 Antibody (formerly LDP-02), being developed by Genentech and Millennium Pharmaceuticals, HUMAX CD4®, an anti-CD4 antibody being developed by Genmab, HUMAX™-IL15, an anti-IL15 antibody being developed by Genmab and Amgen, HUMAX™-Inflam, being developed by Genmab and Medarex, HUMAX™-Cancer, an anti-Heparanase I antibody being developed by Genmab and Medarex and Oxford GlycoSciences, HUMAX™-Lymphoma, being developed by Genmab and Amgen, HUMAX™-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-CIDE® (labetuzumab), an anti-carcinoembryonic antigen (CEA) antibody being developed by Immunomedics, LYMPHOCIDE® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, OSIDEM® (IDM-1), and anti-Her2 antibody being developed by Medarex and Immuno-Designed Molecules, HUMAX®-CD4, an anti-CD4 antibody being developed by Medarex and Genmab, HuMax-IL15, an anti-IL15 antibody being developed by Medarex and Genmab, CNTO 148, an anti-TNFa antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, NUVION® (visilizumab), an anti-CD3 antibody being developed by Protein Design Labs, HUZAF®, an anti-gamma interferon antibody being developed by Protein Design Labs, Anti-a 5β1 Integrin, being developed by Protein Design Labs, anti-IL-12, being developed by Protein Design Labs, ING-1, an anti-Ep-CAM antibody being developed by Xoma, XOLAIR® (Omalizumab) a humanized anti-IgE antibody developed by Genentech and Novartis, and MLN01, an anti-Beta2 integrin antibody being developed by Xoma, all of the above-cited references in this paragraph are expressly incorporated herein by reference.

B. Construction of DVD Molecules:

The dual variable domain immunoglobulin (DVD-Ig) molecule is designed such that two different light chain variable domains (VL) from the two different parent mAbs are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region (FIG. 1A).

The variable domains can be obtained using recombinant DNA techniques from a parent antibody generated by any one of the methods described above. In a preferred embodiment the variable domain is a murine heavy or light chain variable domain. More preferably the variable domain is a CDR grafted or a humanized variable heavy or light chain domain. Most preferably the variable domain is a human heavy or light chain variable domain.

In one embodiment the first and second variable domains are linked directly to each other using recombinant DNA techniques. In another embodiment the variable domains are linked via a linker sequence. Preferably two variable domains are linked. Three or more variable domains may also be linked directly or via a linker sequence. The variable domains may bind the same antigen or may bind different antigens. DVD molecules of the invention may include one immunoglobulin variable domain and one non-immunoglobulin variable domain such as ligand binding domain of a receptor, active domain of an enzyme. DVD molecules may also comprise 2 or more non-Ig domains.

The linker sequence may be a single amino acid or a polypeptide sequence. Preferably the linker sequences are selected from the group consisting of AKTTPKLEEGEFSEAR (SEQ ID NO:118); AKTTPKLEEGEFSEARV (SEQ ID NO:119); AKTTPKLGG (SEQ ID NO:120); SAKTTPKLGG (SEQ ID NO:121); SAKTTP (SEQ ID NO:122); RADAAP (SEQ ID NO:123); RADAAPTVS (SEQ ID NO:124); RADAAAAGGPGS (SEQ ID NO:125); RADAAAA($G_4S$)$_4$ (SEQ ID NO:126), SAKTTPKLEEGEFSEARV (SEQ ID NO:127); ADAAP (SEQ ID NO:40); ADAAPTVSIFPP (SEQ ID NO:103); TVAAP (SEQ ID NO:44); TVAAPSVFIFPP (SEQ ID NO:50); QPKAAP (SEQ ID NO:88); QPKAAPSVTLFPP (SEQ ID NO:92); AKTTPP (SEQ ID NO:38); AKTTPPSVTPLAP (SEQ ID NO:128); AKTTAP (SEQ ID NO:129); AKTTAPSVYPLAP (SEQ ID NO:99); ASTKGP (SEQ ID NO:42); ASTKGPSVFPLAP (SEQ ID NO:48); GGGGSGGGGSGGGGS (SEQ ID NO:130); GENKVEYAPALMALS (SEQ ID NO:131); GPAKELTPLKEAKVS (SEQ ID NO:132); and GHEAAAVMQVQYPAS (SEQ ID NO:133). The choice of linker sequences is based on crystal structure analysis of several Fab molecules. There is a natural flexible linkage between the variable domain and the CH1/CL constant domain in Fab or antibody molecular structure. This natural linkage comprises approximately 10-12 amino acid residues, contributed by 4-6 residues from C-terminus of V domain and 4-6 residues from the N-terminus of CL/CH1 domain. DVD Igs of the invention were generated using N-terminal 5-6 amino acid residues, or 11-12 amino acid residues, of CL or CH1 as linker in light chain and heavy chain of DVD-Ig, respectively. The N-terminal residues of CL or CH1 domains, particularly the first 5-6 amino acid residues, adopt a loop conformation without strong secondary structures, therefore can act as flexible linkers between the two variable domains. The N-terminal residues of CL or CH1 domains are natural extension of the variable domains, as they are part of the Ig sequences, therefore minimize to a large extent any immunogenicity potentially arising from the linkers and junctions.

Other linker sequences may include any sequence of any length of CL/CH1 domain but not all residues of CL/CH1 domain; for example the first 5-12 amino acid residues of the CL/CH1 domains; the light chain linkers can be from Cκ or Cλ; and the heavy chain linkers can be derived from CH1 of any isotypes, including Cγ1, Cγ2, Cγ3, Cγ4, Cα1, Cα2, Cδ, Cε, and Cμ. Linker sequences may also be derived from other proteins such as Ig-like proteins, (e.g. TCR, FcR, KIR); G/S based sequences (e.g G4S repeats); hinge region-derived sequences; and other natural sequences from other proteins.

In a preferred embodiment a constant domain is linked to the two linked variable domains using recombinant DNA techniques. Preferably sequence comprising linked heavy chain variable domains is linked to a heavy chain constant domain and sequence comprising linked light chain variable domains is linked to a light chain constant domain. Preferably the constant domains are human heavy chain constant domain and human light chain constant domain respectively. Most preferably the DVD heavy chain is further linked to an Fc region. The Fc region may be a native sequence Fc region, or a variant Fc region. Most preferably the Fc region is a human Fc region. In a preferred embodiment the Fc region includes Fc region from IgG1, IgG2, IgG3, IgG4, IgA, IgM, IgE, or IgD.

In a most preferred embodiment two heavy chain DVD polypeptides and two light chain DVD polypeptides are combined to form a DVD-Ig molecule. Detailed description of specific DVD-Ig molecules capable of binding specific targets, and methods of making the same, is provided in the Examples section below.

C. Production of DVD Proteins

Binding proteins of the present invention may be produced by any of a number of techniques known in the art. For example, expression from host cells, wherein expression vector(s) encoding the DVD heavy and DVD light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the DVD proteins of the invention in either prokaryotic or eukaryotic host cells, expression of DVD proteins in eukaryotic cells is preferable, and most preferable in mammalian host cells, because such eukaryotic cells (and in particular mammalian cells) are more likely than prokaryotic cells to assemble and secrete a properly folded and immunologically active DVD protein.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding DVD proteins are introduced into mammalian host cells, the DVD proteins are produced by culturing the host cells for a period of time sufficient to allow for expression of the DVD proteins in the host cells or, more preferably, secretion of the DVD proteins into the culture medium in which the host cells are grown. DVD proteins can be recovered from the culture medium using standard protein purification methods.

In a preferred system for recombinant expression of DVD proteins of the invention, a recombinant expression vector encoding both the DVD heavy chain and the DVD light chain is introduced into dhfr-CHO cells by calcium phosphate-mediated transfection. Within the recombinant expression vector, the DVD heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the DVD heavy and light chains and intact DVD protein is recovered from the culture medium. Standard molecular biology techniques are used to prepare the recombinant expression vector, transfect the host cells, select for transformants, culture the host cells and recover the DVD protein from the culture medium. Still further the invention provides a method of synthesizing a DVD protein of the invention by culturing a host cell of the invention in a suitable culture medium until a DVD protein of the invention is synthesized. The method can further comprise isolating the DVD protein from the culture medium.

An important feature of DVD-Ig is that it can be produced and purified in a similar way as a conventional antibody. The production of DVD-Ig results in a homogeneous, single major product with desired dual-specific activity, without any sequence modification of the constant region or chemical modifications of any kind. Other previously described methods to generate "bi-specific", "multi-specific", and "multi-specific multivalent" full length binding proteins do not lead to a single primary product but instead lead to the intracellular or secreted production of a mixture of assembled inactive, mono-specific, multi-specific, multivalent, full length binding proteins, and multivalent full length binding proteins with combination of different binding sites. As an example, based on the design described by Miller and Presta (PCT publication WO2001/077342(A1), there are 16 possible combinations of heavy and light chains. Consequently only 6.25% of protein is likely to be in the desired active form. Separation of fully active forms of the protein from inactive and partially active forms of the protein using standard chromatography techniques, typically used in large scale manufacturing, is yet to be demonstrated.

Surprisingly the design of the "dual-specific multivalent full length binding proteins" of the present invention leads to a dual variable domain light chain and a dual variable domain heavy chain which assemble primarily to the desired "dual-specific multivalent full length binding proteins".

At least 50%, preferably 75% and more preferably 90% of the assembled, and expressed dual variable domain immunoglobulin molecules are the desired dual-specific tetravalent protein. This aspect of the invention particularly enhances the commercial utility of the invention. Therefore, the present invention includes a method to express a dual variable domain light chain and a dual variable domain heavy chain in a single cell leading to a single primary product of a "dual-specific tetravalent full length binding protein".

The present invention provides a preferred method to express a dual variable domain light chain and a dual variable domain heavy chain in a single cell leading to a "primary product" of a "dual-specific tetravalent full length binding protein", where the "primary product" is more than 50% of all assembled protein, comprising a dual variable domain light chain and a dual variable domain heavy chain.

The present invention provides a more preferred method to express a dual variable domain light chain and a dual variable domain heavy chain in a single cell leading to a single "primary product" of a "dual-specific tetravalent full length binding protein", where the "primary product" is more than 75% of all assembled protein, comprising a dual variable domain light chain and a dual variable domain heavy chain.

The present invention provides a most preferred method to express a dual variable domain light chain and a dual variable domain heavy chain in a single cell leading to a single "primary product" of a "dual-specific tetravalent full length binding protein", where the "primary product" is more than 90% of all assembled protein, comprising a dual variable domain light chain and a dual variable domain heavy chain.

II. Derivatized DVD Binding Proteins:

One embodiment provides a labeled binding protein wherein the binding protein of the invention is derivatized or linked to another functional molecule (e.g., another peptide or protein). For example, a labeled binding protein of the invention can be derived by functionally linking an binding protein of the invention (by chemical coupling, genetic fusion, non-covalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the binding protein with another molecule (such as a streptavidin core region or a polyhistidine tag).

Useful detectable agents with which a binding protein of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. A binding protein may also be derivatized with detectable enzymes, such as alkaline phosphatase, horseradish peroxidase, glucose oxidase and the like. When a binding protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. a binding protein may also be derivatized with biotin, and detected through indirect measurement of avidin or streptavidin binding.

Another embodiment of the invention provides a crystallized binding protein and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02072636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity but have increased or decreased binding activity are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified binding protein of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S patent applications 20040018590 and 20020137134 and PCT publication WO2005100584 A2).

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

III. Uses of DVD-Ig

Given their ability to bind to two or more antigens the binding proteins of the invention can be used to detect the antigens (e.g., in a biological sample, such as serum or plasma), using a conventional immunoassay, such as an enzyme linked immunosorbent assays (ELISA), an radioimmunoassay (RIA) or tissue immunohistochemistry. The DVD-Ig is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{113}I$, $^{177}Lu$, $^{166}Ho$, and $^{153}Sm$.

The binding proteins of the invention preferably are capable of neutralizing the activity of the antigens both in vitro and in vivo. Accordingly, such DVD-Igs can be used to inhibit antigen activity, e.g., in a cell culture containing the antigens, in human subjects or in other mammalian subjects having the antigens with which a binding protein of the invention cross-reacts. In another embodiment, the invention provides a method for reducing antigen activity in a subject suffering from a disease or disorder in which the antigen activity is detrimental. A binding protein of the invention can be administered to a human subject for therapeutic purposes.

As used herein, the term "a disorder in which antigen activity is detrimental" is intended to include diseases and other disorders in which the presence of the antigen in a subject suffering from the disorder has been shown to be or is suspected of being either responsible for the pathophysiology of the disorder or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc. of the subject). Non-limiting examples of disorders that can be treated with the binding proteins of the invention include those disorders discussed below and in the section pertaining to pharmaceutical compositions of the antibodies of the invention.

The DVD-Igs of the invention may bind one antigen or multiple antigens. Such antigens include, but are not limited to, the targets listed in the following databases, which databases are incorporated herein by reference. These target databases include those listings:

Therapeutic targets (http://xin.cz3.nus.edu.sg/group/cjttd/tt-d.asp);

Cytokines and cytokine receptors (http://www.cytokineweb-facts.com/, http://www.copewithcytokines.de/cope.cgi, and http://cmbi.bjmu.edu.cn/cmbidata/cgf/CGF_Database/cytokine.medic.kumamotou.ac.jp/CFC/indexR.html);

Chemokines (http://cytokine.medic.kumamoto-u.ac jp/CFC/CK/Chemokine.html);

Chemokine receptors and GPCRs (http://csp.medic.kumamoto-u.acjp/CSP/Receptor.html, http://www.gpcr.org/7tm/);

Olfactory Receptors (http://senselab.med.yale.edu/senselab/ORDB/default.asp);

Receptors (http://www.iuphar-db.org/iuphar-rd/list/index.htm);

Cancer targets (http://cged.hgcjp/cgi-bin/input.cgi);

Secreted proteins as potential antibody targets (http://spd.cbi.pku.edu.cn/);

Protein kinases (http://spd.cbi.pku.edu.cn/), and Human CD markers (http://content.labvelocity.com/tools/6/1226/CD_ table_final_locked.pdf) and (Zola H, 2005 CD molecules 2005: human cell differentiation molecules Blood, 106:3123-6).

DVD-Igs are useful as therapeutic agents to simultaneously block two different targets to enhance efficacy/safety and/or increase patient coverage. Such targets may include soluble targets (IL-13 and TNF) and cell surface receptor targets (VEGFR and EGFR). It can also be used to induce redirected cytotoxicity between tumor cells and T cells (Her2 and CD3) for cancer therapy, or between autoreactive cell and effectoe cells for autoimmune/transplantation, or between any target cell and effector cell to eliminate disease-causing cells in any given disease.

In addition, DVD-Ig can be used to trigger receptor clustering and activation when it is designed to target two different epitopes on the same receptor. This may have benefit in making agonistic and antagonistic anti-GPCR therapeutics. In this case, DVD-Ig can be used to target two different epitopes on one cell for clustering/signaling (two cell surface molecules) or signaling (on one molecule). Similarly, a DVD-Ig molecule can be designed to trigger CTLA-4 ligation, and a negative signal by targeting two different epitopes (or 2 copies of the same epitope) of CTLA4 extracellular domain, leading to down regulation of the immune response. CTLA-4 is a clinically validated target for therapeutic treatment of a number of immunological disorders. CTLA4/B7 interactions negatively regulate T cell activation by attenuating cell cycle progression, IL-2 production, and proliferation of T cells following activation, and CTLA4 (CD152) engagement can down-regulate T cell activation and promote the induction of immune tolerance. However, the strategy of attenuating T cell activation by agonistic antibody engagement of CTLA4 has been unsuccessful since CTLA-4 activation requires ligation. The molecular interaction of CTLA-4/B7 is in "skewed zipper" arrays, as demonstrated by crystal structural analysis (Stamper 2001 Nature 410:608). However none of the currently available CTLA-4 binding reagents have ligation properties, including anti-CTLA4 monoclonal antibodies. There have been several attempts to address this issue. In one case, a cell member-bound single chain antibody was generated, and significantly inhibited allogeneic rejection in mice (Hwang 2002 JI 169:633). In a separate case, artificial APC surface-linked single-chain antibody to CTLA4 was generated and demonstrated to attenuate T cell responses (Griffin 2000 JI 164:4433). In both cases, CTLA-4 ligation was achieved by closely localized member-bound antibodies in artificial systems. While these experiments provide proof-of-concept for immune down-regulation by triggering CTLA-4 negative signaling, the reagents used in these reports are not suitable for therapeutic use. To this end, CTLA-4 ligation may be achieved by using a DVD-Ig molecule, which target two different epitopes (or 2 copies of the same epitope) of CTLA4 extracellular domain. The rationale is that the distance spanning two binding sites of an IgG, approximately 150-170A, is too large for active ligation of CTLA-4 (30-50 Å between 2 CTLA4 homodimer). However the distance between the two binding sites on DVD-Ig (one arm) is much shorter, also in the range of 30-50 Å, allowing proper ligation of CTLA4.

Similarly, DVD-Ig can target two different members of a cell surface receptor complex (e.g. IL-12R alpha and beta). Furthermore, DVD-Ig can target CR1 and a soluble protein/pathogen to drive rapid clearance of the target soluble protein/pathogen.

Additionally, DVD-Igs of the invention can be employed for tissue-specific delivery (target a tissue marker and a disease mediator for enhanced local PK thus higher efficacy and/or lower toxicity), including intracellular delivery (targeting an internalizing receptor and a intracellular molecule), delivering to inside brain (targeting transferrin receptor and a CNS disease mediator for crossing the blood-brain barrier). DVD-Ig can also serve as a carrier protein to deliver an antigen to a specific location via binding to a non-neutralizing epitope of that antigen and also to increase the half-life of the antigen. Furthermore, DVD-Ig can be designed to either be physically linked to medical devices implanted into patients or target these medical devices (see Burke, Sandra E.; Kuntz, Richard E.; Schwartz, Lewis B., Zotarolimus (ABT-578) eluting stents. Advanced Drug Delivery Reviews (2006), 58(3), 437-446; Surface coatings for biological activation and functionalization of medical devices, Hildebrand, H. F.; Blanchemain, N.; Mayer, G.; Chai, F.; Lefebvre, M.; Boschin, F., Surface and Coatings Technology (2006), 200(22-23), 6318-6324; Drug/device combinations for local drug therapies and infection prophylaxis, Wu, Peng; Grainger, David W., Biomaterials (2006), 27(11), 2450-2467; Mediation of the cytokine network in the implantation of orthopedic devices., Marques, A. P.; Hunt, J. A.; Reis, Rui L., Biodegradable Systems in Tissue Engineering and Regenerative Medicine (2005), 377-397). Briefly, directing appropriate types of cell to the site of medical implant may promote healing and restoring normal tissue function. Alternatively, inhibition of mediators (including but not limited to cytokines), released upon device implantation by a DVD coupled to or target to a device is also provided. For example, Stents have been used for years in interventional cardiology to clear blocked arteries and to improve the flow of blood to the heart muscle. However, traditional bare metal stents have been known to cause restenosis (re-narrowing of the artery in a treated area) in some patients and can lead to blood clots. Recently, an anti-CD34 antibody coated stent has been described which reduced restenosis and prevents blood clots from occurring by capturing endothelial progenitor cells (EPC) circulating throughout the blood. Endothelial cells are cells that line blood vessels, allowing blood to flow smoothly. The EPCs adhere to the hard surface of the stent forming a smooth layer that not only promotes healing but prevents restenosis and blood clots, complications previously associated with the use of stents (Aoji et al. 2005 J Am Coll Cardiol. 45(10): 1574-9). In addition to improving outcomes for patients requiring stents, there are also implications for patients requiring cardiovascular bypass surgery. For example, a prosthetic vascular conduit (artificial artery) coated with anti-EPC antibodies would eliminate the need to use arteries from patients legs or arms for bypass surgery grafts. This would reduce surgery and anesthesia times, which in turn will reduce coronary surgery deaths. DVD-Ig are designed in such a way that it binds to a cell surface marker (such as CD34) as well as a protein (or an epitope of any kind, including but not limited to lipids and polysaccharides) that has been coated on the implanted device to facilitate the cell recruitment. Such approaches can also be applied to other medical implants in general. Alternatively, DVD-Igs can be coated on medical devices and upon implantation and releasing all DVDs from the device (or any other need which may require additional fresh DVD-Ig, including aging and denaturation of the already loaded DVD-Ig) the device could be reloaded by systemic administration of fresh DVD-Ig to the patient, where the DVD-Ig is designed to binds to a target of interest (a cytokine, a cell surface marker (such as CD34) etc.) with one set of binding sites and to a target coated on the device (including a protein, an epitope of any kind, including but not limited to lipids, polysaccharides and polymers) with the other. This technology has the advantage of extending the usefulness of coated implants.

A. Use of DVD-Igs in Various Diseases

DVD-Ig molecules of the invention are also useful as therapeutic molecules to treat various diseases. Such DVD molecules may bind one or more targets involved in a specific disease. Examples of such targets in various diseases are described below.

1. Human Autoimmune and Inflammatory Response

Many proteins have been implicated in general autoimmune and inflammatory responses, including C5, CCL1 (1-309), CCL11 (eotaxin), CCL13 (mcp-4), CCL15 (MIP-Id), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11(1-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL1, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, 18RB, IL9, IL9R, IL10, IL10RA, IL10RB, IL11, IL11RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1l1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144). In one aspect, DVD-Igs capable of binding one or more of the targets listed above are provided.

2. Asthma

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. It is now widely accepted that airway inflammation is the key factor underlying the pathogenesis of asthma, involving a complex interplay of inflammatory cells such as T cells, B cells, eosinophils, mast cells and macrophages, and of their secreted mediators including cytokines and chemokines. Corticosteroids are the most important anti-inflammatory treatment for asthma today, however their mechanism of action is non-specific and safety concerns exist, especially in the juvenile patient population. The development of more specific and targeted therapies is therefore warranted. There is increasing evidence that IL-13 in mice mimics many of the features of asthma, including AHR, mucus hypersecretion and airway fibrosis, independently of eosinophilic inflammation (Finotto et al., International Immunology (2005), 17(8), 993-1007; Padilla et al., Journal of Immunology (2005), 174(12), 8097-8105).

IL-13 has been implicated as having a pivotal role in causing pathological responses associated with asthma. The development of anti-IL-13 monoclonal antibody therapy to reduce the effects of IL-13 in the lung is an exciting new approach that offers considerable promise as a novel treatment for asthma. However other mediators of differential immunological pathways are also involved in asthma pathogenesis, and blocking these mediators, in addition to IL-13, may offer additional therapeutic benefit. Such target pairs include, but are not limited to, IL-13 and a pro-inflammatory cytokine, such as tumor necrosis factor-α (TNF-α). TNF-α may amplify the inflammatory response in asthma and may be linked to disease severity (McDonnell, et al., Progress in Respiratory Research (2001), 31(New Drugs for Asthma, Allergy and COPD), 247-250.). This suggests that blocking both IL-13 and TNF-α may have beneficial effects, particularly in severe airway disease. In a preferred embodiment the DVD-Ig of the invention binds the targets IL-13 and TNFα and is used for treating asthma.

Animal models such as OVA-induced asthma mouse model, where both inflammation and AHR can be assessed, are known in the art and may be used to determine the ability of various DVD-Ig molecules to treat asthma. Animal models for studying asthma are disclosed in Coffman, et al., Journal of Experimental Medicine (2005), 201(12), 1875-1879; Lloyd, et al., Advances in Immunology (2001), 77, 263-295; Boyce et al., Journal of Experimental Medicine (2005), 201 (12), 1869-1873; and Snibson, et al., Journal of the British Society for Allergy and Clinical Immunology (2005), 35(2), 146-52. In addition to routine safety assessments of these target pairs specific tests for the degree of immunosuppression may be warranted and helpful in selecting the best target pairs (see Luster et al., Toxicology (1994), 92(1-3), 22943; Descotes, et al., Developments in biological standardization (1992), 77 99-102; Hart et al., Journal of Allergy and Clinical Immunology (2001), 108(2), 250-257).

Based on the rationale disclosed above and using the same evaluation model for efficacy and safety other pairs of targets that DVD-Ig molecules can bind and be useful to treat asthma may be determined. Preferably such targets include, but are not limited to, IL-13 and IL-1beta, since IL-1beta is also implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; and IL-13 and ADAM8. The present invention also provides DVD-Igs capable of binding one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase.

3. Rheumatoid Arthritis

Rheumatoid arthritis (RA), a systemic disease, is characterized by a chronic inflammatory reaction in the synovium of joints and is associated with degeneration of cartilage and erosion of juxta-articular bone. Many pro-inflammatory cytokines including TNF, chemokines, and growth factors are expressed in diseased joints. Systemic administration of anti-TNF antibody or sTNFR fusion protein to mouse models of RA was shown to be anti-inflammatory and joint protective. Clinical investigations in which the activity of TNF in RA patients was blocked with intravenously administered infliximab (Harriman G, Harper L K, Schaible T F. 1999 Summary of clinical trials in rheumatoid arthritis using infliximab, an anti-TNFalpha treatment. Ann Rheum Dis 58 Suppl 1:I61-4.), a chimeric anti-TNF monoclonal antibody (mAB), has provided evidence that TNF regulates IL-6, IL-8, MCP-1, and VEGF production, recruitment of immune and inflammatory cells into joints, angiogenesis, and reduction of blood levels of matrix metalloproteinases-1 and -3. A better understanding of the inflammatory pathway in rheumatoid arthritis has led to identification of other therapeutic targets involved in rheumatoid arthritis. Promising treatments such as interleukin-6 antagonists (MRA), CTLA4Ig (abatacept, Genovese Mc et al 2005 Abatacept for rheumatoid arthritis refractory to tumor necrosis factor alpha inhibition. N Engl J. Med. 353:1114-23.), and anti-B cell therapy (rituximab, Okamoto H, Kamatani N. 2004 Rituximab for rheumatoid arthritis. N Engl J. Med. 351:1909) have already been tested in randomized controlled trials over the past year. Other cytokines have been identified and have been shown to be of benefit in animal models, including interleukin-15, interleukin-17, and interleukin-18, and clinical trials of these agents are currently under way. Dual-specific antibody therapy, combining anti-TNF and another mediator, has great potential in enhancing clinical efficacy and/or patient coverage. For example, blocking both TNF and VEGF can potentially eradicate inflammation and angiogenesis, both of which are involved in pathophysiology of RA. Blocking other pairs of targets involved in RA including, but not limited to, TNF and IL-18; TNF and IL-12; TNF and IL-23; TNF and IL-1beta; TNF and MIF; TNF and IL-17; and TNF and IL-15 with specific DVD Igs is also contemplated. In addition to routine safety assessments of these target pairs, specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257). Whether a DVD Ig molecule will be useful for the treatment of rheumatoid arthritis can be assessed using pre-clinical animal RA models such as the collagen-induced arthritis mouse model. Other useful models are also well known in the art (see Brand DD., Comp Med. (2005) 55(2):114-22).

4. SLE

The immunopathogenic hallmark of SLE is the polyclonal B cell activation, which leads to hyperglobulinemia, autoantibody production and immune complex formation. The fundamental abnormality appears to be the failure of T cells to suppress the forbidden B cell clones due to generalized T cell dysregulation. In addition, B and T-cell interaction is facilitated by several cytokines such as IL-10 as well as co-stimulatory molecules such as CD40 and CD40L, B7 and CD28 and CTLA4, which initiate the second signal. These interactions together with impaired phagocytic clearance of immune complexes and apoptotic material, perpetuate the immune response with resultant tissue injury. The following targets may be involved in SLE and can potentially be used for DVD-Ig approach for therapeutic intervention: B cell targeted therapies: CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGS1, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, IL1R2, ITGA2, ITGA3, MS4A1, ST6GAL1, CD1C, CHST10, HLA-A, HLA-DRA, and NT5E.; co-stimulatory signals: CTLA4 or B7.1/B7.2; inhibition of B cell survival: BlyS, BAFF; Complement inactivation: C5; Cytokine modulation: the key principle is that the net biologic response in any tissue is the result of a balance between local levels of proinflammatory or anti-inflammatory cytokines (see Sfikakis P P et al 2005 Curr Opin Rheumatol 17:550-7). SLE is considered to be a Th-2 driven disease with documented elevations in serum IL-4, IL-6, IL-10. DVD Igs capable of binding one or more targets selected from the group consisting of IL-4, IL-6, IL-10, IFN-a, and TNF-a are also contemplated. Combination of targets discussed above will enhance therapeutic efficacy for SLE which can be tested in a number of lupus preclinical models (see Peng SL (2004) Methods Mol Med.; 102:227-72).

5. Multiple Sclerosis

Multiple sclerosis (MS) is a complex human autoimmune-type disease with a predominantly unknown etiology. Immunologic destruction of myelin basic protein (MBP) throughout the nervous system is the major pathology of multiple sclerosis. MS is a disease of complex pathologies, which involves infiltration by CD4+ and CD8+ T cells and of response within the central nervous system. Expression in the CNS of cytokines, reactive nitrogen species and costimulator molecules have all been described in MS. Of major consideration are immunological mechanisms that contribute to the development of autoimmunity. In particular, antigen expression, cytokine and leukocyte interactions, and regulatory T-cells, which help balance/modulate other T-cells such as Th1 and Th2 cells, are important areas for therapeutic target identification.

IL-12 is a proinflammatory cytokine that is produced by APC and promotes differentiation of Th1 effector cells. IL-12 is produced in the developing lesions of patients with MS as well as in EAE-affected animals. Previously it was shown that interference in IL-12 pathways effectively prevents EAE in rodents, and that in vivo neutralization of IL-12p40 using a anti-IL-12 mAb has beneficial effects in the myelin-induced EAE model in common marmosets.

TWEAK is a member of the TNF family, constitutively expressed in the central nervous system (CNS), with pro-inflammatory, proliferative or apoptotic effects depending upon cell types. Its receptor, Fn14, is expressed in CNS by endothelial cells, reactive astrocytes and neurons. TWEAK and Fn14 mRNA expression increased in spinal cord during experimental autoimmune encephalomyelitis (EAE). Anti-TWEAK antibody treatment in myelin oligodendrocyte glycoprotein (MOG) induced EAE in C57BL/6 mice resulted in a reduction of disease severity and leukocyte infiltration when mice were treated after the priming phase.

One aspect of the invention pertains to DVD Ig molecules capable of binding one or more, preferably two, targets selected from the group consisting of IL-12, TWEAK, IL-23, CXCL13, CD40, CD40L, IL-18, VEGF, VLA4, TNF, CD45RB, CD200, IFNgamma, GM-CSF, FGF, C5, CD52, and CCR2. A preferred embodiment includes a dual-specific anti-IL-12/TWEAK DVD Ig as a therapeutic agent beneficial for the treatment of MS. Several animal models for assessing the usefulness of the DVD molecules to treat MS are known in the art (see Steinman L, et al., (2005) Trends Immunol. 26(11):565-71; Lublin F D., et al., (1985) Springer Semin Immunopathol. 8(3): 197-208; Genain C P, et al., (1997) J Mol Med. 75(3):187-97; Tuohy V K, et al., (1999) J Exp Med. 189(7):1033-42; Owens T, et al., (1995) Neurol Clin.13(1): 51-73; and 't Hart B A, et al., (2005) J Immunol 175(7):4761-8. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Jones R. 2000 Rovelizumab (ICOS Corp). IDrugs. 3(4):442-6).

6. Sepsis

The pathophysiology of sepsis is initiated by the outer membrane components of both gram-negative organisms (lipopolysaccharide [LPS], lipid A, endotoxin) and gram-positive organisms (lipoteichoic acid, peptidoglycan). These outer membrane components are able to bind to the CD14 receptor on the surface of monocytes. By virtue of the recently described toll-like receptors, a signal is then transmitted to the cell, leading to the eventual production of the proinflammatory cytokines tumor necrosis factor-alpha (TNF-alpha) and interleukin-1 (IL-I). Overwhelming inflammatory and immune responses are essential features of septic shock and play a central part in the pathogenesis of tissue damage, multiple organ failure, and death induced by sepsis. Cytokines, especially tumor necrosis factor (TNF) and interleukin (IL)-1, have been shown to be critical mediators of septic shock. These cytokines have a direct toxic effect on tissues; they also activate phospholipase A2. These and other effects lead to increased concentrations of platelet-activating factor, promotion of nitric oxide synthase activity, promotion of tissue infiltration by neutrophils, and promotion of neutrophil activity.

The treatment of sepsis and septic shock remains a clinical conundrum, and recent prospective trials with biological response modifiers (i.e. anti-TNF, anti-MIF) aimed at the inflammatory response have shown only modest clinical benefit. Recently, interest has shifted toward therapies aimed at reversing the accompanying periods of immune suppression. Studies in experimental animals and critically ill patients have demonstrated that increased apoptosis of lymphoid organs and some parenchymal tissues contribute to this immune suppression, anergy, and organ system dysfunction. During sepsis syndromes, lymphocyte apoptosis can be triggered by the absence of IL-2 or by the release of glucocorticoids, granzymes, or the so-called 'death' cytokines: tumor necrosis factor alpha or Fas ligand. Apoptosis proceeds via auto-activation of cytosolic and/or mitochondrial caspases, which can be influenced by the pro- and anti-apoptotic members of the Bcl-2 family. In experimental animals, not only can treatment with inhibitors of apoptosis prevent lymphoid cell apoptosis; it may also improve outcome. Although clinical trials with anti-apoptotic agents remain distant due in large part to technical difficulties associated with their administration and tissue targeting, inhibition of lymphocyte apoptosis represents an attractive therapeutic target for the septic patient. Likewise, a dual-specific agent targeting both inflammatory mediator and a apoptotic mediator, may have added benefit. One aspect of the invention pertains to DVD Igs capable of binding one or more targets involved in sepsis, preferably two targets, selected from the group consisting TNF, 1-1, MIF, IL-6, IL-8, IL-18, IL-12, IL-23, FasL, LPS, Toll-like receptors, TLR-4, tissue factor, MIP-2, ADORA2A, CASP1, CASP4, IL10, IL1B, NFKB1, PROC, TNFRSF1A, CSF3, IL10, IL1B, IL6, ADORA2A, CCR3, IL10, IL1B, IL1RN, MIF, NFKB1, PTAFR, TLR2, TLR4, GPR44, HMOX1, midkine, IRAK1, NFKB2, SERPINA1, SERPINE1, and TREM1. The efficacy of such DVD Igs for sepsis can be assessed in preclinical animal models known in the art (see Buras J A, et al.,(2005) Nat Rev Drug Discov. 4(10):854-65 and Calandra T, et al., (2000) Nat Med. 6(2):164-70).

7. Neurological Disorders

7.1. Neurodegenerative Diseases

Chronic neurodegenerative diseases are usually age-dependent diseases characterized by progressive loss of neuronal functions (neuronal cell death, demyelination), loss of mobility and loss of memory. Emerging knowledge of the mechanisms underlying chronic neurodegenerative diseases (e.g. Alzheimer's disease) show a complex etiology and a variety of factors have been recognized to contribute to their development and progression e.g. age, glycemic status, amyloid production and multimerization, accumulation of advanced glycation-end products (AGE) which bind to their receptor RAGE (receptor for AGE), increased brain oxidative stress, decreased cerebral blood flow, neuroinflammation including release of inflammatory cytokines and chemokines, neuronal dysfunction and microglial activation. Thus these chronic neurodegenerative diseases represent a complex interaction between multiple cell types and mediators. Treatment strategies for such diseases are limited and mostly constitute either blocking inflammatory processes with non-specific anti-inflammatory agents (eg corticosteroids, COX inhibitors) or agents to prevent neuron loss and/or synaptic functions. These treatments fail to stop disease progression. Recent studies suggest that more targeted therapies such as antibodies to soluble A-b peptide (including the A-b oligomeric forms) can not only help stop disease progression but may help maintain memory as well. These preliminary observations suggest that specific therapies targeting more than one disease mediator (e.g. A-b and a pro-inflammatory cytokine such as TNF) may provide even better therapeutic efficacy for chronic neurodegenerative diseases than observed with targeting a single disease mechanism (e.g. soluble A-balone) (see C. E. Shepherd, et al, Neurobiol Aging. 2005 Oct. 24; Nelson R B., Curr Pharm Des. 2005; 11:3335; William L. Klein.; Neurochem Int. 2002 ; 41:345; Michelle C Janelsins, et al., J Neuroinflammation. 2005 ; 2:23; Soloman B., Curr Alzheimer Res. 2004; 1:149; Igor Klyubin, et al., Nat Med. 2005; 11:556-61; Arancio 0, et al., EMBO Journal (2004) 1-10; Bornemann K D, et al., Am J Pathol. 2001; 158:63; Deane R, et al., Nat Med. 2003; 9:907-13; and Eliezer Masliah, et al., Neuron. 2005; 46:857).

The DVD-Ig molecules of the invention can bind one or more targets involved in Chronic neurodegenerative diseases such as Alzheimers. Such targets include, but are not limited to, any mediator, soluble or cell surface, implicated in AD pathogenesis e.g AGE (S100 A, amphoterin), pro-inflammatory cytokines (e.g. IL-1), chemokines (e.g. MCP 1), molecules that inhibit nerve regeneration (e.g. Nogo, RGM A), molecules that enhance neurite growth (neurotrophins). The efficacy of DVD-Ig molecules can be validated in pre-clinical animal models such as the transgenic mice that over-express amyloid precursor protein or RAGE and develop Alzheimer's disease-like symptoms. In addition, DVD-Ig molecules can be constructed and tested for efficacy in the animal models and the best therapeutic DVD-Ig can be selected for testing in human patients. DVD-Ig molecules can also be employed for treatment of other neurodegenerative diseases such as Parkinson's disease. Alpha-Synuclein is involved in Parkinson's pathology. A DVD-Ig capable of targeting alpha-synuclein and inflammatory mediators such as TNF, IL-1, MCP-1 can prove effective therapy for Parkinson's disease and are contemplated in the invention.

7.2 Neuronal Regeneration and Spinal Cord Injury

Despite an increase in knowledge of the pathologic mechanisms, spinal cord injury (SCI) is still a devastating condition and represents a medical indication characterized by a high medical need. Most spinal cord injuries are contusion or compression injuries and the primary injury is usually followed by secondary injury mechanisms (inflammatory mediators e.g. cytokines and chemokines) that worsen the initial injury and result in significant enlargement of the lesion area, sometimes more than 10-fold. These primary and secondary mechanisms in SCI are very similar to those in brain injury caused by other means e.g. stroke. No satisfying treatment exists and high dose bolus injection of methylprednisolone (MP) is the only used therapy within a narrow time window of 8 h post injury. This treatment, however, is only intended to prevent secondary injury without causing any significant functional recovery. It is heavily criticized for the lack of unequivocal efficacy and severe adverse effects, like immunosuppression with subsequent infections and severe histopathological muscle alterations. No other drugs, biologics or small molecules, stimulating the endogenous regenerative potential are approved, but promising treatment principles and drug candidates have shown efficacy in animal models of SCI in recent years. To a large extent the lack of functional recovery in human SCI is caused by factors inhibiting neurite growth, at lesion sites, in scar tissue, in myelin as well as on injury-associated cells. Such factors are the myelin-associated proteins NogoA, OMgp and MAG, RGM A, the scar-associated CSPG (Chondroitin Sulfate Proteoglycans) and inhibitory factors on reactive astrocytes (some semaphorins and ephrins). However, at the lesion site not only growth inhibitory molecules are found but also neurite growth stimulating factors like neurotrophins, laminin, L1 and others. This ensemble of neurite growth inhibitory and growth promoting molecules may explain that blocking single factors, like NogoA or RGM A, resulted in significant functional recovery in rodent SCI models, because a reduction of the inhibitory influences could shift the balance from growth inhibition to growth promotion. However, recoveries observed with blocking a single neurite outgrowth inhibitory molecule were not complete. To achieve faster and more pronounced recoveries either blocking two neurite outgrowth inhibitory molecules e.g Nogo and RGM A, or blocking an neurite outgrowth inhibitory molecule and enhancing functions of a neurite outgrowth enhancing molecule e.g Nogo and neurotrophins, or blocking a neurite outgrowth inhibitory molecule e.g. Nogo and a pro-inflammatory molecule e.g. TNF, may be desirable (see McGee A W, et al., Trends Neurosci. 2003; 26: 193; Marco Domeniconi, et al., J Neurol Sci. 2005; 233:43; Milan Makwanal, et al., FEBS J. 2005; 272: 2628; Barry J. Dickson, Science. 2002; 298:1959; Felicia Yu Hsuan Teng, et al., J Neurosci Res. 2005; 79:273; Tara Karnezis, et al., Nature Neuroscience 2004; 7, 736; Gang Xu, et al., J. Neurochem.2004; 91; 1018).

In one aspect, DVD-Igs capable of binding target pairs such as NgR and RGM A; NogoA and RGM A; MAG and RGM A; OMGp and RGM A; RGM A and RGM B; CSPGs and RGM A; aggrecan, midkine, neurocan, versican, phosphacan, Te38 and TNF-a; Aβ globulomer-specific antibodies combined with antibodies promoting dendrite & axon sprouting are provided. Dendrite pathology is a very early sign of AD and it is known that NOGO A restricts dendrite growth. One can combine such type of ab with any of the SCI-candidate (myelin-proteins) Ab. Other DVD-Ig targets may include any combination of NgR-p75, NgR-Troy, NgR-Nogo66 (Nogo), NgR-Lingo, Lingo-Troy, Lingo-p75, MAG or Omgp. Additionally, targets may also include any mediator, soluble or cell surface, implicated in inhibition of neurite e.g Nogo, Ompg, MAG, RGM A, semaphorins, ephrins, soluble A-b, pro-inflammatory cytokines (e.g. IL-1), chemokines (e.g. MIP 1a), molecules that inhibit nerve regeneration. The efficacy of anti-nogo/anti-RGM A or similar DVD-Ig molecules can be validated in pre-clinical animal models of spinal cord injury. In addition, these DVD-Ig molecules can be constructed and tested for efficacy in the animal models and the best therapeutic DVD-Ig can be selected for testing in human patients. In addition, DVD-Ig molecules can be constructed that target two distinct ligand binding sites on a single receptor e.g. Nogo receptor which binds three ligand Nogo, Ompg, and MAG and RAGE that binds A-b and S100 A. Furthermore, neurite outgrowth inhibitors e.g. nogo and nogo receptor, also play a role in preventing nerve regeneration in immunological diseases like multiple sclerosis. Inhibition of nogo-nogo receptor interaction has been shown to enhance recovery in animal models of multiple sclerosis. Therefore, DVD-Ig molecules that can block the function of one immune mediator eg a cytokine like L-12 and a neurite outgrowth inhibitor molecule eg nogo or RGM may offer faster and greater efficacy than blocking either an immune or an neurite outgrowth inhibitor molecule alone.

8. Oncological Disorders

Monoclonal antibody therapy has emerged as an important therapeutic modality for cancer (von Mehren M, et al 2003 Monoclonal antibody therapy for cancer. Annu Rev Med.; 54:343-69). Antibodies may exert antitumor effects by inducing apoptosis, redirected cytotoxicity, interfering with ligand-receptor interactions, or preventing the expression of proteins that are critical to the neoplastic phenotype. In addition, antibodies can target components of the tumor microenvironment, perturbing vital structures such as the formation of tumor-associated vasculature. Antibodies can also target receptors whose ligands are growth factors, such as the epidermal growth factor receptor. The antibody thus inhibits natural ligands that stimulate cell growth from binding to targeted tumor cells. Alternatively, antibodies may induce an anti-idiotype network, complement-mediated cytotoxicity, or antibody-dependent cellular cytotoxicity (ADCC). The use of dual-specific antibody that targets two separate tumor mediators will likely give additional benefit compared to a mono-specific therapy. DVD Igs capable of binding the following pairs of targets to treat oncological disease are also contemplated: IGF1 and IGF2; IGF1/2 and Erb2B; VEGFR and EGFR; CD20 and CD3, CD138 and CD20, CD38 and CD20, CD38 & CD138, CD40 and CD20, CD138 and CD40, CD38 and CD40. Other target combinations include one or more members of the EGF/erb-2/erb-3 family. Other targets (one or more) involved in oncological diseases that DVD Igs may bind include, but are not limited to those selected from the group consisting of: CD52, CD20, CD19, CD3, CD4, CD8, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, EGF, FGF10, FGF18, FGF2, FGF4, FGF7, IGF1, IGF1R, IL2, VEGF, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NR0B1, NR0B2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6A1, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB21P, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33A1, SLC43A1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGF, VEGFC, ANGPTL3, BAI1, COL4A3, IL8, LAMA5, NRP1, NRP2, STAB1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL18A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p16INK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (NGF), NGFR, NME1 (NM23A), PGR, PLAU (uPA), PTEN, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase IIa), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, ID2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94).

IV. Pharmaceutical Composition

The invention also provides pharmaceutical compositions comprising a binding protein, of the invention and a pharmaceutically acceptable carrier. The pharmaceutical compositions comprising binding proteins of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more binding proteins of the invention. In another embodiment, the pharmaceutical composition comprises one or more binding proteins of the invention and one or more prophylactic or therapeutic agents other than binding proteins of the invention for treating a disorder. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The binding proteins of the invention can be incorporated into pharmaceutical compositions suitable for administration to a subject. Typically, the pharmaceutical composition comprises a binding protein of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, a binding protein of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as silastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than a binding protein of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912, 015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy &Oncology 39:179-189, Song et al., 1995, "Antibody Mediated Lung Targeting of Long-Circulating Emulsions," PDA Journal of Pharmaceutical Science &Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insulator may be formulated containing a powder mix of the compound and a suitable powder base such as lactose or starch. If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate) lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, a binding protein of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompasse administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The binding proteins of the invention can be incorporated into a pharmaceutical composition suitable for parenteral administration. Preferably, the antibody or antibody-portions will be prepared as an injectable solution containing 0.1-250 mg/ml binding protein. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the binding proteins of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, and US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The binding proteins of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, a binding protein of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a binding protein of the invention is coformulated with and/or coadministered with one or more additional therapeutic agents that are useful for treating disorders in which IL-12 activity is detrimental. For example, a binding protein of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, a binding protein is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences encoding a binding protein of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley &Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

The binding proteins of the invention are useful in treating various diseases wherein the targets that are recognized by the binding proteins are detrimental. Such diseases include, but are not limited to, rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, *chlamydia, yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium* intracellulare, *mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, , vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue. (see Peritt et al. PCT publication No. WO2002097048A2, Leonard et al., PCT publication No. WO9524918 A1, and Salfeld et al., PCT publication No. WO00/56772A1).

The binding proteins of the invention can be used to treat humans suffering from autoimmune diseases, in particular those associated with inflammation, including, rheumatoid arthritis, spondylitis, allergy, autoimmune diabetes, autoimmune uveitis.

Preferably, the binding proteins of the invention or antigen-binding portions thereof, are used to treat rheumatoid arthritis, Crohn's disease, multiple sclerosis, insulin dependent diabetes mellitus and psoriasis.

A binding protein of the invention also can be administered with one or more additional therapeutic agents useful in the treatment of various diseases.

A binding protein of the invention can be used alone or in combination to treat such diseases. It should be understood that the binding proteins can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Preferred combinations to treat autoimmune and inflammatory diseases are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the DVD Igs of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Binding proteins of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (PCT Publication No. WO 97/29131), CA2 (REMICADE® infliximab), CDP 571, and soluble p55 or p75 TNF receptors, derivatives, thereof, (p75TNFR1gG (ENBREL® etanercept) or p55TNFR1gG (lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination include key players of the autoimmune response which may act parallel to, dependent on or in concert with IL-12 function; especially preferred are IL-18 antagonists including IL-18 antibodies or soluble IL-18 receptors, or IL-18 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The binding proteins of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNF☐ or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (ENBREL® etanercept and p55TNFRIgG (lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Nonlimiting additional agents which can also be used in combination with a binding protein to treat rheumatoid arthritis include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., Arthritis & Rheumatism (1996) Vol. 39, No. 9 (supplement), S308); interleukin -17 inhibitors (see e.g., *Arthritis & Rheumatism* (1996) Vol. 39, No. 9 (supplement), S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents.

In one embodiment, the binding protein or antigen-binding portion thereof, is administered in combination with one of the following agents for the treatment of rheumatoid arthritis: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; B1RB-796; SCIO-469; VX-702; AMG-548; VX-740; Roflumilast; IC-485; CDC-801; and mesopram.

Non-limiting examples of therapeutic agents for inflammatory bowel disease with which a binding protein of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1R1, sIL-1R11, sIL-6R) and antiinflammatory cytokines (e.g. IL-4, IL-10, IL-11, IL-13 and TGFβ).

Preferred examples of therapeutic agents for Crohn's disease in which a binding protein can be combined include the following: TNF antagonists, for example, anti-TNF antibodies, D2E7 (PCT Publication No. WO 97/29131; HUMIRA® adalimumab), CA2 (REMICADE® infliximab), CDP 571, TNFR-Ig constructs, (p75TNFRIgG (ENBREL® etanercept) and p55TNFRIgG (lenercept)) inhibitors and PDE4 inhibitors. Antibodies of the invention, or antigen binding portions thereof, can be combined with corticosteroids, for example, budenoside and dexamethasone. Binding proteins of the invention or antigen binding portions thereof, may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. Antibodies of the invention or antigen binding portion thereof may also be used with T cell signaling inhibitors, for example, tyrosine kinase inhibitors 6-mercaptopurines. Binding proteins of the invention, or antigen binding portions thereof, can be combined with IL-11. Binding proteins of the invention, or antigen binding portions thereof, can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab and interferon-gamma.

Non-limiting examples of therapeutic agents for multiple sclerosis with which binding proteins of the invention can be combined include the following: corticosteroids; prednisolone; methylprednisolone; azathioprine; cyclophosphamide; cyclosporine; methotrexate; 4-aminopyridine;tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE® glatiramer acetate; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, and PDGF. Binding proteins of the invention can be combined with antibodies to cell surface molecules such as CD2, CD3, CD4, CD8, CD19, CD20, CD25, CD28, CD30, CD40, CD45, CD69, CD80, CD86, CD90 or their ligands. Binding proteins of the invention, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which binding proteins of the invention can be combined tinclude interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The binding proteins of the invention, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, ANTEGRAN® natalizumab-ELAN/Biogen), interferon gamma antagonists, IL-4 agonists.

Non-limiting examples of therapeutic agents for Angina with which binding proteins of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil hcl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate.

Non-limiting examples of therapeutic agents for Ankylosing Spondylitis with which binding proteins of the invention can be combined include the following: ibuprofen, diclofenac and misoprostol, naproxen, meloxicam, indomethacin, diclofenac, celecoxib, rofecoxib, Sulfasalazine, Methotrexate, azathioprine, minocyclin, prednisone, etanercept, infliximab.

Non-limiting examples of therapeutic agents for Asthma with which binding proteins of the invention can be combined include the following: albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which binding proteins of the invention can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol hcl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for HCV with which binding proteins of the invention can be combined include the following: Interferon-alpha-2a, Interferon-alpha-2b, Interferon-alpha con1, Interferon-alpha-n1, Pegylated interferon-alpha-2a, Pegylated interferon-alpha-2b, ribavirin, Peginterferon alfa-2b+ribavirin, Ursodeoxycholic Acid, Glycyrrhizic Acid, Thymalfasin, Maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for Idiopathic Pulmonary Fibrosis with which binding proteins of the invention can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone hcl, potassium chloride, triamcinolone acetonide, tacrolimus anhydrous, calcium, interferon-alpha, methotrexate, mycophenolate mofetil, Interferon-gamma-1β.

Non-limiting examples of therapeutic agents for Myocardial Infarction with which binding proteins of the invention can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide.

Non-limiting examples of therapeutic agents for Psoriasis with which binding proteins of the invention can be combined include the following: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Non-limiting examples of therapeutic agents for Psoriatic Arthritis with which binding proteins of the invention can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

Non-limiting examples of therapeutic agents for Restenosis with which binding proteins of the invention can be combined include the following: sirolimus, paclitaxel, everolimus, tacrolimus, ABT-578, acetaminophen.

Non-limiting examples of therapeutic agents for Sciatica with which binding proteins of the invention can be combined include the following: hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, temazepam.

Preferred examples of therapeutic agents for SLE (Lupus) in which binding proteins of the invention can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. Binding proteins of the invention, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. Binding proteins of the invention may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Binding proteins of the invention, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies of the invention or antigen binding portion thereof may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (PCT Publication No. WO 97/29131; HUMIRA® adalimumab), CA2 (REMICADE® infliximab), CDP 571, TNFR-Ig constructs, (p75TNFRIgG (ENBREL® etanercept) and p55TNFRIgG (lenercept)).

The pharmaceutical compositions of the invention may include a "therapeutically effective amount" or a "prophylactically effective amount" of a binding protein of the invention. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an binding protein of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Generation of Dual Variable Domain Immunoglobulin (DVD-Ig)

The dual variable domain immunoglobulin (DVD-Ig) molecule is designed such that two different light chain variable domains (VL) from the two different parent mAbs are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region (FIG. 1A).

Example 1.1

Generation of Murine Monoclonal Antibodies to IL-1α and IL-1β

Monoclonal Antibodies to IL-1α and IL-1β were generated as follows using Hybridoma technology well known in the art.

Example 1.1.A

Immunization of Mice

Purified recombinant human IL-1α and murine IL-1β (R&D Systems) were used as immunogens as well as coating antigens in titer assays and screening ELISA. Immunizing dosages ranged from 5.0 to 20.0 μg/mouse/injection for all antigens for both primary and boost immunizations. IMMUNEASY™ adjuvant was purchased from Qiagen (Waltham, Mass.) and used at Adjuvant/antigen ratio of 20 ml IMMUNEASY™ adjuvant per 10.0 μg antigen. Each group of animals to be immunized contained 5 IL-1αβ KO mice obtained from Dr. Yoichiro Iwakura (University of Tokyo, Minato-ku, Tokyo, Japan). The mice were immunized according to dosing schedule described below. MRC-5 cells were purchased from ATCC (Manassas, Va.) and used for IL-1 bioassay. Human IL-8 ELISA kits and control mouse anti-hIL-1α and β antibodies (MAB200 and MAB201) were purchased from R&D Systems (Minneapolis, Minn.).

Briefly, adjuvant-antigen mixture was prepared by first gently mixing the adjuvant in a vial using a vortex. The desired amount of adjuvant was removed from the vial and put into an autoclaved 1.5 mL microcentrifuge tube. The antigen was prepared in PBS or saline with concentration ranging from 0.5-1.0 mg/ml. The calculated amount of antigen was then added to the microcentrifuge tube with the adjuvant and the solution was mixed by gently pipetting up and down 5 times. The adjuvant-antigen mixture was incubated at room temperature for 15 min and then mixed again by gently pipetting up and down 5 times. The adjuvant-antigen solution was drawn into the proper syringe for animal injection. A total of 5-20 μg of antigen was injected in a volume of 50-100 μl. Each animal was immunized, and then boosted 2 to 3 times depending on the titer. Animals with good titers were given a final intravenous boost before fusion and generation of hybridomas.

Example 1.1.B

Screening Hybridomas

Hybridomas, generated as described above, were screened and antibody titer determined using ELISA: Protein antigens were directly coated on ELISA plates for detecting the specific antibodies using standard ELISA procedures. Briefly, ELISA plates were coated with 100 μl of either rhIL-1α or rhIL-1β (1.0 μg/ml in PBS) overnight at 4° C. Plates were washed 3 times with 250 μl PBS/0.5% TWEEN®20 polyethylene-sorbitan monolaurate and blocked with 200 μl blocking buffer (2% BSA in PBS with 0.5% TWEEN®20) polyethylene-sorbitan monolaurate). Diluted sera or hybridoma supernatant (100 μl) was added to each well, and incubated at room temperature for 2 hrs. Plates were then washed 3 times with PBS/0.5% TWEEN®20polyethylene-sorbitan monolaurate, HRP-goat anti-murine IgG was used for detection, and binding ODs were observed at 450 nm. Hybridoma clones producing antibodies that showed high specific binding activity in the ELISA were subcloned and purified, and affinity (Biacore) and potency (MRC-5 bioassay) of the antibodies were characterized as follows.

Example 1.1.C

Characterization of Murine Monoclonal Antibodies to IL-1α and IL-1β

The following assays were used to characterize the antibodies produced by the hybridomas described in example 1.1.B.

Example 1.1.C.1

Surface Plasmon Resonance

Real-time binding interactions between captured antibody (mouse anti-rmIL1 antibody captured on a biosensor matrix via goat anti-mouse IgG) and rmIL-1 were measured by surface plasmon resonance (SPR) using the BIAcore system (Biacore AB, Uppsala, Sweden) according to manufacturer's instructions and standard procedures. Briefly, rmIL-1 was diluted in HBS running buffer (Biacore AB) and 50 μl aliquots were injected through the immobilized protein matrices at a flow rate of 5 ml/min. The concentrations of rhIL1 employed were 62.5, 125, 187.5, 250, 375, 500, 750, 1000, 1500 and 2000 nM. To determine the dissociation constant (off-rate), association constant (on-rate), BIAcore kinetic evaluation software (version 3.1) was used.

Example 1.1.C.2

Anti-IL-1 Bioassay

The MRC-5 cell line is a human lung fibroblast cell line that produces IL-8 in response to human IL-1α and IL-1β in a dose-dependent manner (see Dinarello, C. A., K. Muegge, and S. K. Durum. 2000. Current Protocols in Immunology 6:1). MRC-5 cells were cultured in 10% FBS complete MEM and grown at 37° C. in a 5% $CO_2$ incubator. To determine neutralizing potencies of the mAbs against recombinant human IL-1αor IL-1β, different concentrations (0-10 μg/ml) of mAb (50 μl) was added to a 96-well plate and pre-incubated with 501 μl of rhIL-1αor rhIL-1b (10-50 μg/ml) for 1 hr at 37° C. The supernatants were harvested, diluted, and IL-8 concentrations measured by ELISA using a standard IL-8 ELISA kit (R&D Systems). Antibody potency was determined by its ability to inhibit IL-8 production by MRC-5 cells.

Based on Biacore and MRC-5 bioassay, a number of murine anti-hIL-1 and anti-hIL-1b antibodies with high affinity and potency were identified, as shown in Table 1 below:

TABLE 1

Generation and characterization of murine anti-hIL-1a/b mAbs.

| mAb Clone# | Specificity | $K_D$ (M) | $IC_{50}$ (M) |
| --- | --- | --- | --- |
| 3D12.E3 | hIL-1α | 1.11E−09 | 6.70E−10 |
| 18F4.2C8 | hIL-1α | 5.78E−10 | 8.90E−11 |
| 6H3.1A4.3E11 | hIL-1α | 3.54E−10 | 2.40E−10 |
| 13F5.G5 | hIL-1β | 2.91E−10 | 6.00E−10 |
| 1B12.4H4 | hIL-1β | 2.13E−10 | 5.30E−10 |
| 6B12.4F6 | hIL-1β | 5.54E−10 | 3.20E−10 |

Example 1.1.D

Cloning and Sequencing of the Murine Monoclonal Antibodies to IL-1α and IL-1β:

Cloning and sequencing of the variable heavy (VH) and light (VL) genes of all anti-IL-1a/b mAbs described in Table 1 and additional antibodies were carried out after isolation and purification of the total RNA from the each hybridoma cell line using TRIZOL® reagent (Invitrogen) according to the manufacturer's instructions. Amplification of both VH and VL genes was carried out using the IgGVH and Ig?VL oligonucleotides from the Mouse Ig-Primer Set (Novagen, Madison, Wis.) with One-tube RT-PCR kit (Qiagen) as suggested by the manufacturer. DNA fragments resulting from productive amplifications were cloned into pCR-TOPO® vector (Invitrogen) according to the manufacturer's instructions. Multiple VH and VL clones were then sequenced by the dideoxy chain termination method using an ABI 3000 sequencer (Applied Biosystems, Foster City, Calif.). The sequences of all mAb VL and VH genes are shown below in Table 2.

TABLE 2

Murine monoclonal antibodies capable of binding human IL-1α or IL-1β

| Protein | Sequence Identifier | Sequence 12345678901234567890 |
|---|---|---|
| VH 3D12.E3 | SEQ ID NO.:1 | QIQLVQSGPELKKPGETVKI SCKASGYTFRNYGMNWVKQA PGKDLKRMAWINTYTGESTY ADDFKGRFAFSLETSASTAY LQINNLKNEDTATYFCARGI YYYCSSYAMDYWGQGTSVTV SS |
| VL 3D12.E3 | SEQ ID NO.:2 | NIQMTQTTSSLSASLGDRVT ISCRASQDISNCLNWYQQKP DGTVKLLIYYTSRLHSGVPS RFSGSGSGTDYSLTISNLEQ EDIATYFCQQGKTLPYAFGG GTKLEINR |
| VH 18F4.2C8 | SEQ ID NO.:3 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| VL 18F4.2C8 | SEQ ID NO.:4 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| VH 6H3.1A4.3E11 | SEQ ID NO.:5 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| VL 6H3.1A4.3E11 | SEQ ID NO.:6 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| VH 13F5.G5 | SEQ ID NO.:7 | QVQLQQSGAELVRPGSSVKI SCKASGYAFSSYWHNWVKQR PGQGLEWIGQIYPGDGDTNY NGKFKGKATLTADKSSSTSY MQLSGLTSEDSAMYFCVRFP TGNDYYAMDYWGQGTSVTVS S |
| VL 13F5.G5 | SEQ ID NO.:8 | NIVLTQSPASLAVSLGQRAT ISCRASESVDSYGNSYMHWY QQKPGQPPKLLIYLASNLES GVPARFSGSGSRTDFTLTID PVEADDAATYYCQQNNEDPF TFGSGTKLEIKR |
| VH 1B12.4H4 | SEQ ID NO.:9 | QVHLKESGPGLVAPSQSLSI TCTVSGFSLTDYGVSWIRQP PGKGLEWLGLIWGGGDTYYN SPLKSRLSIRKDNSKSQVFL KNNSLQTDDTAVYYCAKQRT LWGYDLYGHDYWGQGTSVTV SS |
| VL 1B12.4H4 | SEQ ID NO.:10 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| VH 6B12.4F6 | SEQ ID NO.:11 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| VL 6B12.4F6 | SEQ ID NO.:12 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |

Example 1.2

Generation and Characterization of Murine-human Chimeric Antibodies

All mAbs described above were converted to chimeric (with human constant region) and expressed, purified, and characterized to confirm activity and will be used as controls for subsequent DVD-Ig analysis. To convert 3D12.E3 into chimeric form, 3D12.E3-VL was PCR amplified using primers P1 and P2; meanwhile human Ck gene (in pBOS vector generated in-house at ABC) was amplified using primers P3 and P4. Both PCR reactions were performed according to standard PCR techniques and procedures. The two PCR products were gel-purified, and used together as overlapping template for the subsequent overlapping PCR reaction using primers P1 and P4 using standard PCR conditions. The final PCR product, the chimeric light chain 3D12.E3-VL-hCk, was subcloned into pEF6 TOPO® mammalian expression vector (Invitrogen) by TOPO® cloning according to the manufacturer's instructions. Table 3 shows the PCR primers' sequences:

TABLE 3

| | | |
|---|---|---|
| P1: | 5' ATG GTG TCC ACA GCT CAG TTC C 3' | SEQ ID NO. 13 |
| P2: | 5' GC AGC CAC CGT ACG CCG GTT TAT TTC CAG 3' | SEQ ID NO. 14 |
| P3: | 5' CGT ACG GTG GCT GCA CCA TCT GTC 3' | SEQ ID NO. 15 |
| P4: | 5' TCA ACA CTC TCC CCT GTT GAA GC 3' | SEQ ID NO. 16 |

To convert 3D12.E3 heavy chain into chimeric form, 3D12.E3-VH was PCR amplified using primers P5 and P6; meanwhile human Cγ1 gene (in pBOS vector generated in-house at ABC) was amplified using primers P7 and P8. Both PCR reactions were performed according to standard PCR techniques and procedures. The two PCR products were gel-purified, and used together as overlapping template for the subsequent overlapping PCR reaction using primers P5 and P8 using standard PCR conditions. The final PCR product, the chimeric light chain 3D12.E3-VH-hCγ1, was subcloned into pcDNA3.1 TOPO® mammalian expression vector (Invitrogen) according to the manufacturer's instructions. Table 4 shows the PCR primers' sequences:

TABLE 4

| | | |
|---|---|---|
| P5: | 5' ATG GCT TGG GTG TGG ACC TTG C 3' | SEQ ID NO. 17 |
| P6: | 5' GGG CCC TTG GTC GAC GCT GAG GAG ACG GTG ACT GAG G 3' | SEQ ID NO. 18 |
| P7: | 5' GCG TCG ACC AAG GGC CCA TCG GTC TTC C 3' | SEQ ID NO. 19 |
| P8: | 5' TC ATT TAC CCG GAG ACA GGG AGA GGC 3' | SEQ ID NO. 20 |

Similarly, chimeric 13F5.G5-VH-Cγ1 was generated using primers P21/P22 (for VH) and P7/P8 (for hCγ1) and cloned into pcDNA3.1 TOPO® vecter, and chimeric 13F5.G5-VL-Cκ was generated using primers P23/P24 (for VL) and P3/P4 (for hCk) and cloned into pEF6 TOPO® vector. Table 5 shows the PCR primers' sequences:

TABLE 5

| | | |
|---|---|---|
| P21 | 5' ATA GAA TGG AGC TGG GTT TTC CTC 3' | SEQ ID NO. 21 |
| P22 | 5' GGG CCC TTG GTC GAC GC TGA GGA GAC GGT GAC TGA 3' | SEQ ID NO. 22 |
| P23 | 5' ATG GTC CTC ATG TCC TTG CTG TTC 3' | SEQ ID NO. 23 |
| P24 | 5' GC AGC CAC CGT ACG CCG TTT TAT TTC CAG CTT TG 3' | SEQ ID NO. 24 |

To express chimeric Abs, 13F5.G5-VL-Cκ and 13F5.G5-VH-Cγ1 were co-expressed in COS using LIPOFECTAMINE™ transfection reagent (Invitrogen) for 72 hr, and the medium collected and IgG purified by Protein A chromatography. Similarly, 13F5.G5-VL-Cκ and 13F5.G5-VH-Cγ1 were co-expressed in COS using LIPOFECTAMINE™ transfection reagent (Invitrogen) for 72 hr, and the medium collected and IgG purified by Protein A chromatography. Both purified chimeric Abs were characterized by Biacore and MRC-5 bioassay to confirm activity. The results showed that these chimeric Abs displayed similar affinity and potency to that of the original murine mAbs.

Example 1.3

Construction, Expression, and Purification of IL-1α/β Dual Variable Domain Immunoglobulin (DVD-Ig)

The construct used to generate DVD-Ig capable of binding hIL-1α and hIL-1β is illustrated in FIG. 1B. Briefly, parent mAbs including two high affinity murine Abs, anti-hIL-1α (clone 3D12.E3) and anti-hIL-1β (clone 13F5.G5), were obtained by immunizing Balb/c mice with recombinant IL-1α protein (rhIL-1α) and recombinant IL-1β protein (rhIL-1β), respectively. The VL/VH genes of these two hybridoma clones were isolated by RT-PCR using the mouse Ig Primer Kit (Novagen, Madison, Wis.). The VL/VH genes were first converted into chimeric antibodies (with human constant regions) to confirm activity and potency. To generate DVD1-Ig, the VH and VL of 13F5.G5 was directly fused to the N-terminus of the VH and VL of 3D12.E3, respectively (as shown in FIG.1B). The DVD2-Ig was constructed similarly, except that it had a linker between the two variable domains in both the light chain (the linker sequence is ADAAP) and the heavy chain (the linker sequence is AKTTPP). These sequences were selected from the N-termini of murine Cκ and CH1 sequences. These linker sequences, selected from the N-termini of murine Cκ and CH1, are natural extension of the variable domains and exhibit a flexible conformation without significant secondary structures based on the analysis of several Fab crystal structures. The detailed procedures of the PCR cloning is described below:

Example 1.3.A

Molecular Cloning of hIL-1a/bDVD1-Ig

13F5.G5-VH was PCR amplified using primers P21 and P25; meanwhile 3D12.E3-VH-hCγ1 was amplified using primers P14 and P8. Both PCR reactions were performed according to standard PCR techniques and procedures. The two PCR products were gel-purified, and used together as overlapping template for the subsequent overlapping PCR reaction using primers P21 and P8 using standard PCR conditions. The final PCR product, the DVD1-Ig heavy chain hIL-1a/bDVD1-VH-hCγ1, was subcloned into pcDNA3.1 TOPO® mammalian expression vector (Invitrogen) according to the manufacturer's instructions. Table 6 shows the PCR primers' sequences:

TABLE 6

| | | |
|---|---|---|
| P14: | 5' CAG ATC CAG TTG GTG CAG TCT GG 3' | SEQ ID NO. 25 |
| P25: | 5' CAC CAA CTG GAT CTG TGA GGA GAC GGT GAC TGA GG 3' | SEQ ID NO. 26 |

To generate hIL-1a/bDVD1-Ig light chain, 13F5.G5-VL was PCR amplified using primers P23 and P26; meanwhile 3D12.E3-VL-hCκ was amplified using primers P16 and P4. Both PCR reactions were performed according to standard PCR techniques and procedures. The two PCR products were gel-purified, and used together as overlapping template for the subsequent overlapping PCR reaction using primers P23 and P4 using standard PCR conditions. The final PCR product, the hIL-1a/bDVD1-Ig light chain hIL-1a/bDVD1-VL-hCκ, was subcloned into pEF6 TOPO® mammalian expression vector (Invitrogen) according to the manufacturer's instructions. Table 7 shows the PCR primers' sequences:

TABLE 7

| | | |
|---|---|---|
| P16: | 5' AAT ATC CAG ATG ACA CAG ACT ACA TCC 3' | SEQ ID NO. 27 |
| P26: | 5' GTGT CAT CTG GAT ATT CCG TTT TAT TTC CAG CTT TG 3' | SEQ ID NO. 28 |

Example 1.3.B

Molecular Cloning of hIL-1a/bDVD2-Ig

13F5.G5-VH was PCR amplified using primers P21 and P17; meanwhile 3D12.E3-VH-hCγ1 was amplified using primers P18 and P8. Both PCR reactions were performed according to standard PCR techniques and procedures. The two PCR products were gel-purified, and used together as overlapping template for the subsequent overlapping PCR reaction using primers P21 and P8 using standard PCR conditions. The final PCR product, the DVD2-Ig heavy chain hIL-1a/bDVD2-VH-hCγ1, was subcloned into pcDNA3.1 TOPO® mammalian expression vector (Invitrogen) according to the manufacturer's instructions. Table 8 shows the PCR primers' sequences:

TABLE 8

| | | |
|---|---|---|
| P17: | 5' TGG GGG TGT CGT TTT GGC TGA GG 3' | SEQ ID NO. 29 |
| P18: | 5' GCC AAA ACG ACA CCC CCA CAG ATC CAG TTG GTG CAG 3' | SEQ ID NO. 30 |

To generate hIL-1a/bDVD2-Ig light chain, 13F5.G5-VL was PCR amplified using primers P23 and P19; meanwhile 3D12.E3-VL-hCκ was amplified using primers P20 and P4. Both PCR reactions were performed according to standard PCR techniques and procedures. The two PCR products were gel-purified, and used together as overlapping template for the subsequent overlapping PCR reaction using primers P23 and P4 using standard PCR conditions. The final PCR product, the hIL-1a/bDVD2-Ig light chain hIL-1a/bDVD2-VL-hCκ, was subcloned into pEF6 TOPO® mammalian expression vector (Invitrogen) according to the manufacturer's instructions. Table 9 shows the PCR primers' sequences:

TABLE 9

| | | |
|---|---|---|
| P19: | 5' TGG TGC AGC ATC AGC CCG TTT TAT TTC 3' | SEQ ID NO. 31 |
| P20: | 5' GCT GAT GCT GCA CCA AAT ATC CAG ATG ACA CAG 3' | SEQ ID NO. 32 |

The final sequences of hIL-1a/bDVD1-Ig and hIL-1a/bDVD2-Ig are described in Table 10:

TABLE 10

Amino acid sequence of hIL-1α/βDVD1-Ig and hIL-1α/βDVD2-Ig

| Protein Protein region | Sequence Identifier | Sequence 12345678901234567890 |
|---|---|---|
| DVD HEAVY VARIABLE hIL-1a/bDVD1-Ig | SEQ ID NO.:33 | QVQLQQSGAELVRPGSSVKI SCKASGYAFSSYWMNWVKQR PGQGLEWIGQIYPGDGDTNY NGKFKGKATLTADKSSSTSY MQLSGLTSEDSAMYFCVRFP TGNDYYAMDYWGQGTSVTVS SQIQLVQSGPELKKPGETVK ISCKASGYTFRNYGMNWVKQ APGKDLKRMAWINTYTGEST YADDFKGRFAFSLETSASTA YLQINNLKNEDTATYFCARG IYYYGSSYANDYWGQGTSVT VSS |
| VH 13F5.G5 | SEQ ID NO.:7 | QVQLQQSGAELVRPGSSVKI SCKASGYAFSSYWMNWVKQR PGQGLEWIGQIYPGDGDTNY NGKFKGKATLTADKSSSTSY MQLSGLTSEDSAMYFCVRFP TGNDYYAMDYWGQGTSVTVS S |
| Linker | | None |
| 3D12.E3 VH | SEQ ID NO.:1 | QIQLVQSGPELKKPGETVKI SCKASGYTFRNYGMNWVKQA PGKDLKRNAWTNTYTGESTY ADDFKGRFAFSLETSASTAY LQINNLKNEDTATYFCARGI YYYGSSYANDYWGQGTSVTV SS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDCSFFLYSKLTVDKSRW QQGNVFSCSVMHEALHNHYT QKSLSLSPGK |
| DVD LIGHT VARIABLE hIL-1a/bDVD1-Ig | SEQ ID NO.:35 | NIVLTQSPASLAVSLGQRAT ISCRASESVDSYGNSYMHWY QQKPGQPPKLLIYLASNLES GVPARFSGSGSRTDFTLTID PVEADDAATYYCQQNEDPF TFGSGTKLEIKRNIQMTQTT SSLSASLGDRVTISCRASQD ISNCLNWYQQKPDGTVKLLI YYTSRLHSGVPSRFSGSGSG TDYSLTISNLEQEDIATYFC QQGKTLPYAFGGGTKLEINR R |
| 13F5.G5 VL | SEQ ID NO.:8 | NIVLTQSPASLAVSLGQRAT ISCRASESVDSYGNSYMHWY QQKPGQPPKLLIYLASNLES GVPARFSGSGSRTDFTLTID PVEADDAATYYCQQNEDPF TFGSGTKLEIKR |

TABLE 10-continued

Amino acid sequence of hIL-1α/βDVD1-Ig and hIL-1α/βDVD2-Ig

| Protein Protein region | Sequence Identifier | Sequence 12345678901234567890 |
|---|---|---|
| Linker | | None |
| 3D12.E3 VL | SEQ ID NO.:2 | NIQMTQTTSSLSASLGDRVT ISCRASQDISNCLNWYQQKP DGTVKLLIYYTSRLHSGVPS RFSGSGSGTDYSLTISNLEQ EDIATYFCQQGKTLPYAFGG GTKLEINR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE hIL-1a/bDVD2-Ig | SEQ ID NO.:37 | QVQLQQSGAELVRPGSSVKI SCKASGYAFSSYWMNWVKQR PGQGLEWICQIYPGDGDTNY NGKFKGKATLTADKSSSTSY MQLSGLTSEDSAMYFCVRFP TGNDYYAMDYWGQGTSVTVS SAKTTPPQIQLVQSGPELKK PGETVKISCKASGYTFRNYG MNWVKQAPGKDLKRMAWINT YTGESTYADDFKGRFAFSLE TSASTAYLQINNLKNEDTAT YFCARGIYYYGSSYAMDYWG QGTSVTVSS |
| 13F5.G5 VH | SEQ ID NO.:7 | QVQLQQSGAELVRPGSSVKI SCKASGYAFSSYWMNWVKQR PGQGLEWIGQIYPGDGDTNY NGKFKGKATLTADKSSSTSY MQLSGLTSEDSAMYFCVRFP TGNDYYAMDYWGQGTSVTVS S |
| Linker | SEQ ID NO.:38 | AKTTPP |
| 3D12.E3 VH | SEQ ID NO.:1 | QIQLVQSGPELKKPGETVKI SCKASGYTFPNYGMNWVKQA PGKDLKRMAWTNTYTGESTY ADDFKGRFAFSLETSASTAY LQINNLKNEDTATYFCARGI YYYGSSYAMDYWGQGTSVTV SS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE HIL-1a/bDVD2-Ig | SEQ ID NO.:39 | NIVLTQSPASLAVSLGQRAT ISCPASESVDSYGNSYMHWY QQKPGQPPKLLIYLASNLES GVPARFSGSGSRTDFTLTID PVEADDAATYYCQQNNEDPF TFGSGTKLEIKRADAAPNIQ MTQTTSSLSASLGDRVTISC RASQDISNCLNWYQQKPDGT VKLLIYYTSRLHSGVPSRFS GSGSGTDYSLTISNLEQEDI ATYFCQQGKTLPYAFGGGTK LEINR |
| 13F5.G5 VL | SEQ ID NO.:8 | NIVLTQSPASLAVSLGQRAT ISCRASESVDSYGNSYMHWY QQKPGQPPKLLIYLASNLES GVPARFSGSGSRTDFTLTID PVEADDAATYYCQQNNEDPF TFGSGTKLEIKR |
| Linker | SEQ ID NO.:40 | ADAAP |
| 3D12.E3 VL | SEQ ID NO.:2 | NIQMTQTTSSLSASLGDRVT ISCRASQDISNCLNWYQQKP DGTVKLLIYYTSRLHSGVPS RFSGSGSGTDYSLTISNLEQ EDIATYFCQQGKTLPYAFGG GTKLEINR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |

Example 1.3.C

Expression and Purification of hIL-1a/bDVD1-Igs

The heavy and light chain of each construct was subcloned into pcDNA3.1 TOPO® and pEF6 TOPO® vectors (Invitrogen Inc.), respectively, and sequenced to ensure accuracy. The plasmids encoding the heavy and light chains of each construct were transiently expressed using Lipofectamine 2000 and 293 fectin reagents, respectively in COS cells as well as human embryonic kidney 293 cells (American Type Culture Collection, Manassas, Va.). The cell culture media was harvested 72 hr-post transient transfection and antibodies purified using protein A chromatography (Pierce, Rockford, Ill.) according to manufacturer's instructions. The Abs were analyzed by SDS-PAGE and quantitated by A280 and BCA (Pierce, Rockford, Ill.). Table 11 shows that the expression levels of hIL-1a/bDVD1-Ig and hIL-1a/bDVD2-Ig are comparable to that of the chimeric Abs, indicating that the DVD-Ig can be expressed efficiently in mammalian cells.

TABLE 11

Expression and molecular weight analysis of hIL-1a/bDVD-Ig

| | Expression level (ng/ml) | | Molecular mass (Dalton) | | |
|---|---|---|---|---|---|
| | COS | Freestyle 293 | Light Chain | Heavy Chain | Full length |
| Mock | 0 | 0 | | | |
| 3D12.E3-Ch | 2788 | 3886 | 23,696 | 49,914 | 147,220 |
| 13F5.G5-CH | 3260 | 3562 | 24,084 | 49,518 | 147,204 |

TABLE 11-continued

Expression and molecular weight analysis of hIL-1a/bDVD-Ig

|  | Expression level (ng/ml) | | Molecular mass (Dalton) | | |
|---|---|---|---|---|---|
|  | COS | Freestyle 293 | Light Chain | Heavy Chain | Full lengtn |
| DVD1-Ig | 2988 | 3300 | 35,797 (35,790) | 64,380 (64,371) | 200,346 (200,521) |
| DVD2-Ig | 2433 | 3486 | 36,222 (36,220) | 64,976 (64,973) | 202,354 (202,573) |

The molecular mass of the light chain, heavy chain, and full length of DVD1-Ig and DVD2-Ig determined experimentally by mass spectrometry are shown in parenthesis.

Example 1.4

Mass Spectrometry and SEC Analysis of hIL-1a/b DVD-Ig

For measuring molecular weight (MW) of light and heavy chains of DVD-Ig, 10 uL of DVD-Ig (0.8 ug/uL) was reduced by 1.0 M DTT solution (5 uL). A PLRP-S, 8 u, 4000 A, and 1×150 mm protein column (Michrom BioResource, Auburn, Mass.) was used to separate heavy and light chains of DVD-Ig. Agilent HP1100 Capillary HPLC (Agilent Technologies Inc., Pala Alto, Calif.) was used with the mass spectrometer QSTAR® (Applied Biosystems, Foster City, Calif.). The valco valve was set at 10 minutes to switch the flow from waste to MS for desalting sample. Buffer A was 0.02% TFA, 0.08% FA, 0.1% ACN and 99.8% HPLC-H2O. Buffer B contained 0.02% TFA, 0.08% FA, 0.1% HPLC-H2O, and 99.8% ACN. The HPLC flow rate was 50 uL/min, and the sample injection volume was 8.0 mL. The temperature of the column oven was set at 60° C., and separation gradient was: 5% B for 5 minutes; 5% B to 65% B for 35 minutes; 65% B to 95% B for another 5 minutes, and 95% B to 5% B for 5 minutes. TOFMS scan was from 800 to 2500 amu, and cycles were 3600. To determine the MW of full length DVD-Ig, a Protein MICROTRAP™ cartridge (Michrom BioResource, Auburn, Mass.) was used for desalting the sample. The HPLC gradient was: 5% B for 5 minutes; 5% B to 95% B in 1 minutes; and from 95% B to 5% B in another 4 minutes. The QSTAR TOFMS scan was from 2000 to 3500 amu, and cycles were 899. All MS raw data were analyzed using the Analyst QS software (Applied Biosystems). For SEC analysis of the DVD-Ig, purified DVD-Ig and chimeric Abs, in PBS, were applied on a Superose 6 10/300 G2, 300×10 mm column (Amersham Bioscience, Piscataway, N.J.). An HPLC instrument, Model 10A (Shimadzu, Columbia, Md.) was used for SEC. All proteins were determined using UV detection at 280 nm and 214 nm. The elution was isocratic at a flow rate of 0.5 mL/min. For stability study, samples in the concentration range of 0.2-0.4 mg/ml in PBS underwent 3 freeze-thaw cycles between −80° C. and 25° C., or were incubated at 4° C., 25° C., or 40° C., for 4 weeks and 8 weeks, followed by SEC analysis.

DVD-Ig and chimeric Abs were purified by protein A chromatography. The purification yield (3-5 mg/L) was consistent with hIgG quantification of the expression medium for each protein. The composition and purity of the purified DVD-Igs and chimeric Abs were analyzed by SDS-PAGE in both reduced and non-reduced conditions. In non-reduced condition, each of the four proteins migrated as a single band. The DVD-Ig proteins showed larger M.W. than the chimeric Abs, as expected. In non-reducing condition, each of the four proteins yielded two bands, one heavy chain and one light chain. Again, the heavy and light chains of the DVD-Igs were larger in size than that of the chimeric Abs. The SDS-PAGE showed that each DVD-Ig is expressed as a single species, and the heavy and light chains are efficiently paired to form an IgG-like molecule. The sizes of the heavy and light chains as well as the full-length protein of two DVD-Ig molecules are consistent with their calculated molecular mass based on amino acid sequences (see Table 11).

In order to determine the precise molecular weight of DVD-Ig, mass spectrometry was employed. As shown in Table I, the experimentally determined molecular mass of each DVD-Ig, including the light chain, heavy chain, and the full-length protein, is in good agreement with the predicted value. To further study the physical properties of DVD-Ig in solution, size exclusion chromatography (SEC) was used to analyze each protein. Both chimeric Abs and DVD2-Ig exhibited a single peak, demonstrating physical homogeneity as monomeric proteins. The 3D12.E3 chimeric Ab showed a smaller physical size then 13F5.G5 chimeric Ab, indicating that 3D12.E3 chimeric Ab adopted a more compact, globular shape. DVD1-Ig revealed a major peak as well as a shoulder peak on the right, suggesting that a portion of DVD1-Ig is possibly in an aggregated form in current buffer condition.

Example 1.5

Analysis of in vitro Stability of hIL-1a/b DVD-Igs

The physical stability of DVD-Ig was tested as follows. Purified antibodies in the concentration range of 0.2-0.4 mg/ml in PBS underwent 3 freeze-thaw cycles between −80° C. and 25° C., or were incubated at 4° C., 25° C., or 40° C., for 4 weeks and 8 weeks, followed by analysis using size exclusion chromatography (SEC) analysis (see Table 12).

TABLE 12 in vitro stability analysis of hIL-1a/b DVD-Ig by SEC

|  | 3D12.E3-Ch | | | 13F5.G5-Ch | | | DVD1-Ig | | | DVD2-Ig | | |
|---|---|---|---|---|---|---|---|---|---|---|---|---|
|  | Agg | Ab | Frgm | Agg | Ab | Frgm | Agg | Ab | Frgm | Agg | Ab | Frgm |
| 3× Freeze – Thaw | 1.72 | 98.28 | 0.00 | 13.0 | 87.0 | 0.0 | 46.50 | 53.50 | 0.00 | 0.0 | 100.0 | 0.0 |
| 4° C. @ 4 Wks | 0.85 | 99.15 | 0.00 | 4.2 | 95.8 | 0.0 | 42.43 | 56.63 | 0.94 | 0.0 | 100.0 | 0.0 |
| 25° C. @ 4 Wks | 1.29 | 98.71 | 0.00 | 0.0 | 100.0 | 0.0 | 45.66 | 54.34 | 0.00 | 0.0 | 100.0 | 0.0 |
| 40° C. @ 4 Wks | 1.65 | 98.35 | 0.00 | 20.3 | 78.1 | 1.6 | 36.70 | 59.42 | 3.88 | 0.0 | 100.0 | 0.0 |
| 4° C. @ 8 Wks | 5.35 | 90.33 | 4.32 | 2.2 | 97.8 | 0.0 | 38.18 | 56.91 | 4.91 | 0.0 | 100.0 | 0.0 |

TABLE 12-continued in vitro stability analysis of hIL-1a/b DVD-Ig by SEC

|  | 3D12.E3-Ch | | | 13F5.G5-Ch | | | DVD1-Ig | | | DVD2-Ig | | |
| --- | --- | --- | --- | --- | --- | --- | --- | --- | --- | --- | --- | --- |
|  | Agg | Ab | Frgm | Agg | Ab | Frgm | Agg | Ab | Frgm | Agg | Ab | Frgm |
| 25° C. @ 8 Wks | 1.11 | 60.55 | 38.34 | 1.4 | 97.5 | 1.0 | 24.42 | 67.39 | 8.19 | 0.0 | 100.0 | 0.0 |
| 40° C. @ 8 Wks | 4.74 | 81.47 | 13.79 | 34.6 | 65.4 | 0.0 | 20.55 | 67.16 | 12.29 | 0.0 | 100.0 | 0.0 |

The degree of aggregation and fragmentation are shown in percentage, whereas the percentage of Ab represents intact molecule.
Agg: aggregates; Ab: intact antibody; Frgm: fragments.

Both chimeric Abs showed minor degrees of aggregation and fragmentation, normal for a regular IgG molecule. DVD1-Ig showed some aggregation on SCE after purification. In the stability analysis, DVD1-Ig also showed aggregations in PBS under different conditions; however the percentage of aggregated form of DVD1-Ig did not increase during prolonged storage or at higher temperatures. The percentage of the fragmented form of DVD1-Ig were in the normal range, similar to that of the chimeric 3D12.E3 Ab. In contrast, DVD2-Ig showed exceptional stability. Neither aggregation nor fragmentation was detected for DVD2-Ig in all conditions tested, and 100% of DVD2-Ig maintained as intact monomeric molecule.

Example 1.6

Determination of Antigen Binding Affinity of hIL-1a/bDVD-Igs

The kinetics of DVD-Ig binding to rhIL1-α and rhIL1-β was determined by surface plasmon resonance-based measurements with a Biacore 3000 instrument (Biacore AB, Uppsala, Sweden) using HBS-EP (10 mM HEPES, pH 7.4, 150 mM NaCl, 3 mM EDTA, and 0.005% surfactant P20) at 25° C. All chemicals were obtained from Biacore AB (Uppsala, Sweden) or otherwise from a different source as described herein. Approximately, 5000 RU of goat anti-human IgG Fcγ fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 mg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-human IgG in flow cell 1 and 3 was used as the reference surface. For kinetic analysis, rate equations derived from the 1:1 Langmuir binding model were fitted simultaneously to association and dissociation phases of all ten injections (using global fit analysis) using the Bioevaluation 4.0.1 software. Purified DVD-Ig samples were diluted in HEPES-buffered saline for capture across goat anti-human IgG Fc specific reaction surfaces and injected over reaction matrices at a flow rate of 5 ml/min. The association and dissociation rate constants, kon (M-1s-1) and koff (s-1) were determined under a continuous flow rate of 25 ml/min. Rate constants were derived by making kinetic binding measurements at ten different antigen concentrations ranging from 1.25 to 1000 nM. The equilibrium dissociation constant (M) of the reaction between DVD-Ig and rhIL1α/β was then calculated from the kinetic rate constants by the following formula: KD=koff/kon. Aliquots of rhIL1α/β samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 5 ml/min. The anti-Fc antibody immobilized surfaces were completely regenerated and retained their full capture capacity over twelve cycles. The apparent stoichiometry of the captured DVD-Ig-rhIL1α/β complex was calculated under saturating binding conditions (steady-state equilibrium) using the following formula:

$$\text{Stoichiometry} = \frac{rhIL1\alpha/\beta \text{ response } (RU)}{DVD \text{ response } (RU)} \times \frac{DVD-Ig \text{ MW}}{rhIL1\alpha/\beta \text{ MW}}$$

The Biacore analysis indicated the chimeric Abs possessed similar binding kinetics and affinities to IL-1 as the original hybridoma mAbs, indicating that the correct VL/VH sequences had been isolated (Table III). The overall binding parameters of the two DVD-Igs to hIL-1α were similar, with the affinities of the DVD-Igs being only 2-3 fold less than that of the chimeric 3D12.E3 Ab. The binding affinity of DVD2-Ig to hIL-1β was slightly less than the chimeric Ab 13F5.G5, but 3-fold higher than that of DVD1-Ig. The affinity of the two DVD-Igs to hIL-1 as compared to the affinity of chimeric Abs to hIL-1 was similar as indicated by the evaluation of the stoichiometry to IL-1. Both chimeric Abs, being bivalent monospecific, bound to IL-1α and IL-1β on Biacore with a stoichiometry of 1.6 and 1.7, respectively. This is common for an IgG due to inter-molecular interference when antibodies are immobilized densely on the Biacore sense chip resulting in stoichiometry being in the range from 1.5 to 2.0. The stoichiometry of both DVD-Igs for hIL-1ot and hIL-1β were similar to that of the two chimeric Abs, indicating that both DVD-Igs possessed bivalent binding capability to each antigen.

TABLE 13

Functional characterization of anti-IL-1 DVD-Ig molecule

| | Antigen | $k_{on}$ (M−1 s−1) | $k_{off}$ (s−1) | $K_d$ (M) | Stoichiometry | Potency $IC_{50}$ (M) |
|---|---|---|---|---|---|---|
| 3D13.E3 | hIL-1α | 6.43E+05 | 7.13E−04 | 1.11E−09 | 2.0 | 6.70E−10 |
| 3D12.E3-CH | hIL-1α | 4.12E+05 | 5.52E−04 | 1.34E−09 | 1.6 | 7.00E−10 |
| DVD1-Ig | hIL-1α | 3.70E+04 | 1.05E−04 | 2.83E−09 | 1.8 | 2.30E−09 |
| DVD2-Ig | hIL-1α | 7.35E+04 | 2.52E−04 | 3.42E−09 | 2.0 | 2.90E−09 |
| 13F5.G5 | hIL-1β | 2.13E+06 | 6.21E−04 | 2.91E−10 | 1.8 | 6.00E−10 |
| 13F5.G5-Ch | hIL-1β | 1.41E+06 | 6.54E−04 | 4.62E−10 | 1.7 | 5.30E−10 |
| DVD1-Ig | hIL-1β | 6.09E+05 | 1.59E−03 | 2.60E−09 | 1.5 | 3.10E−09 |
| DVD2-Ig | hIL-1β | 1.19E+06 | 9.50E−04 | 7.98E−10 | 1.8 | 1.60E−09 |

Affinity and stoichiometry were measured by Biacore; Potency ($IC_{50}$) was determined by MRC-5 bioassay.

In addition, tetravalent dual-specific antigen binding of DVD-Ig was also analyzed by Biacore (Table 14). DVD-Ig was first captured via a goat anti-human Fc antibody on the Biacore sensor chip, and the first antigen was injected and a binding signal observed. As the DVD-Ig was saturated by the first antigen, the second antigen was then injected and the second signal observed. This was done either by first injecting IL-1β then IL-1α or by first injecting IL-1α followed by IL-1β for DVD2-Ig. In either sequence, a dual-binding activity was detected. Similar results were obtained for DVD1-Ig. Thus each DVD-Ig was able to bind both antigens simultaneously as a dual-specific tetravalent molecule. As shown in Table IV, the stoichiometry of both DVD-Ig to the first antigen, either hIL-1α at or hIL-1β were larger than 1.5, similar to that of mono-specific bivalent binding. Upon the injection of the second antigen, while DVD-Ig was already occupied by the first antigen, the stoichiometry of both DVD-Igs to the second antigen (i.e. hIL-1α at or hIL-1β) was between 1.0 and 1.3. Thus DVD-Ig is able to bind two IL-1α and two IL-1α molecules. DVD-Ig was first captured via a goat anti-human Fc antibody on the Biacore sensor chip, and the first antigen was injected and a binding signal observed, followed by the injection of the second antigen.

TABLE 14

Stoichiometry analysis of hIL-1a/b DVD-Ig in tetravalent dual-specific binding to IL-1α/β

| | Response Unit | | Stoichiometry | |
|---|---|---|---|---|
| Captured Ab | 1st antigen | 2nd antigen | hIL-1α: DVD-Ig | hIL-1β: DVD-Ig |
| DVD1-Ig: 932 | hIL-1α: 190 | hIL-1β: 75 | 2.3 | 1.0 |
| DVD1-Ig: 1092 | hIL-1β: 141 | hIL-1α: 107 | 1.1 | 1.5 |
| DVD2-Ig: 1324 | hIL-1α: 209 | hIL-1β: 137 | 1.8 | 1.3 |
| DVD2-Ig: 1184 | hIL-1β: 159 | hIL-1α: 131 | 1.2 | 1.6 |

Example 1.7

Determination of Functional Homogeneity of DVD-Ig

Because DVD2-Ig was purified by Protein A chromatography instead of target-specific affinity chromatography, any potential misfolded and/or mismatched VL/VH domains, if present, can be assessed by binding studies against the 2 different antigens. Such binding analysis was conduced by size exclusion liquid chromatography (SEC). DVD2-Ig, alone or after a 120-min incubation period at 37° C. withIL-1α, IL-1β, or bothIL-1α and IL-1β, in equal molar ratio, were applied to the column. Each of the antigens was also run alone as controls. The SEC results indicated that DVD2-Ig was able to bind IL-1α and IL-1β in solution, and such binding resulted in a shift to the SEC signal indicating an increase in the dynamic size of DVD2-Ig when it was in complex with either antigen. The shift of the DVD2-Ig signal was 100%, not partial, suggesting all DVD2-Ig molecules were able to bind the antigen. In the presence of bothIL-1α and IL-1β there was a further and complete shift of the DVD2-Ig signal, indicating all DVD2-Ig molecules were able to bind both antigens in a uniform fashion. This experiment demonstrated that DVD-Ig was expressed as a functionally homogeneous protein. This has significant implications as it demonstrates that DVD-Ig can be produced as a homogeneous single, functional species, which differs from all previously described bi-specific, multi-specific, and multi-valent immunoglobulin-like and immunoglobulin-derived molecules.

Example 1.8

Determination of Biological Activity of DVD-Ig

The biological activity of DVD-Ig was measured using MRC-5 bioassay. The MRC-5 cell line is a human lung fibroblast cell line that produces IL-8 in response to human IL-1α and IL-1β in a dose-dependent manner. MRC-5 cells were obtained from ATCC and cultured in 10% FBS complete MEM at 37° C. in a 5% CO2 incubator. To determine neutralizing activity of the DVD-Ig against human IL-1α or IL-1β, 50 ul of Ab (1E-7 to 1E-12 M) in MEM/10% FBS was added to a 96 well plate and pre-incubated with 50 ul of hIL-1α or hIL-1β (200 pg/ml) for 1 hr at 37° C., 5% CO2. MRC-5 cells at a concentration of 1E5/ml were then added (100 ul) to all wells and the plates were incubated overnight at 37° C. in a 5% CO2 incubator. The supernatants were harvested, and human L-8 production measured by standard ELISA (R&D Systems, Minneapolis, Minn.). Neutralizing activity of the DVD-Ig was determined by its ability to inhibit IL-8 production.

As shown in Table 13, both DVD-Igs were able to neutralize hIL-1α and hIL-1β. Consistent with the binding affinity to IL-1α, the neutralizing activities of DVD1-Ig and DVD2-Ig against hIL-1α were also similar, i.e. 3-fold less than that of the chimeric Abs (see Table III). Consistent with its binding affinity for hIL-1α, the neutralizing activity of DVD2-Ig to hIL-1β is slightly less than that of the chimeric Ab 13F5.G5, but 3-fold higher than that of DVD1-Ig. Overall there was no significant decrease in the biological activities of DVD-Ig molecules compared to the original mAbs.

To determine if DVD-Ig was able to inhibit IL-8 production in the presence of both hIL-1α and IL-1β, equal amounts of hIL-1α and hIL-1β were added in the same culture system of MRC-5 assay. Both DVD1-Ig and DVD2-Ig were able to inhibit IL-8 synthesis by MRC-5 cells in the presence of both IL-1α and IL-1β, with activities similar to that of mono-assays where only one cytokine was present (Table 13). In this assay where both IL-1α and IL-1β were present, the dual-inhibition activity of DVD2-Ig (1.2 nM) was higher than that of DVD1-Ig (2.2 nM).

Example 2

Analysis of Linker Size and Variable Domain Orientation in the DVD-Ig Molecule

Additional DVD-Ig molecules with different parent mAb pairs, as shown in Table 15, were constructed. For each pair of mAbs, four different DVD-Ig constructs were generated: 2 with a short linker and 2 with a long linker, each in two different domain orientations: a-b-C (alpha-beta-constant domain) and b-a-C (beta-alpha-constant domain). The linker sequences, were derived from the N-terminal sequence of human Ck or CH1 domain, as follows:

Short linker: light chain: TVAAP(SEQ ID NO:44); heavy chain: ASTKGP (SEQ ID NO:42)
Long linker: light chain: TVAAPSVFIFPP (SEQ ID NO:50); heavy chain: ASTKGPSVFPLAP (SEQ ID NO:48).

All heavy and light chain constructs were subcloned into the pBOS expression vector, and expressed in COS cells or freestyle 293 cells.

To construct new DVD clones, the variable domains of the two mAbs, both light chain and heavy chain, were first jointed in tandem using overlapping PCR as described for hIL-1ab-DVD1-Ig and hIL-1abDVD2-Ig. The jointed pieces were then subcloned in pBOS vecter using homologous recombination. Briefly, vectors were linearized by restriction digestion (2 ug of pBOS-hCk vector were digested with FspAI and BsiWI in O+ buffer, and 2 ug of pBOS-hCγ z,non a vector was digested with FspAI and SalI in O+ buffer). The digested samples were run on 1% agarose gel and the backbone fragment purified in 50 ul water. For homologous recombination and transformation, DH5α competent cells were thaw on ice, and mixed with 20-50 ng jointed PCR product and 20-50 ng of linearized vector (in every 50 ul DH5α cells). The mixture was mixed gently and incubated on ice for 45 minutes, followed by heat shock at 42° C. for 1 minute. Then 100 ul SOC medium were added and incubated at 37° C. for 1 hour. The transformation culture was inoculated on LB/Agar plates containing Ampicillin and incubated at 37° C. for 18-20 hours. The bacterial clones were isolated, from which DNA was purified and subjected to sequencing analysis. The final sequence-verified clones were co-transfected (matching HV and LC of the same Ab pair) in COS or 293 cells for Ab expression and purification, as previously described.

Characteristics of the purified DVD-Ig proteins are summarized in Table 16. The left section of the table 16 shows the specificity, binding affinity, and neutralization potency of the 2 pairs of mabs used for the construction of the new hIL-1a/bDVD-Ig molecules. Antibodies 18F4.2C8 and 1B12.4H4 (see example 1.1.D) were used to construct hIL-1a/bDVD3a-Ig, hIL-1a/bDVD4a-Ig, hIL-1a/bDVD3b-Ig, and hIL-1a/bDVD4b-Ig. hIL-1a/bDVD3a-Ig and hIL-1a/bDVD4a-Ig were in a-b-C orientation, with a short and long linker, respectively. hIL-1a/bDVD3b-Ig and hIL-1a/bDVD4b-Ig were in b-a-C orientation, with a short and long linker, respectively. Antibodies 6H3.1A4 and 6B12.4F6 were used to construct hIL-1a/bDVD5a-Ig, hIL-1a/bDVD6a-Ig, hIL-1a/bDVD5b-Ig, and hIL-1a/bDVD6b-Ig. hIL-1a/bDVD5a-Ig and hIL-1a/bDVD6a-Ig were in a-b-C orientation, with a short and long linker, respectively. hIL-1a/bDVD5b-Ig and hIL-1a/bDVD6b-Ig were in b-a-C orientation, with a short and long linker, respectively. The molecular cloning of these additional hIL-1a/bDVD-Igs were performed using the procedure previously described for hIL-1a/bDVD1-Ig (see example 1.3), using overlapping PCR procedures. The amino acid sequences of these additional hIL-1a/bDVD-Igs are disclosed in Table 15.

TABLE 15

Amino acid sequence of heavy chain and light chain of six DVD Ig capable of binding IL-1α and IL-1β.

| Protein Protein region | Sequence Identifier | Sequence 12345678901234567890 |
|---|---|---|
| DVD HEAVY VARIABLE hIL-1a/b DVD3a-Ig | SEQ ID NO.:41 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSSAS TKGPQVHLKESGPGLVAPSQ SLSITCTVSGFSLTDYGVSW IRQPPGKGLEWLGLIWGGGD TYYNSPLKSRLSTRKDNSKS QVFLKMNSLQTDDTAVYYCA KQRTLWGYDLYGHDYWGQGT SVTVSS |
| 18F4.2C8 VH | SEQ ID NO.:3 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| LINKER | SEQ ID NO.:42 | ASTKGP |
| 1B12.4H4 VH | SEQ ID NO.:9 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE HIL-1a/b DVD3a-Ig | SEQ ID NO.:43 | DIVMTQSQRFMSTSVGDRVS VTCKASQNVGTNIAWYQQKP GQSPPALIYSASYRYSGVPD RFTGSGSGTDFTLTISNVQS VDLAEYFCQQYTRYPLTFGG GTKLEIKRTVAAPETTVTQS PASLSMAIGEKVTIRCITST DIDVDMNWYQQKPGEPPKLL ISQGNTLRPGVPSRFSSSGS |

TABLE 15-continued

Amino acid sequence of heavy chain and light chain of six DVD Ig capable of binding IL-1α and IL-1β.

| Protein Protein region | Sequence Identifier | Sequence 12345678901234567890 |
|---|---|---|
| | | GTDFVFIIENMLSEDVADYY CLQSDNLPLTFGAGTKLELK RR |
| 18F4.2C8 VL | SEQ ID NO.:4 | DIVMTQSQRFNSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| LINKER | SEQ ID NO.:44 | TVAAP |
| 1B12.4H4 VL | SEQ ID NO.:10 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE hIL-1a/b DVD3b-Ig | SEQ ID NO.:45 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SSASTKGPEVQLQQSGAELV KPGASVKLSCTASGLNIKDT YMHWLKQRPEQGLEWIGRID PANGNAKYDPRFLGKATITA DTSSNTAYLQLSSLTSEDTA VYYCARGDGNFHFDYWGQGT TLTVSS |
| 1B12.4H4 VH | SEQ ID NO.:9 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| LINKER | SEQ ID NO.:42 | ASTKGP |
| 18F4.2C8 VH | SEQ ID NO.:3 | EVQLQQSGAELVKPGASVKL SCTASGLNIKDTYMHWLKQR PEQGLEWIGRTDPANGNAKY DPRFLGKATITADTSSNTAY LQLSSLTSEDTAVYYCARGD GNFHFDYWGQGTTLTVSS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV |

TABLE 15-continued

Amino acid sequence of heavy chain and light chain of six DVD Ig capable of binding IL-1α and IL-1β.

| Protein Protein region | Sequence Identifier | Sequence 12345678901234567890 |
|---|---|---|
| | | LDSDGSFFLYSKLTVDKSRW QQGNVFSCSVMHEALHNHYT QKSLSLSPGK |
| DVD LIGHT VARIABLE HIL-1a/b DVD3b-Ig | SEQ ID NO.:46 | ETTVTQSPASLSMAIGEKVT IRCITSTDIDVDNNWYQQKP GEPPKLLISQGNTLRPGVPS RFSSSGSGTDFVFIIENMLS EDVADYYCLQSDNLPLTFGA GTKLELKR<u>TVAAP</u>DIVMTQS QRFMSTSVGDRVSVTCKASQ NVGTNTAWYQQKPGQSPRAL IYSASYRYSGVPDRFTGSGS GTDFTLTISNVQSVDLAEYF CQQYTRYPLTFGGGTKLEIK R |
| 1B12.4H4 VL | SEQ ID NO.:10 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| LINKER | SEQ ID NO.:44 | TVAAP |
| 18F4.2C8 VL | SEQ ID NO.:4 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE hIL-1a/b DVD4a-Ig | SEQ ID NO.:47 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS<u>AS TKGPSVFPLAP</u>QVHLKESGP GLVAPSQSLSITCTVSGFSL TDYGVSWIRQPPGKGLEWLG LIWGGGDTYYNSPLKSRLSI RKDNSKSQVFLKMNSLQTDD TAVYYCAKQRTLWGYDLYGM DYWGQGTSVTVSS |
| 18F4.2C8 VH | SEQ ID NO.:3 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| LINKER | SEQ ID NO.:48 | <u>ASTKGPSVFPLAP</u> |
| 1B12.4H4 VH | SEQ ID NO.:9 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |

TABLE 15-continued

Amino acid sequence of heavy chain and light chain of six DVD Ig capable of binding IL-1α and IL-1β.

| Protein region | Sequence Identifier | Sequence 12345678901234567890 |
|---|---|---|
| CH | SEQ ID NO.:34 | ASTKGPSVFPLAPSSKSTSG GTAALGCLVKDYFPEPVTVS WNSCALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE HIL-1a/bDVD4a-Ig | SEQ ID NO.:49 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR TVAAPSVFIFPP ETTVTQSPASLSMATGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| 18F4.2C8 VL | SEQ ID NO.:4 | DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| LINKER | SEQ ID NO.:50 | TVAAPSVFIFPP |
| 1B12.4H4 VL | SEQ ID NO.:10 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE hIL-1a/b DVD4b-Ig | SEQ ID NO.:51 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS ASTKGPSVFPLAP EVQLQ QSGAELVKPGASVKLSCTAS GLNIKDTYMHWLKQRPEQGL EWIGRIDPANGNAKYDPRFL GKATITADTSSNTAYLQLSS LTSEDTAVYYCARGDGNFHF DYWGQGTTLTVSS |
| 1B12.4H4 VH | SEQ ID NO.:9 | QVHLKESGPGLVAPSQSLSI TCTVSGFSLTDYGVSWIRQP PGKGLEWLGLIWGGGDTYYN SPLKSRLSIRKDNSKSQVFL KMNSLQTDDTAVYYCAKQRT LWGYDLYGMDYWGQGTSVTV SS |
| LINKER | SEQ ID NO.:48 | ASTKGPSVFPLAP |
| 18F4.2C8 VH | SEQ ID NO.:3 | EVQLQQSGAELVKPGASVKL SCTASGLNIKDTYMHWLKQR PEQGLEWIGRIDPANGNAKY DPRFLGKATITADTSSNTAY LQLSSLTSEDTAVYYCARGD GNFHFDYWGQGTTLTVSS |
| CH | SEQ ID NO.:34 | ASTKGPSVFPLAPSSKSTSG GTAALGCLVKDYFPEPVTVS WNSGALTSGVGTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE HIL-1a/b DVD4b-Ig | SEQ ID NO.:52 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR TVAAPSVFIFPP DIVMTQSQRFMSTSVGDRVS VTCKASQNVGTNIAWYQQKP GQSPRALIYSASYRYSGVPD RFTGSGSGTDFTLTISNVQS VDLAEYFCQQYTRYPLTFGG GTKLEIKR |
| 1B12.4H4 VL | SEQ ID NO.:10 | ETTVTQSPASLSMAIGEKVT IRCITSTDIDVDMNWYQQKP GEPPKLLISQGNTLRPGVPS RFSSSGSGTDFVFIIENMLS EDVADYYCLQSDNLPLTFGA GTKLELKR |
| LINKER | SEQ ID NO.:50 | TVAAPSVFIFPP |
| 18F4.2C8 VL | SEQ ID NO.:4 | DIVMTQSQRFMSTSVGDRVS VTCKASQNVGTNIAWYQQKP GQSPPALIYSASYRYSGVPD RFTGSGSGTDFTLTISNVQS VDLAEYFCQQYTRYPLTFGG GTKLEIKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE hIL-1a/b DVD5a-Ig | SEQ ID NO.:53 | QVQLQQPGAELVRPGASVKL SCKASGYTFTTYWNNWVKQR PEQGLEWIGRIDPYDSETLY SQKFKDTAILTVDKSSSTAY |

TABLE 15-continued

Amino acid sequence of heavy chain and light chain of six DVD Ig capable of binding IL-1α and IL-1β.

| Protein Protein region | Sequence Identifier | Sequence 12345678901234567890 |
|---|---|---|
| | | MQLSSLTSEDSAVYYCARYGFDYWGQTTLTVSS<u>ASTKGP</u>EVQLQQSGPELVKTGTSVKISCKASGYSFTGYYMHWVRQSHGKSLEWIGYISCYNGFTSYNPKFKGKATFTVDTSSSTAYIQFSRLTSEDSAVYYCARSDYYGTNDYWGQGTTLTVSS |
| 6H3.1A4.3E11 VH | SEQ ID NO.:5 | QVQLQQPGAELVRPGASVKLSCKASGYTFTTYWNNWVKQRPEQGLEWIGRIDPYDSETLYSQKFKDTAILTVDKSSSTAYMQLSSLTSEDSAVYYCARYGFDYWGQGTTLTVSS |
| LINKER | SEQ ID NO.:42 | ASTKGP |
| 6B12.4F6 VH | SEQ ID NO.:11 | EVQLQQSGPELVKTGTSVKISCKASGYSFTGYYMHWVRQSHGKSLEWIGYISCYNGFTSYNPKFKGKATFTVDTSSSTAYIQFSRLTSEDSAVYYCARSDYYGTNDYWGQGTTLTVSS |
| CH | SEQ ID NO.:34 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DVD LIGHT VARIABLE HIL-1a/b DVD5a-Ig | SEQ ID NO.:54 | QIVLTQSPALMSASPGEKVTMTCSASSSVNYMYWYQQKPRSSPKPWIYLTSNLASGVPARFSGSGSGTSYSLTISSMEAEDAATYYCQQWNSNPYTFGGGTKLEMKR<u>TVAAP</u>QIVLTQSPAIMSASPGEKVTITCSASSSVSYMHWFQQKPGASPKLWIYSTSNLASGVPARFSGSGSGTSYSLTVSRMEAEDAATYYCQQRSTYPYTFGGGTKLEIKR |
| 6H3.1A4.3E11 VL | SEQ ID NO.:6 | QIVLTQSPALMSASPGEKVTMTCSASSSVNYMYWYQQKPRSSPKPWIYLTSNLASGVPARFSGSGSGTSYSLTISSMEAEDAATYYCQQWNSNPYTFGGGTKLEMKR |
| LINKER | SEQ ID NO.:44 | <u>TVAAP</u> |
| 6B12.4F6 VL | SEQ ID NO.:12 | QIVLTQSPAIMSASPGEKVTITCSASSSVSYMHWFQQKPGASPKLWIYSTSNLASGVPARFSGSGSGTSYSLTVSRMEAEDAATYYCQQRSTYPYTFGGGTKLEIKR |

TABLE 15-continued

Amino acid sequence of heavy chain and light chain of six DVD Ig capable of binding IL-1α and IL-1β.

| Protein Protein region | Sequence Identifier | Sequence 12345678901234567890 |
|---|---|---|
| CL | SEQ ID NO.:36 | TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| DVD HEAVY VARIABLE hIL-1a/b DVD5b-Ig | SEQ ID NO.:55 | EVQLQQSGPELVKTGTSVKISCKASGYSFTGYYMHWVRQSHGKSLEWIGYISCYNGFTSYNPKFKGKATFTVDTSSSTAYIQFSRLTSEDSAVYYCARSDYYGTNDYWGQGTTLTVSS<u>ASTKGP</u>QVQLQQPGAELVRPGASVKLSCKASGYTFTTYWMNWVKQRPEQGLEWIGRIDPYDSETLYSQKFKDTAILTVDKSSSTAYMQLSSLTSEDSAVYYCARYGFDYWGQGTTLTVSS |
| 6B12.4F6 VH | SEQ ID NO.:11 | EVQLQQSGPELVKTGTSVKISCKASGYSFTGYYMHWVRQSHGKSLEWIGYISCYNGFTSYNPKFKGKATFTVDTSSSTAYIQFSRLTSEDSAVYYCARSDYYGTNDYWGQGTTLTVSS |
| LINKER | SEQ ID NO.:42 | <u>ASTKGP</u> |
| 6H3.1A4.3E11 VH | SEQ ID NO.:5 | QVQLQQPGAELVRPGASVKLSCKASGYTFTTYWMNWVKQRPEQGLEWIGRIDPYDSETLYSQKFKDTAILTVDKSSSTAYMQLSSLTSEDSAVYYCARYGFDYWGQGTTLTVSS |
| CH | SEQ ID NO.:34 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| DVD LIGHT VARIABLE HIL-1a/b DVD5b-Ig | SEQ ID NO.:56 | QIVLTQSPAIMSASPGEKVTITCSASSSVSYMHWFQQKPGASPKLWIYSTSNLASGVPARFSGSGSGTSYSLTVSRMEAEDAATYYCQQRSTYPYTFGGGTKLEIKR<u>TVAAP</u>QIVLTQSPALMSASPGEKVTMTCSASSSVNYMYWYQQKPRSSPKPWIYLTSNLASGVPARFSGSGSGTSYSLTISSMEAEDAATYYCQQWNSNPYTFGGGTKLEMKR |
| 6B12.4F6 VL | SEQ ID NO.:12 | QIVLTQSPAIMSASPGEKVTITCSASSSVSYMHWFQQKPGASPKLWIYSTSNLASGVPAR |

TABLE 15-continued

Amino acid sequence of heavy chain and light chain of six DVD Ig capable of binding IL-1α and IL-1β.

| Protein region | Sequence Identifier | Sequence 12345678901234567890 |
|---|---|---|
| | | FSGSGSGTSYSLTVSRMEAE DAATYYCQQRSTYPYTFGGG TKLEIKR |
| LINKER | SEQ ID NO.:44 | TVAAP |
| 6H3.1A4.3E11 VL | SEQ ID NO.:6 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE hIL-1a/b DVD6a-Ig | SEQ ID NO.:57 | QVQLQQPGAELVRPGASVKL SCKASGYTFTTYWMNWTKQR PEQGLEWIGRIDPYDSETLY SQKFKDTATLTVDKSSSTAY MQLSSLTSEDSAVYYCARYG FDYWGQGTTLTVSSASTKGP SVFPLAPEVQLQQSGPELVK TGTSVKTSCKASGYSFTGYY MHWVRQSHGKSLEWIGYISC YNGFTSYNPKFKGKATFTVD TSSSTAYTQFSRLTSEDSAV YYCARSDYYGTNDYWGQGTT LTVSS |
| 6H3.1A4.3E11 VH | SEQ ID NO.:5 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| LINKER | SEQ ID NO.:48 | ASTKGPSVFPLAP |
| 6B12.4F6 VH | SEQ ID NO.:11 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE HIL-1a/b DVD 6a-Ig | SEQ ID NO.:58 | QTVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKRTVAAPSVFIFPPQ IVLTQSPAIMSASPGEKVTI TCSASSSVSYMHWFQQKPGA SPKLWIYSTSNLASGVPARF SGSGSGTSYSLTVSRMEAED AATYYCQQRSTYPYTFGGGT KLEIKRR |
| 6H3.1A4.3E11 VL | SEQ ID NO.:6 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| LINKER | SEQ ID NO.:50 | TVAAPSVFIFPP |
| 6B12.4F6 VL | SEQ ID NO.:12 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |
| CL | SEQ ID NO.:36 | RTVAAPSVFIFPPSDEQLKS GTASVVCLLNNFYPREAKVQ WKVDNALQSGNSQESVTEQD SKDSTYSLSSTLTLSKADYE KHKVYACEVTHQGLSSPVTK SFNRGEC |
| DVD HEAVY VARIABLE hIL-1a/b DVD6b-Ig | SEQ ID NO.:59 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSSAS TKGPSVFPLAPQVQLQQPGA ELVRPGASVKLSCKASGYTF TTYWMNWVKQRPEQGLEWIG RIDPYDSETLYSQKFKDTAI LTVDKSSSTAYMQLSSLTSE DSAVYYCARYGFDYWGQGTT LTVSS |
| 6B12.4F6 VH | SEQ ID NO.:11 | EVQLQQSGPELVKTGTSVKI SCKASGYSFTGYYMHWVRQS HGKSLEWIGYISCYNGFTSY NPKFKGKATFTVDTSSSTAY IQFSRLTSEDSAVYYCARSD YYGTNDYWGQGTTLTVSS |
| LINKER | SEQ ID NO.:48 | ASTKGPSVFPLAP |
| 6H3.1A4.3E11 VH | SEQ ID NO.:5 | QVQLQQPGAELVRPGASVKL SCKASGYTFTTYWMNWVKQR PEQGLEWIGRIDPYDSETLY SQKFKDTAILTVDKSSSTAY MQLSSLTSEDSAVYYCARYG FDYWGQGTTLTVSS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK |

TABLE 15-continued

Amino acid sequence of heavy chain and light chain of six DVD Ig capable of binding IL-1α and IL-1β.

| Protein Protein region | Sequence Identifier | Sequence 12345678901234567890 |
|---|---|---|
| | | EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE HIL-1a/b DVD6b-Ig | SEQ ID NO.:60 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKRTVAAPSVFIFPPQ IVLTQSPALMSASPGEKVTM TCSASSSVNYMYWYQQKPRS SPKPWTYLTSNLASGVPARF SGSGSGTSYSLTISSMEAED AATYYCQQWNSNPYTFGGGT KLEMKRR |
| 6B12.4F6 VL | SEQ ID NO.:12 | QIVLTQSPAIMSASPGEKVT ITCSASSSVSYMHWFQQKPG ASPKLWIYSTSNLASGVPAR FSGSGSGTSYSLTVSRMEAE DAATYYCQQRSTYPYTFGGG TKLEIKR |
| LINKER | SEQ ID NO.:50 | TVAAPSVFIFPP |
| 6H3.1A4.3E11 VL | SEQ ID NO.:6 | QIVLTQSPALMSASPGEKVT MTCSASSSVNYMYWYQQKPR SSPKPWIYLTSNLASGVPAR FSGSGSGTSYSLTISSMEAE DAATYYCQQWNSNPYTFGGG TKLEMKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |

Characteristics of the new DVD constructs are summarized in Table 16. Affinity (Kd) and biological activity (IC50) were determined by Biacore and MRC-5 bioassay, respectively. SDS-PAGE analysis of all new DVD proteins showed normal migration patterns in both reduced and non-reduced conditions, similar to a regular antibody and DVD1/2-Ig.

The functional characterization of the new DVD molecules revealed that with either orientation, DVDs with the long linker performed better than the ones with the short linker in terms of binding and neutralizing of both antigens. With respect to DVDs with the long linkers, those with the b-a-C orientation showed good binding to and neutralization of both antigens, while the DVDs with an a-b-C orientation showed good binding to and neutralization of IL-1α and reduced binding to and neutralization of IL-1β (e.g. DVD4b vs. DVD4a). The DVD-Ig molecule, DVD4b, bound and neutralized both IL-1α and IL-1β with sub-nM and fully retained the binding and neutralizing characteristics of the parent mAbs.

Example 3

Generation of DVD-Ig Capable of Binding IL-12 and IL-18

DVD-Ig molecules capable of binding IL-12 and IL-18 were constructed as described above using two parent mAbs, one against human IL-12p40 (ABT874), and the other against human IL-18 (ABT325). Four different anti-IL12/18 DVD-Ig constructs were generated: 2 with short linker and 2 with long linker, each in two different domain orientations: 12-18-C and 18-12-C (Table VI). The linker sequences, derived from the N-terminal sequence of human $C_\lambda/C_\kappa$ or CH1 domain, were as follows:

For DVD1218 constructs (ABT874 has a $V_\lambda$):
light chain (λ): Short linker: QPKAAP (SEQ ID NO:88); Long linker: QPKAAPSVTLFPP (SEQ ID NO:92)
heavy chain (γ1): Short linker: ASTKGP (SEQ ID NO:42); Long linker: ASTKGPSVFPLAP (SEQ ID NO:48)

For DVD1812 constructs (ABT325 has a $V_\kappa$):
light chain (κ): Short linker: TVAAP (SEQ ID NO:44); Long linker: TVAAPSVFIFPP (SEQ ID NO:50)
heavy chain (γ1): Short linker: ASTKGP(SEQ ID NO:42); Long linker: ASTKGPSVFPLAP (SEQ ID NO:48).

All heavy and light chain constructs were subcloned into the pBOS expression vector, and expressed in COS cells or freestyle 293 cells, followed by purification by Protein A chromatography. The purified materials were subjected to SDS-PAGE and SEC, and their profiles were similar to that of the DVD2-Ig.

The table 17 below describes the heavy chain and light chain constructs used to express each anti-IL12/IL18 DVD-Ig protein.

TABLE 16

Characterization of new DVD-Ig molecules derived from new mAb pairs

| | | | | | | | Affinity ($K_d$) M | | Potency ($IC_{50}$) M | |
| mAb | Specif. | $K_d$(M) | $IC_{50}$(M) | DVD | Orient. | Linker | IL-1α | IL-1β | IL-1α | IL-1β |
|---|---|---|---|---|---|---|---|---|---|---|
| 18F4.2C8 | rhIL-1α | 5.95E−10 | 3.30E−10 | DVD3a | a-b-C | short | 8.37E−10 | 6.37E−08 | 7.50E−10 | NA |
| 1B12.4H4 | rhIL-1β | 2.61E−10 | 6.00E−10 | DVD4a | a-b-C | long | 7.01E−10 | 9.30E−10 | 3.50E−10 | 1.00E−08 |
| | | | | DVD3b | b-a-C | short | 1.24E−09 | 1.90E−10 | 7.00E−10 | 4.00E−10 |
| | | | | DVD4b | b-a-C | long | 5.60E−10 | 1.28E−10 | 3.50E−10 | 5.00E−10 |
| 6H3.1A4 | rhIL-1α | 3.54E−10 | 2.40E−10 | DVD5a | a-b-C | short | 5.08E−10 | 1.25E−08 | 2.60E−09 | 1.90E−08 |
| 6B12.4F6 | rhIL-1β | 5.54E−10 | 4.00E−10 | DVD6a | a-b-C | long | 1.06E−09 | 2.09E−09 | 2.30E−09 | 7.00E−08 |
| | | | | DVD5b | b-a-C | short | 1.32E−08 | 6.71E−10 | 3.30E−09 | 2.50E−10 |
| | | | | DVD6b | b-a-C | long | 8.20E−10 | 6.97E−10 | 1.00E−09 | 7.50E−10 |

NA: no neutralization activity detected.

TABLE 17

Constructs to express anti-IL12/IL18 DVD-Ig proteins

| DVD-Ig protein | Heavy chain construct | Light chain construct |
|---|---|---|
| DVD1218SL | DVD1218HC-SL | DVD1218LC-SL |
| DVD1218LL | DVD1218HC-LL | DVD1218LC-LL |
| DVD1812SL | DVD1812HC-SL | DVD1812LC-SL |
| DVD1812LL | DVD1812HC-LL | DVD1812LC-LL |

Example 3.1.1

Molecular Cloning of DNA Constructs for DVD1218SL and DVD1218LL

To generate heavy chain constructs DVD1218HC-LL and DVD1218HC-SL, VH domain of ABT-874 was PCR amplified using primers Primer 1 and Primer 2L or Primer 2S respectively; meanwhile VH domain of ABT-325 was amplified using primers Primer 3L or Primer 3S and Primer 4 respectively. Both PCR reactions were performed according to standard PCR techniques and procedures. The two PCR products were gel-purified, and used together as overlapping template for the subsequent overlapping PCR reaction using primers Primer 1 and Primer 4 using standard PCR conditions. The overlapping PCR products were subcloned into Srf I and Sal I double digested pBOS-hCγ1,z non-a mammalian expression vector (Abbott) by using standard homologous recombination approach.

To generate light chain constructs DVD1218LC-LL and DVD1218LC-SL, VL domain of ABT-874 was PCR amplified using primers Primer 5 and Primer 6L or Primer 6S respectively; meanwhile VL domain of ABT-325 was amplified using primers Primer 7L or Primer 7S and Primer 8 respectively. Both PCR reactions were performed according to standard PCR techniques and procedures. The two PCR products were gel-purified, and used together as overlapping template for the subsequent overlapping PCR reaction using primers Primer 5 and Primer 8 using standard PCR conditions. The overlapping PCR products were subcloned into Srf I and Not I double digested pBOS-hCk mammalian expression vector (Abbott) by using standard homologous recombination approach. The primers used for these constructions are listed below in table 18:

TABLE 18

```
Primer 1:
TAGAGATCCCTCGACCTCGAGATCCATTGTGCCCGGG    SEQ ID NO.:61
CGCCACCATGGAGTTTGGGCTGAGC Primer 2-
S:CACCTCTGGGCCCTTGGTCGACGCTGAAGAGACGG    SEQ ID NO.:62
TGACCATTGT Primer 2-
L:GGGTGCCAGGGGGAAGACCGATGGGCCCTTGGTCG    SEQ ID NO.:63
ACGCTGAAGAGACGGTGACCATTGT Primer 3-
S:TCTTCAGCGTCGACCAAGGGCCCAGAGGTGCAGCT    SEQ ID NO.:64
GGTGCAGTCT Primer 3-
L:GCGTCGACCAAGGGCCCATCGGTCTTCCCCCTGGC    SEQ ID NO.:65
ACCCGAGGTGCAGCTGGTGCAGTCT Primer 4:
GTAGTCCTTGACCAGGCAGCC                    SEQ ID NO.:66
```

TABLE 18-continued

```
Primer 5:
TAGAGATCCCTCGACCTCGAGATCCATTGTGCCCGGG    SEQ ID NO.:67
CGCCACCATGACTTGGACCCCACTC Primer 6-
S:TATTTCGGGGGCAGCCTTGGGCTGACCTAGTACTG    SEQ ID NO.:68
TGACCTTGGT Primer 6-
L:GGGCGGGAACAGAGTGACCGAGGGGGCAGCCTTGG    SEQ ID NO.:69
GCTGACCTAGTACTGTGACCTTGGT Primer 7-
S:CTAGGTCAGCCCAAGGCTGCCCCCGAAATAGTGAT    SEQ ID NO.:70
GACGCAGTCT Primer 7-
L:CAGCCCAAGGCTGCCCCCTCGGTCACTCTGTTCCC    SEQ ID NO.:71
GCCCGAAATAGTGATGACGCAGTCT Primer 8:
GTCCCAGGTGGGGACCCTCACTCTAGAGTCGCGGCCG    SEQ ID NO.:72
CCTAACACTCTCCCCTGTTGAA
```

Similar approach has been used to generate DVD1812SL and DVD1812LL as described below:

Example 3.1.2

Molecular Cloning of DNA Constructs for DVD1812SL and DVD1812LL

To generate heavy chain constructs DVD1812HC-LL and DVD1812HC-SL, VH domain of ABT-325 was PCR amplified using primers Primer 1 and Primer 9L or Primer 9S respectively; meanwhile VH domain of ABT-874 was amplified using primers Primer 10L or Primer 10S and Primer 4 respectively. Both PCR reactions were performed according to standard PCR techniques and procedures. The two PCR products were gel-purified, and used together as overlapping template for the subsequent overlapping PCR reaction using primers Primer 1 and Primer 4 using standard PCR conditions. The overlapping PCR products were subcloned into Srf I and Sal I double digested pBOS-hCγ1,z non-a mammalian expression vector (Abbott) by using standard homologous recombination approach. The following are primers' sequences:

To generate light chain constructs DVD1812LC-LL and DVD1812LC-SL, VL domain of ABT-325 was PCR amplified using primers Primer 11 and Primer 12L or Primer 12S respectively; meanwhile VL domain of ABT-874 was amplified using primers Primer 13L or Primer 13S and Primer 14 respectively. Both PCR reactions were performed according to standard PCR techniques and procedures. The two PCR products were gel-purified, and used together as overlapping template for the subsequent overlapping PCR reaction using primers Primer 11 and Primer 14 using standard PCR conditions. The overlapping PCR products were subcloned into Srf I and Not I double digested pBOS-hCk mammalian expression vector (Abbott) by using standard homologous recombination approach. The primers used for these constructions are listed below in table 19:

TABLE 19

```
Primer 9-S:
CACCTGTGGGCCCTTGGTCGACGCTGAAGAGACGGTG    SEQ ID NO.:73
ACCATTGT
```

TABLE 19-continued

```
Primer 9-L:
GGGTGCCAGGGGGAAGACCGATGGGCCCTTGGTCGAC       SEQ ID NO.:74
GCTGAAGAGACGGTGACCATTGT Primer 10-
S:TCTTCAGCGTCGACCAAGGGCCCACAGGTGCAGCT        SEQ ID NO.:75
GGTGGAGTCT Primer 10-
L:GCGTCGACCAAGGGCCCATCGGTCTTCCCCCTGGC        SEQ ID NO.:76
ACCCCAGGTGCAGCTGGTGGAGTCT Primer 11:
TAGAGATCCCTCGACCTCGAGATCCATTGTGCCCGGG       SEQ ID NO.:77
CGCCACCATGGAAGCCCCAGCGCAGCTT Primer 12-S:
AGACTGTGGTGCAGCCACAGTTCGTTTAATCTCCAGT       SEQ ID NO.:78
CGTGT Primer 12-
L:TGGCGGGAAGATGAAGACAGATGGTGCAGCCACAG        SEQ ID NO.:79
TTCGTTTAATCTCCAGTCGTGT Primer 13-S:
AAACGAACTGTGGCTGCACCACAGTCTGTGCTGACTC       SEQ ID NO.:80
AGCCC Primer 13-
L:ACTGTGGCTGCACCATCTGTCTTCATCTTCCCGCC        SEQ ID NO.:81
ACAGTCTGTGCTGACTCAGCCC Primer 14:
GTCCCAGGTGGGGACCCTCACTCTAGAGTCGCGGCCG       SEQ ID NO.:82
CTCATGAACATTCTGTAGGGGC
```

The final DNA sequences for eight heavy and light chain constructs of anti-IL 12/IL-18 DVD-Ig are as shown in table 20:

TABLE 20

Amino acid sequence of DVD binding proteins capable of binding IL-12 and IL-18

| Protein region | Sequence Identifier | Sequence 12345678901234567890 |
|---|---|---|
| DVD HEAVY VARIABLE DVD1218HC-SL | SEQ ID NO.:83 | QVQLVESGGGVVQPGRSLRL SCAASGFTFSSYGMHWVRQA PGKGLEWVAFIRYDGSNKYY ADSVKGRFTISRDNSKNTLY LQMNSLRAEDTAVYYCKTHG SHDNWGQGTMVTVSS<u>ASTKG PEVQLVQSGTEVKKPGESLK ISCKGSGYTVTSYWIGWVRQ MPGKGLEWMGFIYPGDSETR YSPTFQGQVTISADKSFNTA FLQWSSLKASDTAMYYCARV GSGWYPYTFDIWGQGTMVTV SS |
| ABT-874 VH | SEQ ID NO.:84 | QVQLVESCGGVVQPGRSLRL SCAASGFTFSSYGMHWVRQA PGKGLEWVAFIRYDGSNKYY ADSVKGRFTISRDNSKNTLY LQMNSLRAEDTAVYYCKTHG SHDNWGQGTMVTVSS |
| LINKER | SEQ ID NO.:42 | <u>ASTKGP</u> |
| ABT-325 VH | SEQ ID NO.:85 | EVQLVQSGTEVKKPGESLKI SCKGSGYTVTSYWIGWVRQM PGKGLEWMGFIYPGDSETRY SPTFQGQVTISADKSFNTAF LQWSSLKASDTAMYYCARVG SGWYPYTFDIWGQGTMVTVS S |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPEAAGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE DVD1218LC-SL | SEQ ID NO.:86 | MTWTPLLFLTLLLHCTGSLS QSVLTQPPSVSGAPGQRVTI SCSGSRSNIGSNTVKWYQQL PGTAPKLLIYYNDQRPSGVP DRFSGSKSGTSASLAITGLQ AEDEADYYCQSYDRYTHPAL LFGTGTKVTVLG<u>QPKAAP</u>EI VMTQSPATLSVSPGERATLS CRASESISSNLAWYQQKPGQ APRLFIYTASTRATDIPARF SGSGSGTEFTLTISSLQSED FAVYYCQQYNNWPSITFGQG TRLEIKR |
| ABT-874 VL | SEQ ID NO.:87 | QSVLTQPPSVSGAPGQRVTI SCSGSRSNIGSNTVKWYQQL PGTAPKLLIYYNDQRPSGVP DRFSGSKSGTSASLAITGLQ AEDEADYYCQSYDRYTHPAL LFGTGTKVTVLG |
| LINKER | SEQ ID NO.:88 | <u>QPKAAP</u> |
| ABT-325 VL | SEQ ID NO.:89 | EIVMTQSPATLSVSPGERAT LSCRASESISSNLAWYQQKP GQAPRLFIYTASTRATDIPA RFSGSGSGTEFTLTISSLQS EDFAVYYCQQYNNWPSITFG QGTRLEIKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE DVD1218HC-LL | SEQ ID NO.:90 | QVQLVESGGGVVQPGRSLRL SCAASGFTFSSYGMRWVRQA PGKGLEWVAFIRYDGSNKYY ADSVKGRFTISRDNSKNTLY LQMNSLRAEDTAVYYCKTHG SHDNWGQGTMVTVSS<u>ASTKG PSVFPLAPEVQLVQSGTEVK KPGESLKISCKGSCYTVTSY WIGWVRQMPGKGLEWMGFIY PGDSETRYSPTFQGQVTISA DKSFNTAFLQWSSLKASDTA MYYCARVGSGWYPYTFDIWG QGTMVTVSS |
| ABT-874 VH | SEQ ID NO.:84 | QVQLVESGGGVVQPGRSLRL SCAASGFTFSSYGMHWVRQA |

TABLE 20-continued

Amino acid sequence of DVD binding proteins capable of binding IL-12 and IL-18

| Protein Protein region | Sequence Identifier | Sequence 12345678901234567890 |
|---|---|---|
| | | PGKGLEWVAFIRYDGSNKYY ADSVKGRFTISRDNSKNTLY LQMNSLRAEDTAVYYCKTHG SHDNWGQGTMVTVSS |
| LINKER | SEQ ID NO.:48 | ASTKGPSVFPLAP |
| ABT-325 VH | SEQ ID NO.:85 | EVQLVQSGTEVKKPGESLKI SCKGSGYTVTSYWIGWVRQM PGKGLEWMGFIYPGDSETRY SPTFQGQVTISADKSFNTAF LQWSSLKASDTAMYYCARVG SGWYPYTFDIWGQGTMVTVS S |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPEAAGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPTEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE DVD1218LC-LL | SEQ ID NO.:91 | QSVLTQPPSVSGAPGQRVTI SCSGSRSNIGSNTVKWYQQL PGTAPKLLIYYNDQRPSGVP DRFSGSKSGTSASLAITGLQ AEDEADYYCQSYDRYTHPAL LFGTGTKVTVLGQPKAAPSV TLFPPEIVMTQSPATLSVSP GERATLSCPASESISSNLAW YQQKPGQAPRLFIYTASTRA TDIPARFSGSGSGTEFTLTI SSLQSEDFAVYYCQQYNNWP SITFGQGTRLEIKR |
| ABT-874 VL | SEQ ID NO.:87 | QSVLTQPPSVSGAPGQRVTI SCSGSRSNIGSNTVKWYQQL PGTAPKLLIYYNDQRPSGVP DRFSGSKSGTSASLAITGLQ AEDEADYYCQSYDRYTHPAL LFGTGTKVTVLG |
| LINKER | SEQ ID NO.:92 | QPKAAPSVTLFPP |
| ABT-325 VL | SEQ ID NO.:89 | EIVMTQSPATLSVSPGERAT LSCRASESISSNLAWYQQKP GQAPRLFIYTASTRATDIPA RFSGSGSGTEFTLTISSLQS EDFAVYYCQQYNNWPSITFG QGTRLEIKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE DVD1812HC-SL | SEQ ID NO.:93 | EVQLVQSGTEVKKPGESLKI SCKGSGYTVTSYWIGWVRQM PGKGLEWMGFIYPGDSETRY SPTFQGQVTISADKSFNTAF |

TABLE 20-continued

Amino acid sequence of DVD binding proteins capable of binding IL-12 and IL-18

| Protein Protein region | Sequence Identifier | Sequence 12345678901234567890 |
|---|---|---|
| | | LQWSSLKASDTAMYYCARVG SGWYPYTFDIWGQGTMVTVS SASTKGPQVQLVESGGGVVQ PGRSLRLSCAASGFTSSYG MHWVRQAPGKGLEWVAFIRY DGSNKYYADSVKGRFTISRD NSKNTLYLQMNSLRAEDTAV YYCKTHGSHDNWGQGTMVTV SS |
| ABT-325 VH | SEQ ID NO.:85 | EVQLVQSGTEVKKPGESLKI SCKGSGYTVTSYWIGWVRQM PGKGLEWMGFIYPGDSETRY SPTFQGQVTISADKSFNTAF LQWSSLKASDTAMYYCARVG SGWYPYTFDIWGQGTMVTVS S |
| LINKER | SEQ ID NO.:42 | ASTKGP |
| ABT-874 VH | SEQ ID NO.:84 | QVQLVESGGGVVQPGRSLRL SCAASGFTSSYGMHWVRQA PGKGLEWVAFIRYDGSNKYY ADSVKGRFTISRDNSKNTLY LQMNSLPAEDTAVYYCKTHG SHDNWGQGTMVTVSS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPEAAGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE DVD1812LC-SL | SEQ ID NO.:94 | EIVMTQSPATLSVSPGERAT LSCPASESISSNLAWYQQKP GQAPRLFIYTASTRATDIPA RFSGSGSGTEFTLTISSLQS EDFAVYYCQQYNNWPSITFG QGTRLEIKRTVAAPQSVLTQ PPSVSGAPGQRVTISCSGSR SNIGSNTVKWYQQLPGTAPK LLIYYNDQRPSGVPDRFSGS KSGTSASLAITGLQAEDEAD YYCQSYDRYTHPALLFGTGT KVTVLG |
| ABT-325 VL | SEQ ID NO.:89 | EIVMTQSPATLSVSPGERAT LSCRASESISSNLAWYQQKP GQAPRLFIYTASTRATDIPA RFSGSGSGTEFTLTISSLQS EDFAVYYCQQYNNWPSITFG QGTRLEIKR |
| LINKER | SEQ ID NO.:44 | TVAAP |
| ABT-874 VL | SEQ ID NO.:87 | QSVLTQPPSVSGAPGQRVTI SCSGSRSNIGSNTVKWYQQL PGTAPKLLIYYNDQRPSGVP DRFSGSKSGTSASLAITGLQ AEDEADYYCQSYDRYTHPAL LFGTGTKVTVLG |

TABLE 20-continued

Amino acid sequence of DVD binding proteins capable of binding IL-12 and IL-18

| Protein Protein region | Sequence Identifier | Sequence 12345678901234567890 |
|---|---|---|
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |
| DVD HEAVY VARIABLE DVD1812HC-LL | SEQ ID NO.:95 | EVQLVQSGTEVKKPGESLKI SCKGSGYTVTSYWIGWVRQM PGKGLEWMGFIYPGDSETRY SPTFQGQVTISADKSFNTAF LQWSSLKASDTAMYYCARVG SGWYPYTFDIWGQGTMVTVS SASTKGPSVFPLAPQVQLVE SGGGVVQPGRSLRLSCAASG FTFSSYGMHWVRQAPGKGLE WVAFIRYDGSNKYYADSVKG RFTISRDNSKNTLYLQMNSL RAEDTAVYYCKTHGSHDNWG QGTMVTVSS |
| ABT-325 VH | SEQ ID NO.:85 | EVQLVQSGTEVKKPGESLKI SCKGSGYTVTSYWIGWVRQM PGKGLEWMGFIYPGDSETRY SPTFQGQVTISADKSFNTAF LQWSSLKASDTAMYYCARVG SGWYPYTFDIWGQGTMVTVS S |
| LINKER | SEQ ID NO.:48 | ASTKGPSVFPLAP |
| ABT-875 VH | SEQ ID NO.:84 | QVQLVESGGGVVQPGRSLRL SCAASGFTFSSYGMHWVRQA PGKGLEWVAFIRYDGSNKYY ADSVKGRFTISRDNSKNTLY LQMNSLRAEDTAVYYCKTHG SHDNWGQGTMVTVSS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| DVD LIGHT VARIABLE DVD1812LC-LL | SEQ ID NO.:96 | EIVMTQSPATLSVPGERAT LSCRASESISSNLAWYQQKP GQAPRLFIYTASTRATDIPA RFSGSGSGTEFTLTISSLQS EDFAVYYCQQYNNWPSITFG QGTRLEIKRTVAAPSVFIFP PQSVLTQPPSVSGAPGQRVT ISCSGSRSNIGSNIVKWYQQ LPGTAPKLLIYYNDQRPSGV PDRFSGSKSGTSASLAITGL QAEDEADYYCQSYDRYTHPA LLFGTGTKVTVLG |
| ABT-325 VL | SEQ ID NO.:89 | EIVMTQSPATLSVPGERAT LSCRASESISSNLAWYQQKP GQAPRLFIYTASTRATDIPA RFSGSGSGTEFTLTISSLQS EDFAVYYCQQYNNWPSITFG QGTRLETKR |
| LINKER | SEQ ID NO.:50 | TVAAPSVFIFPP |
| ABT-874 VL | SEQ ID NO.:87 | QSVLTQPPSVSGAPGQRVTI SCSGSRSNIGSNTVKWYQQL PGTAPKLLIYYNDQRPSGVP DRFSGSKSGTSASLATTGLQ AEDEADYYCQSYDRYTHPAL LFGTGTKVTVLG |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |

Example 3.2

Determination of Antigen Binding Affinity of IL-12/IL-18 DVD Igs

The binding affinity of anti-IL-12/18 DVD-Igs to hIL-12 and hIL-18 were determined by Biacore (Table 21). The neutralization activity against IL-18 was determined by KG-1 assay (Konishi, K., et al.,). Briefly, IL-18 samples (in a final concentration of 2 ng/ml) were pre-incubated with DVD-Ig (in final concentrations between 0 and 10 mg/ml) at 37° C. for 1 hr, and then added to KG-1 cells ($3 \times 10^6$/ml) in RPMI medium containing 10 ng/ml hTNF, followed by incubation at 37° C. for 16-20 hr. The culture supernatants were collected and human IFN-γ production in each sample was determined by ELISA (R&D Systems). Inhibition activities of the DVD molecules against IL-18, presented as $IC_{50}$ values, are shown in Table VI. To determine the inhibition activities of anti-IL-12/18 DVD molecules against IL-12, an IL-12-induced IFN-γ production assay from activated PHA blast cells was employed (D' Andrea, A et al.,) For production of human IFN-γ, PHA blast cells were incubated for 18 hours with human IL-12. Sub-maximal stimulation (55-75% of maximum) was obtained with a human IL-12 concentration of 200 pg/mL. Supernatants were assayed for IFN-γ using a specific human IFN-γ ELISA (Endogen, Cambridge, Mass.). Neutralizing IL-12 DVDs interfere with IL-12 induced IFN-γ production. The neutralization activity of DVD is determined by measuring the DVD concentration required to inhibit 50% of the IFN-γ production by human PHA blast cells, as shown in Table 21.

TABLE 21

Characterization of anti-IL-18/IL-12 DVD-Ig molecules

| MAb | Specif. | $K_d$ (M) | $IC_{50}$ (M) | DVD | Orient. | Linker | Affinity ($K_d$, M) IL-12 | Affinity ($K_d$, M) IL-18 | Potency ($IC_{50}$, M) IL-12 | Potency ($IC_{50}$, M) IL-18 |
|---|---|---|---|---|---|---|---|---|---|---|
| ABT874 | hIL-12 | 6.47E−11 | 5.0E−12 | DVD1218-SL | 12-18-C | short | 3.81E−11 | 6.22E−10 | 6.93E−12 | 1.8E−10 |
|  |  |  |  | DVD1218-LL | 12-18-C | long | 2.38E−11 | 6.64E−10 | 3.04E−12 | 1.8E−10 |
| ABT325 | hIL-18 | 1.37E−10 | 3.0E−10 | DVD1812-SL | 18-12-C | short | 1.82E−09 | 1.91E−10 | 3.66E−10 | 4.0E−11 |
|  |  |  |  | DVD1812-LL | 18-12-C | long | 1.13E−10 | 1.62E−10 | 1.18E−10 | 7.8E−11 |

Affinity (Kd) was determined by Biacore and potency (IC50) determined by KG-1 bioassay (IL-18) and PBMC assay (IL-12).

Table 21 shows the specificity, binding affinity, and neutralization activity of the 2 fully human mAbs used for the construction of the anti-IL-12/IL-18 DVD molecules. As shown in the Table VI, these mAbs have high affinity and neutralization activity. A summary of the characterization of the anti-IL-18/IL-12 DVD constructs is shown in Table VI. SDS-PAGE analysis of all new DVD proteins showed normal migration patterns in both reduced and non-reduced conditions, similar to a regular antibody and DVD1/2-Ig. SEC analysis indicated all molecules were normal, exhibiting peaks in the 200 kD region. The Biacore binding data are consistent with the neutralization activity in the biological assays.

Example 3.3

Biological Activity of Anti-IL-12/IL-18 DVD-Ig in vivo

Both IL-12 and IL-18 are required to produce optimal IFNγ in response to various stimuli.

The biological activity of anti-IL-12/IL-18 DVD-Ig in vivo was determined using the huPBMC-SCID mouse model. In this model, anti-IL-12 antibody (ABT-874) anti-IL-18 antibody (ABT-325) or the anti-IL-12/anti-IL-18 DVD-Ig were injected i.p. or i.v. (250 mg/mouse each) followed by transfer of freshly purified human PBMCs (huPBMC) i.p. into SCID mice. Fifteen minutes later, mice were challenged with dried staphylococcus aureus cells (SAC) to induce human IFNγ production. Animals (n=7-8/group) were sacrificed 18-20 hrs later and serum huIFNγ levels were determined by ELISA. ABT 874 and ABT-325 inhibited SAC-induced IFNγ by approximately 70% which represents maximum IFNγ inhibition with each compound in this model. However, treatment of mice with ABT-874+ABT-325 and anti-IL-12/anti-IL-18 DVD-Ig inhibited IFNγ production by almost 100%. These results suggest that the anti-IL-12/anti-IL-18 DVD-Ig molecule is functionally active in vivo.

Example 3.4

Pharmacokinetic and Pharmacodynamic Studies of Anti-IL-12/IL-18 DVD-Ig

The overall Pharmacokinetic and pharmacodynamic profile of anti-IL-12/IL-18 DVD-Ig was similar to the parent mAbs in mice, i.e 73% bioavailability, comparable to regular IgG. Similar pharmacokinetics, i.e. rapid clearance after day 6-8, was also observed for other mAbs (e.g. human, rat etc,) probably due to anti-human IgG response.

Male SD rats were dosed with anti-IL-12/IL-18 DVD-Ig at 4 mg/kg either i.v. or s.c. The early part of the PK curves looked normal and very similar to those of other human antibodies. An accurate half-life in both groups could not be derived because of the rapid clearance of DVD-Ig beginning on day 6. The sudden drop in DVD-Ig concentration after day 6 may be due to the RAHA response. However, similar profile has also been observed for one of the parent antibodies (ABT-874) used for construction of this DVD-Ig in this particular experiment, as well as other mono-specific human antibodies previously studied. Based on DVD-Ig concentration up to day 6 in both s.c and i.v. groups, bioavailability of DVD-Ig was estimated. Two out of three rats showed 80-95% bioavailability, and the average bioavailability in the three mice was 73%

Example 3.5

Physical/Chemical Characterization of Anti-IL-12/Anti-IL-18 DVD-Ig

Results of physical and chemical characterization of 293 cell-derived, protein A purified, anti-IL-12/anti-IL-18 DVD-Ig are summarized in Table 22.

TABLE 22

Physical/Chemical Characterization of anti-IL-12/anti-IL-18 DVD-Ig

| Parameters Tested | Assay/ Methodology | Findings/ Comments |
|---|---|---|
| Affinity (Kd) |  |  |
| IL-12 | Biacore | 38 pM (65 pM for ABT-874) |
| IL-18 | Biacore | 622 pM (137 pM for ABT-325) |
| Potency (IC50) |  |  |
| IL-12 | PHA-Blast Assay | 7 pM (5 pM for ABT874) |
| IL-18 | KG-1 Assay | 180 pM (300 pM for ABT-325) |
| M.W | MS | HC: 64130 (theo. 64127) LC: 36072 (theo. 36072) |
| Amino acid sequence | Sequencing - MS | All matched |
| Disulfide bonds | Peptide mapping | All 20 disulfide bonds are matched |
| Glycosylation profile |  | Similar to other in-house fully human antibodies - NGA2F and NGA1F observed as the major forms |
| Charge heterogeneity | Cation Exchange (WCX-10) | Homogeneity |
| PI | cIEF | 9.42 (ABT-874: 9.46) |
| Dynamic size | DSL | 7.69 nM (5.34 nM for ABT-325) |
| Purity/ | SDS-PGE | Homogeneity on both reducing (~64 Kd HC and ~36 Kd LC bands) and non-reducing (one band) gels |

TABLE 22-continued

Physical/Chemical Characterization of anti-IL-12/anti-IL-18 DVD-Ig

| Parameters Tested | Assay/ Methodology | Findings/ Comments |
|---|---|---|
| aggregates | SEC | One peak (~100%) observed immediately after protein A purification by SEC |
| | AUC | ~16-17% aggregates observed after 2 cycles of freeze-thaw by AUC |
| Stability (freeze/thaw) | SEC | ~5% aggregates after 2 freeze-thaw cycles, increased to ~13% after additional 10 freeze-thaw cycles. The reason for that is unsolved (process-related, sequence-specific, or LC lamda/kappa hybrid) |
| PK profile | Rat i.v. & s.c. | Similar to (or limited by) parental mAbs. |
| Bioavailability | Rat i.v. vs s.c. | Average 73%; Overall similar to parental mAbs |

Example 3.6

Generation of an Additional Anti-12/anti-18 DVD-Ig (1D4.1-ABT325)

An additional anti-IL-12/IL-18 DVD-Ig molecule with a different parent anti-IL-12 mAb (clone# 1D4.1), as shown in Table 23, was constructed. The 1D4.1-ABT325 DVD-Ig construct was generated with a short linker derived from the N-terminal sequence of human Ck and CH1 domain, as follows:

Short linker: light chain: TVAAP (SEQ ID NO:44); heavy chain: ASTKGP (SEQ ID NO:42).

All heavy and light chain constructs were subcloned into the pBOS expression vector, expressed in COS cells or freestyle 293 cells, and characterized as described above. 1D4.1-ABT325 DVD-Ig fully retains the activities of the two original mAbs (Table 24).

TABLE 23

Amino acid sequence of 1D4.1-ABT325 DVD-Ig

| Protein region | Sequence Identifier | Sequence 12345678901234567890 |
|---|---|---|
| 1D4.1-ABT325 DVD-Ig HEAVY VARIABLE | SEQ ID NO.:114 | EVTLRESGPALVKPTQTLTL TCTFSGFSLSKSVMGVSWIR QPPGKALEWLAHIYWDDDKY YNPSLKSRLTISKDTSKNQV VLTMTNMDPVDTATYYCARR GIRSAMDYWGQGTTVTVSS<u>A</u> <u>STKGP</u>EVQLVQSGTEVKKPG ESLKISCKGSGYTVTSYWIG WVRQMPGKGLEWMGFIYPGD SETRYSPTFQGQVTISADKS FNTAFLQWSSLKASDTAMYY CARVGSGWYPYTFDIWGQGT MVTVSS |
| 1D4.1 VH | SEQ ID NO.:115 | EVTLRESGPALVKPTQTLTL TCTFSGFSLSKSVMGVSWIR QPPGKALEWLAHIYWDDDKY YNPSLKSRLTISKDTSKNQV VLTMTNMDPVDTATYYCARR GIRSAMDYWGQGTTVTVSS |

TABLE 23-continued

Amino acid sequence of 1D4.1-ABT325 DVD-Ig

| Protein region | Sequence Identifier | Sequence 12345678901234567890 |
|---|---|---|
| LINKER | SEQ ID NO.:42 | <u>ASTKGP</u> |
| ABT-325 VH | SEQ ID NO.:85 | EVQLVQSGTEVKKPGESLKI SCKGSGYTVTSYWIGWVRQM PCKGLEWMGFIYPGDSETRY SPTFQGQVTISADKSFNTAF LQWSSLKASDTAMYYCARVG SGWYPYTFDIWGQGTMVTVS S |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPEAAGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| 1D4.1-ABT325 DVD-Ig LIGHT VARIABLE | SEQ ID NO.:116 | DIVMTQSPDSLAVSLGERAT INCKASQSVSNDVAWYQQKP GQPPKLLIYYASNRYTGVPD RFSGSGSGTDFTLTISSLQA EDVAVYYCQQDYNSPWTFGG GTKVEIKR<u>TVAAP</u>EIVMTQS PATLSVSPGERATLSCRASE SISSNLAWYQQKPGQAPRLF IYTASTRATDIPARFSGSGS GTEFTLTISSLQSEDFAVYY CQQYNNWPSITFGQGTRLEI KR |
| 1D4.1 VL | SEQ ID NO.:117 | DIVMTQSPDSLAVSLGERAT INCKASQSVSNDVAWYQQKP GQPPKLLIYYASNRYTGVPD RFSGSGSGTDFTLTISSLQA EDVAVYYCQQDYNSPWTFGG GTKVEIKR |
| LINKER | SEQ ID NO.:44 | <u>TVAAP</u> |
| ABT-325 VL | SEQ ID NO.:89 | EIVMTQSPATLSVSPGERAT LSCRASESISSNLAWYQQKP GQAPRLFIYTASTRATDIPA RFSGSGSGTEFTLTISSLQS EDFAVYYCQQYNNWPSITFG QGTRLEIKR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |

TABLE 24

Characterization 1D4.1-ABT325 DVD-Ig molecule

| mAb | Affinity ($K_d$, M) | | Potency ($IC_{50}$, M) | |
|---|---|---|---|---|
| | IL-12 | IL-18 | IL-12 | IL-18 |
| 1D4.1 | 1.20E−10 | N/A | 4.18E−10 | N/A |
| ABT325 | N/A | 1.91E−10 | N/A | 6.87E−11 |
| 1D4.1-ABT325 DVD-Ig | 1.33E−10 | 1.59E−10 | 2.17E−10 | 1.20E−10 |

Affinity (Kd) was determined by Biacore and potency (IC50) determined by KG-1 bioassay (IL-18) and PBMC assay (IL-12).

Example 4

Generation of Anti-CD20/anti-CD3 DVD-Ig

Anti-CD20/anti-CD3 DVD-Igs were generated using murine anti-human-CD20 (clone 5F1) and anti-human-CD3 (clone OKT3) parent antibodies. The initial constructs included 2 DVD-Igs with different domain orientations. The anti-CD3/anti-CD20 DVD-Ig was constructed in the order of $V_{CD3}$-linker-$V_{CD20}$-constant, and anti-CD20/anti-CD3 DVD-Ig was constructed in the order of $V_{CD20}$-linker-$V_{CD3}$-constant. However, in a preliminary cell surface binding study, anti-CD20 binding activity was diminished in the anti-CD3/anti-CD20 DVD-Ig molecule, even though the anti-CD3 activity was conserved in this design. In contrast, both anti-CD3 and anti-CD20 binding activities were fully conserved in the anti-CD20/anti-CD3 DVD-Ig molecule, indicating this is the optimal domain orientation for these two mAbs/targets combination in a DVD-Ig format. Therefore the anti-CD20/anti-CD3 DVD-Ig construct was chosen for subsequent studies.

The anti-CD20/anti-CD3 DVD-Ig was generated as chimeric Ig i.e the constant region was a human constant region. For binding analysis, human T cell line Jurkat and B cell line Raji were blocked with human IgG and then stained with murine anti-hCD3 mAb OKT3, murine anti-hCD20 mAb 1F5, and anti-CD20/anti-CD3 DVD-Ig. Cells were then washed and stained with FITC-labeled goat anti-murine IgG (with no anti-hIgG cross-reactivity). Anti-CD20/CD3 DVD-Ig bound both T and B cells, whereas CD3 and CD20 mAbs bound only T or B cells, respectively. The amino acid sequence of CD20/CD3 DVD-Ig is disclosed in Table 25.

TABLE 25

Amino acid sequence of CD20CD3DVD-Ig

| Protein Protein region | Sequence Identifier | Sequence |
|---|---|---|
| DVD HEAVY VARIABLE CD20CD3DVD-Ig | SEQ ID NO.:97 | QVQLRQPGAELVKPGASVKM SCKASGYTFTSYNMHWVKQT PGQGLEWIGAIYPGNGDTSY NQKFKGKATLTADKSSSTAY MQLSSLTSEDSAVYYCARSH YGSNYVDYFDYWGQGTTLTV SSAKTTAPSVYPLAPQVQLQ QSGAELARPGASVKMSCKAS GYTFTRYTMHWVKQRPGQGL EWIGYINPSRGYTNYNQKFK DKATLTTDKSSSTAYMQLSS LTSEDSAVYYCARYYDDHYC LDYWGQGTTLTVSS |
| 5F1 VH | SEQ ID NO.:98 | QVQLRQPGAELVKPGASVKM SCKASGYTFTSYNMHWVKQT PGQGLEWIGAIYPGNGDTSY NQKFKGKATLTADKSSSTAY MQLSSLTSEDSAVYYCARSH YGSNYVDYFDYWGQGTTLTV SS |
| LINKER | SEQ ID NO.:99 | AKTTAPSVYPLAP |
| OKT3 VH | SEQ ID NO.:100 | QVQLQQSGAELARPGASVKM SCKASGYTFTRYTMHWVKQR PGQGLEWIGYINPSRGYTNY NQKFKDKATLTTDKSSSTAY MQLSSLTSEDSAVYYCARYY DDHYCLDYWGQGTTLTVSS |
| CH | SEQ ID NO.:34 | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYTLPPSREE MTKNQVSLTCLVKGFYPSDI AVEWESNGQPENNYKTTPPV LDSDGSFFLYSKLTVDKSRW QQGNVFSCSVMHEALHNHYT QKSLSLSPGK |
| CD20CD3DVD-Ig LIGHT VARIABLE | SEQ ID NO.:101 | QIVLSQSPAILSASPGEKVT MTCRASSSLSFMHWYQQKPG SSPKPWIYATSNLASGVPAR FSGSGSGTSYSLTISRVEAE DAATYFCHQWSSNPLTFGAG TKLELKRADAAPTVSIFPPQ IVLTQSPAIMSASPGEKVTM TCSASSSVSYMNWYQQKSGT SPKRWIYDTSKLASGVPAHF RGSGSGTSYSLTISGMEAED AATYYCQQWSSNPFTFGSGT KLEINR |
| 5F1 VL | SEQ ID NO.:102 | QIVLSQSPAILSASPGEKVT MTCRASSSLSFMHWYQQKPG SSPKPWIYATSNLASGVPAR FSGSGSGTSYSLTISRVEAE DAATYFCHQWSSNPLTFGAG TKLELKR |
| LINKER | SEQ ID NO.:103 | ADAAPTVSIFPP |
| OKT3 VL | SEQ ID NO.:104 | QIVLTQSPAIMSASPGEKVT MTCSASSSVSYMNWYQQKSG TSPKRWIYDTSKLASGVPAH FRGSGSGTSYSLTISGMEAE DAATYYCQQWSSNPFTFCSG TKLEINR |
| CL | SEQ ID NO.:36 | TVAAPSVFIFPPSDEQLKSG TASVVCLLNNFYPREAKVQW KVDNALQSGNSQESVTEQDS KDSTYSLSSTLTLSKADYEK HKVYACEVTHQGLSSPVTKS FNRGEC |

Example 5

Generation of mIL-1α/βDVD-Ig

To study key issues concerning pharmacokinetics, in vivo efficacy, tissue penetration, and immunogenicity of DVD-Ig molecules, mouse-anti-mouse IL-1α/βDVD-Ig molecules were constructed as described below.

Example 5.1

Construction of mIL-1α/βDVD-Ig

Mouse-anti-mouse L-1α/βDVD-Ig molecules were constructed using two mouse anti-mouse IL-1α/β mAbs (9H10 and 10G11) generated from IL-1α/β double KO mice. Mouse anti-mouse IL-1α, and mouse anti-mouse IL-1β, monoclonal antibodies were generated by immunizing IL-1α/β double KO mice with mouse IL-1α, or mouse IL-1β, respectively. One mouse anti-mouse IL-1α (Clone 9H10), and one mouse anti-mouse IL-1β mAb (clone 10G11), were selected and used to generate mIL-1α/β DVD-Ig molecules. Various linker sizes and different domain orientations were tested. The final functional mIL-1α/β DVD-Ig molecules was constructed in a orientation of V(anti-mIL-1β)-linker-V(anti-mIL-1β)-murine constant region (Cγ2a and Cκ). The cloning, expression, and purification procedures were similar to that of the hIL-1α/β DVD-Ig. The cloning of mIL-1α/β DVD-Ig was carried out using similar overlapping PCR and homologous recombination as described for hIL-1α/β DVD3-Ig. The sequences of IL-1α/β DVD-Ig are shown below in Table 26:

TABLE 26

Amino acid sequence of mIL-1α/βDVD-Ig

| Protein Protein region | Sequence Identifier | Sequence 12345678901234567890 |
|---|---|---|
| mIL-1α/β DVD-Ig HEAVY VARIABLE | SEQ ID NO.:105 | EVQLQQSGPELVKPGTSVKM SCKTSGYTFTSYVMHWVKQK PGQGLEWIGYIIPYNDNTKY NEKFKGKATLTSDKSSSTAY MELSSLTSEDSAVYYCARRN EYYGSSFFDYWGQGTTLTVS SAKTTAPSVYPLAPQVILKE SGPGILQPSQTLSLTCSFSG FSLSTYGTAVNWIRQPSGKG LEWLAQIGSDDRKLYNPFLK SRITLSEDTSNSQVFLKITS VDTEDSATYYCANGVMEYWG LGTSVTVSS |
| 10G11 VH | SEQ ID NO.:106 | EVQLQQSGPELVKPGTSVKM SCKTSGYTFTSYVMHWVKQK PGQGLEWIGYIIPYNDNTKY NEKFKGKATLTSDKSSSTAY MELSSLTSEDSAVYYCARRN EYYGSSFFDYWGQGTTLTVS S |
| LINKER | SEQ ID NO.:99 | AKTTAPSVYPLAP |
| 9H10 VH | SEQ ID NO.:107 | QVILKESGPGILQPSQTLSL TCSFSGFSLSTYGTAVNWIR QPSGKGLEWLAQIGSDDRKL YNPFLKSRITLSEDTSNSQV FLKITSVDTEDSATYYCANG VMEYWGLGTSVTVSS |
| CH | SEQ ID NO.:108 | AKTTAPSVYPLAPVCGDTTG SSVTLGCLVKCYFPEPVTLT WNSGSLSSGVHTFPAVLQSD LYTLSSSVTVTSSTWPSQSI |

TABLE 26-continued

Amino acid sequence of mIL-1α/βDVD-Ig

| Protein Protein region | Sequence Identifier | Sequence 12345678901234567890 |
|---|---|---|
| | | TCNVAHPASSTKVDKKIEPR GPTIKPCPPCKCPAPNLLGG PSVFIFPPKIKDVLMISLSP IVTCVVVDVSEDDPDVQISW FVNNVEVHTAQTQTHREDYN STLRVVSALPIQHQDWMSGK EFKCKVNNKDLPAPIERTIS KPKGSVPAPQVYVLPPPEEE MTKKQVTLTCMVTDFMPEDI YVEWTNNGKTELNYKNTEPV LDSDGSYFMYSKLRVEKKNW VERNSYSCSVVHEGLHNHHT TKSFSRTPGK |
| mIL-1α/β DVD-Ig LIGHT VARIABLE | SEQ ID NO.:109 | DIQMTQSPASLSASVGETVT ITCRGSGILHNYLVWYQQKQ GKSPQLLVYSAKILADGVPS RFSCSCSGTQYSLKINSLQP EDFGSYYCQHFWSTPFTFGS GTKLEIKRADAAPTVSIFPP SIVMTQTPKFLLVSAGDRVT ITCKASQSVNHDVAWYQQMP GQSPKLLIYFASNRYTGVPD RFTGSGYGTDFTFTISTVQA EDLAVYFCQQDYSSPYTFGG GTKLEIKR |
| 10G11 VL | SEQ ID NO.:110 | DIQMTQSPASLSASVGETVT ITCRGSGILHNYLVWYQQKQ GKSPQLLVYSAKILADGVPS RFSGSGSGTQYSLKINSLQP EDFGSYYCQHFWSTPFTFGS GTKLEIKR |
| LINKER | SEQ ID NO.:111 | ADAAPTVSIFPP |
| 9H10 VL | SEQ ID NO.:112 | SIVMTQTPKFLLVSAGDRVT ITCKASQSVNHDVAWYQQMP GQSPKLLIYFASNRYTGVPD RFTGSGYGTDFTFTISTVQA EDLAVYFCQQDYSSPYTFGG GTKLEIKR |
| CL | SEQ ID NO.:113 | ADAAPTVSIFPPSSEQLTSG GASVVCFLNNFYPKDINVKW KIDGSERQNGVLNSWTDQDS KDSTYSMSSTLTLTKDEYER HNSYTCEATHKTSTSPIVKS FNRNEC |

Murine mIL-1α/βDVD-Ig retained affinity/in vitro potency against both IL-1α and IL-1β. Table 27 shows the characterization of mAbs 9H10 (anti-mIL-1α), 10G11 (anti-mIL-1β), and mIL-1α/β DVD-Ig.

TABLE 27

Characterization of mDVD4-Ig

| | Antigen | $K_D$ (M) | $IC_{50}$ (M) |
|---|---|---|---|
| 9H10 | mIL-1α | 1.73E-10 | 2.00E-10 |
| 10G11 | mIL-1β | 2.30E-10 | 3.70E-10 |
| mIL-1α/βDVD-Ig | mIL-1α | 7.66E-10 | 2.00E-09 |
| | mIL-1β | 6.94E-10 | 8.00E-10 |

Example 5.2

In vivo Activity of mIL-1α/βDVD-Ig in Arthritis Model

The therapeutic effects of anti-L-1alpha, anti-L-1beta, combined anti-IL-1-alpha/anti-IL-1beta, and murine anti-IL-1alpha/beta DVD4-Ig, were evaluated in a collagen-induced arthritis mouse model well known in the art. Briefly, male DBA-1 mice were immunized with bovine type II collagen in CFA at the base of the tail. The mice were boosted with Zymosan intraperitoneally (i.p) at day 21. After disease onset at day 24-27, mice were selected and divided into separate groups of 10 mice each. The mean arthritis score of the control group, and anti-cytokine groups was comparable at the start of treatment. To neutralize IL-1, mice were injected every other day with 1-3 mg/kg of anti-IL-1alpha mAb, anti-IL-1beta mAb, combination of anti-IL-1-alpha/anti-IL-beta mAbs, or murine anti-IL-1alpha/beta DVD4-Ig intraperitoneally. Mice were carefully examined three times a week for the visual appearance of arthritis in peripheral joints, and scores for disease activity determined.

Blockade of IL-1 in the therapeutic mode effectively reduced the severity of arthritis, with anti-IL-1beta showing greater efficacy (24% reduction in mean arthritis score compared to control group) than anti-IL-1-alpha (10% reduction). An additive effect was observed between anti-IL-1-alpha and anti-IL-1beta, with a 40% reduction in mean arthritis score in mice treated with both anti-IL-1alpha and anti-IL-1beta mAbs. Surprisingly, at the same dose level, the treatment of mDVD-Ig exhibited 47% reduction in mean arthritis score, demonstrating the in vivo therapeutic efficacy of mDVD-Ig. Similar efficacy weas also observed in the measurements of joint swelling in this animal model.

The present invention incorporates by reference in their entirety techniques well known in the field of molecular biology and drug delivery. These techniques include, but are not limited to, techniques described in the following publications:

Ausubel et al. (eds.), *Current Protocols in Molecular Biology*, John Wiley & Sons, NY (1993);
Ausubel, F. M. et al. eds., *Short Protocols In Molecular Biology* (4th Ed. 1999) John Wiley & Sons, NY. (ISBN 0-471-32938-X).
*Controlled Drug Bioavailability, Drug Product Design and Performance*, Smolen and Ball (eds.), Wiley, New York (1984);
Giege, R. and Ducruix, A. Barrett, *Crystallization of Nucleic Acids and Proteins*, a Practical Approach, 2nd ea., pp. 20 1-16, Oxford University Press, New York, N.Y., (1999);
Goodson, in *Medical Applications of Controlled Release*, vol. 2, pp. 115-138 (1984);
Hammerling, et al., in: *Monoclonal Antibodies and T-Cell Hybridomas* 563-681 (Elsevier, N.Y., 1981;
Harlow et al., *Antibodies: A Laboratory Manual*, (Cold Spring Harbor Laboratory Press, 2nd ed. 1988);
Kabat et al., *Sequences of Proteins of Immunological Interest* (National Institutes of Health, Bethesda, Md. (1987) and (1991);
Kabat, E. A., et al. (1991) *Sequences of Proteins of Immunological Interest*, Fifth Edition, U.S. Department of Health and Human Services, NIH Publication No. 91-3242;
Kontermann and Dubel eds., *Antibody Engineering* (2001) Springer-Verlag. New York. 790 pp. (ISBN 3-540-41354-5).
Kriegler, Gene Transfer and Expression, A Laboratory Manual, Stockton Press, NY (1990);
Lu and Weiner eds., *Cloning and Expression Vectors for Gene Function Analysis* (2001) BioTechniques Press. Westborough, Mass. 298 pp. (ISBN 1-881299-21-X).
*Medical Applications of Controlled Release*, Langer and Wise (eds.), CRC Pres., Boca Raton, Fla. (1974);
Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).
Sambrook, J. et al. eds., *Molecular Cloning: A Laboratory Manual* (2d Ed. 1989) Cold Spring Harbor Laboratory Press, NY. Vols. 1-3. (ISBN 0-87969-309-6).
*Sustained and Controlled Release Drug Delivery Systems*, J. R. Robinson, ed., Marcel Dekker, Inc., New York, 1978
Winnacker, E. L. *From Genes To Clones: Introduction To Gene Technology* (1987) VCH Publishers, NY (translated by Horst Ibelgaufts). 634 pp. (ISBN 0-89573-614-4).

REFERENCES

US Patents:
U.S. Pat. Nos. 4,526,938; 4,753,894; 4,816,567; 4,880,078; 4,943,533; 4,946,778; 4,980,286; 5,500,362; 5,916,597; 5,985,309; 5,128,326; 5,223,409; 5,225,539; 5,258,498; 5,290,540; 5,403,484; 5,427,908; 5,516,637; 5,530,101; 5,558,864; 5,565,332; 5,571,698; 5,580,717; 5,585,089; 5,624,821; 5,627,052; 5,641,870; 5,648,260; 5,658,727; 5,677,171; 5,679,377; 5,693,762; 5,698,426; 5,714,350; 5,714,352; 5,723,323; 5,733,743; 5,736,137; 5,750,753; 5,763,192; 5,766,886; 5,780,225; 5,814,476; 5,817,483; 5,821,047; 5,824,514; 5,855,913; 5,874,064; 5,891,996; 5,912,015; 5,916,771; 5,934,272; 5,939,598; 5,969,108; 5,976,862; 5,985,320; 5,985,309; 5,985,615; 5,989,463; 5,998,209; 6,019,968; 6,075,181; 6,091,001; 6,114,598; 6,130,364; 6,180,370; 6,204,023; 6,235,883; 6,258,562 6,350,861; 6,506,883; 6,699,658; 6,914,128

US Patent Applications:
Ser. No. 10/172,317
Ser. No. 09/428,082

US Patent Application Publication
20020137134; 20030186374; 20040018590; 20050147610 A1; 20050042664 A1; 2006104968;

Foreign Patent Documents
PCT/GB91/01134; PCT/US2003/040426 PCT/US91/05939; PCT/US91/09630; PCT/US94/01234; PCT/US96/18978; PCT/US98/16280; WO 00 09560; WO 00/037504; WO 00/56772; WO 01/58956; WO 01/77342 WO 01/83525; WO 01/88138; WO 0162931A2; WO 0177342A1; WO 02/02773; WO 02072636; WO 03/035835; WO 90/02809; WO 90/05144 A1; WO 91/05548; WO 91/09967; WO 91/10737; WO 91/10741; WO 91/17271; WO 92/01047; WO 92/02551 WO 92/09690; WO 92/15679; WO 92/18619; WO 92/19244; WO 92/20791; WO 92/22324 WO 93/01288; WO 93/11236; WO 94/02602; WO 95/15982; WO 95/20045 WO 95/20401; WO 96/20698; WO 96/33735; WO 96/34096; WO 96/40210; WO 97/29131; WO 97/32572; WO 97/44013; WO 98/16654; WO 98/24893; WO 98/31346; WO 98/31700; WO 98/50433; WO 99/15154; WO 99/20253; WO 99/25044; WO 99/45031; WO 99/53049; WO 99/54342; WO 99/66903; WO00/56772A1; WO2001/077342(A1); WO2002097048A2; WO2003016466A2; WO2004078140; WO2005100584 A2 WO90/14424; WO90/14430; WO90/14443; WO9524918 A1; EP 1,176, 195; EP 229,246; EP 239,400; EP 519,596; EP 519,596; EP 592,106; GB89/01334; GB91/01134; GB92/01755.

OTHER REFERENCES

Ames et al., J. Immunol. Methods 184:177-186 (1995);
Aoji et al., 2005 J Am Coll Cardiol. 45(10):1574-9;
Arancio O, et al., EMBO Journal (2004) 1-10;
Arndt, M. and J. Krauss, Methods Mol Biol, 2003. 207: p. 305-21;
Azzazy H., and Highsmith W. E., (2002) Clin. Biochem. 35:425-445;
Babcock, J. S. et al. (1996) Proc. Natl. Acad. Sci. USA 93:7843-7848;
Barbas et al. (1991) PNAS 88:7978-7982;
Barbas et al. Proc Nat. Acad. Sci, USA 91:3809-3813 (1994);
Barry J. Dickson, Science. (2002) 298:1959;
Better et al., Science 240:1041-1043 (1988);
Biewenga et al 1983 Clin Exp Immunol 51: 395-400;
Bird et al. (1988) Science 242:423-426;
Bornemann K D, et al., Am J Pathol. 2001; 158:63;
Boyce et al., Journal of Experimental Medicine (2005), 201 (12), 1869-1873;
Brand D D. (2005) Comp Med. 55(2):114-22;
Brennan, M., et al., Science, (1985). 229(4708): p. 81-3;
Brinkman et al., J. Immunol. Methods 182:41-50 (1995);
Buchwald et al., 1980, Surgery 88:507;
Buras J A, et al.,(2005) Nat Rev Drug Discov. 4(10):854-65;
Burke, Sandra E., et al., Advanced Drug Delivery Reviews (2006), 58(3), 437-446;
Burton et al., Advances in Immunology 57:191-280 (1994);
C. E. Shepherd, et al., Neurobiol Aging. 2005 Oct. 24;
Calandra T, et al., (2000) Nat Med. 6(2): 164-70;
Carter et al., Proc. Natl. Acad. Sci. U.S.A. 89:4285 (1992);
Chothia &Lesk, J. Mol. Biol. 196:901-917 (1987);
Chothia et al., Nature 342:877-883 (1989);
Clackson et al. (1991) Nature 352:624-628;
Cleek et al., 1997, Pro. Int'l. Symp. Control. Rel. Bioact. Mater. 24:853-854;
Co, M. S., et al., Mol. Immunol. (1993) 30:1361-1367;
Coffman, et al., Journal of Experimental Medicine (2005), 201(12), 1875-1879;
Dall' Acqua 1998 Biochemistry 37: 9266-73;
D'Andrea, A., et al., J Exp Med, 1992. 176(5): p. 1387-98;
Deane R, et al., Nat Med. 2003; 9:907-13;
Descotes J, et al., Developments in biological standardization (1992), 77 99-102;
Dinarello, C. A., K. Muegge, and S. K. Durum. 2000. Current Protocols in Immunology 6:1
During et al., 1989, Ann. Neurol. 25:351;
Durocher et al., Nucleic Acids Research 2002, Vol 30, No. 2;
Economides, A. N., et al., Nat Med, 2003. 9(1): p. 47-52;
Eliezer Masliah, et al., Neuron. 2005: 46:857;
Felicia Yu Hsuan Teng, et al., J Neurosci Res. (2005) 79:273;
Finotto et al., International Immunology (2005), 17(8), 993-1007;
Fuchs et al. (1991) Bio/Technology 9:1370-1372;
Gang Xu, et al., J. Neurochem. 2004; 91; 1018;
Garrad et al. (1991) Bio/Technology 9:1373-1377;
Gavilondo J. V., and Larrick J. W. (2002) BioTechniques 29:128-145;
Genain C P, et al., (1997) J Mol Med. 75(3):187-97;
Genovese Mc et al 2005 N Engl J Med. 353:1114-23;
Glennie, M. J., et al., J Immunol, 1987. 139(7): p. 2367-75;
Goldspiel et al., 1993, Clinical Pharmacy 12:488-505;
Gracie, J. A., et al., J Clin Invest, 1999. 104(10): p. 1393-401;
Gram et al. (1992) PNAS 89:3576-3580;
Green and Jakobovits J. Exp. Med. 188:483-495 (1998);
Green et al. Nature Genetics 7:13-21 (1994);
Griffin (2000) JI 164:4433;
Griffiths et al. (1993) EMBO J. 12:725-734;
Harriman G, Harper L K, Schaible T F. 1999 Ann Rheum Dis 58 Suppl 1:I 61-4;
Hart et al., Journal of Allergy and Clinical Immunology (2001), 108(2), 250-257);
Hawkins et al. (1992) J Mol Biol 226:889-896;
Hay et al. (1992) Hum Antibod Hybridomas 3:81-85;
Hildebrand, H. F., et al., Surface and Coatings Technology (2006), 200(22-23), 6318-6324;
Holliger, P. and G. Winter, Cancer Immunol Immunother, 1997. 45(3-4): p. 128-30;
Holliger, P., et al. (1993) Proc. Natl. Acad. Sci. USA 90:6444-6448;
Holliger, P., T. Prospero, and G. Winter, Proc Natl Acad Sci USA, 1993. 90(14): p. 6444-8;
Hoogenboom et al. (1991) Nuc Acid Res 19:4133-4137;
Hoogenboom H., and Chames P. (2000) Immunology Today 21:371-378;
Hoogenboom H. R., (1997) TIB Tech. 15:62-70;
Howard et al., 1989, J. Neurosurg. 7 1:105);
Huber et al. Nature; 264: 415-20; Thies et al 1999 J Mol Biol; 293: 67-79;
Huse et al. (1989) Science 246:1275-1281;
Huston et al. (1988) Proc. Natl. Acad. Sci. USA 85:5879-5883;
Huston et al., Methods in Enzymology 203:46-88 (1991);
Hwang 2002 JI 169:633;
Igor Klyubin, et al., Nat Med. 2005, 11:556-61;
Ito, A., et al., J Immunol, 2003. 170(9): p. 4802-9;
Jackson et al., J. Immunol. 154(7):3310-9 (1995);
Johnnson, B., et al. (1991) Anal. Biochem. 198:268-277;
Johnsson, B., et al. (1995) J. Mol. Recognit. 8:125-131;
Joliot et al., 1991, Proc. Natl. Acad. Sci. USA 88:1864-1868;
Jones et al., Nature 321:522 (1986);
Jones R. 2000 IDrugs. 3(4):442-6;
Jönsson, U., et al. (1991) Biotechniques 11:620-627;
Jönsson, U., et al. (1993) Ann. Biol. Clin. 51:19-26;
Joosten, L. A., et al., Arthritis Rheum, 1996. 39(5): p. 797-809;
Jungbluth et al. 2003, Proc Natl Acad Sci USA. 100(2):639-44);
Kabat et al. (1971) Ann. NY Acad, Sci. 190:382-391;
Karni, A., et al., J Neuroimmunol, 2002. 125(1-2): p. 134-40;
Kellermann S-A., and Green L. L. (2002) Current Opinion in Biotechnology 13:593-597;
Kettleborough et al., 1991, Protein Eng. 4(7):773-83);
Kettleborough et al., Eur. J. Immunol. 24:952-958 (1994);
Kim et al 1994 Eur J Immunol; 24: 542-548;
Kipriyanov, S. M., et al., Int J Cancer, 1998. 77(5): p. 763-72;
Konishi, K., et al., J Immunol Methods, 1997. 209(2): p. 187-91;
Kostelny, S. A., M. S. Cole, and J. Y. Tso, J Immunol, 1992. 148(5): p. 1547-53;
Kriangkum, J., et al., Biomol Eng, 2001. 18(2): p. 31-40;
Lam et al., 1997, Proc. Int'l. Symp. Control Rel. Bioact. Mater. 24:759-760;
Langer (1990), Science 249:1527-1533;
Le Gall, F., et al., FEBS Lett, 1999. 453(1-2): p. 164-8;
Le Gall, F., et al., J Immunol Methods, 2004. 285(1): p. 111-27;
Leung, B. P., et al., J Immunol, 2000. 164(12): p. 6495-502;
Levy et al., 1985, Science 228:190;
Little M. et al (2000) Immunology Today 21:364-370;

Lloyd, Clare M., et al., Advances in Immunology (2001), 77 263-295;
Lu, D., et al., J Biol Chem, 2004. 279(4): p. 2856-65;
Lublin FD., et al., (1985) Springer Semin Immunopathol. 8(3):197-208;
Luster et al., Toxicology (1994), 92(1-3), 22943;
MacCallum, J Mol Biol 262(5):732-45 (1996);
Mack, M., et al., Proc Natl Acad Sci USA, 1995. 92(15): p. 7021-5;
Marchalonis et al., Adv Exp Med Biol. 484:13-30 (2001);
Marco Domeniconi, et al., J Neurol Sci. 2005, 233:43;
Marks et al. BioTechnology 10:779-783 (1992);
Marques, A. P., et al., Biodegradable Systems in Tissue Engineering and Regenerative Medicine (2005), 377-397;
Mateo et al, 1997, Immunotechnology, 3(1):71-81);
May, 1993, TIBTECH 11(5):155-215;
McCafferty et al., Nature (1990) 348:552-554;
McDonnell, et al., Progress in Respiratory Research (2001), 31(New Drugs for Asthma, Allergy and COPD), 247-250;
McGee A W, et al., Trends Neurosci. 2003, 26:193;
McIntosh, J. K., et al., J Immunol, 1989. 143(1): p. 162-7;
Mendez et al., Nature Genetics 15:146-156 (1997);
Merchant, A. M., et al., Nat Biotechnol, 1998. 16(7): p. 677-81;
Michelle C Janelsins, et al., J Neuroinflammation. 2005; 2:23;
Milan Makwanal, et al., FEBS J. 2005, 272:2628;
Miller, K., et al., J Immunol, 2003. 170(9): p. 4854-61;
Milstein, C. and A. C. Cuello, Nature, 1983. 305(5934): p. 537-40;
Mizushima, S. and Nagata, S., (1990) Nucleic acids Research Vol 18, No. 17;
Modjtahedi et al, 1996, Br J Cancer, 73(2):228-35;
Modjtahedi et al, 2003, Int J Cancer, 105(2):273-80;
Modjtahedi et al., 1993, Br J Cancer. 1993, 67(2):247-53;
Modjtahedi et al., 1993, J. Cell Biophys. 1993, 22(1-3):129-46;
Morgan and Anderson, 1993, Ann. Rev. Biochem. 62:191-217;
Mulligan, Science 260:926-932 (1993);
Mullinax et al., BioTechniques 12(6):864-869 (1992);
Murthy et al. 1987, Arch Biochem Biophys. 252(2):549-60;
Nakanishi, K., et al., Annu Rev Immunol, 2001. 19: p. 423-74;
Nelson R B, Curr Pharm Des. 2005; 11:3335;
Ning et al., 1996, Radiotherapy &Oncology 39:179-189;
Okamoto H, Kamatani N. 2004. N Engl J. Med. 351:1909;
Owens T, et al., (1995) Neurol Clin. 13(1):51-73;
Padilla et al., Journal of Immunology (2005), 174(12), 8097-8105;
Padlan, FASEB J. 9:133-139 (1995);
Padlan, Molecular Immunology 28(4/5):489-498 (1991);
Peipp, M. and T. Valerius, Biochem Soc Trans, 2002. 30(4): p. 507-11;
Péng SL (2004) Methods Mol Med.; 102: 227-72;
Persic et al., Gene 187 9-18 (1997);
Pluckthun, A. and P. Pack, Immunotechnology, 1997. 3(2): p. 83-105;
Poljak, R. J., et al. (1994) Structure 2:1121-1123;
Presta et al., J. Immunol. 151:2623 (1993),
Presta LG. 2005 J Allergy Clin Immunol. 116:731-6;
R. Jefferis, Biotechnol. Prog. 21 (2005), pp. 11-16;
R. J. Kaufman and P.A. Sharp (1982) Mol. Biol. 159:601-621;
Ranger and Peppas, 1983, J., Macromol. Sci. Rev. Macromol. Chem. 23:61;
Ridgway, J. B., et al., Protein Eng, 1996. 9(7): p. 617-21;
Riechmann et al., Nature 332:323 (1988);
Roberts, R. W. and Szostak, J. W. (1997) Proc. Natl. Acad. Sci. USA 94:12297-12302;
Rodeck et al., 1987, J Cell Biochem. 35(4):315-20;
Roguska et al., PNAS 91:969-973 (1994);
Saudek et al., 1989, N. Engl. J. Med. 321:574;
Sawai et al., AJRI 34:26-34 (1995);
Schier et al. Gene 169:147-155 (1995);
Sefton, 1987, CRC Crit. Ref. Biomed. Eng. 14:20;
Seligman 1978 Ann Immunol 129: 855-70;
Sfikakis P P et al (2005) Curr Opin Rheumatol 17:550-7;
Shapiro et al., Crit. Rev. Immunol. 22(3): 183-200 (2002);
Shields, R. L. et al. (2002) J. Biol. Chem. 277:26733-26740;
Shu et al., PNAS 90:7995-7999 (1993);
Sims et al., J. Immunol. 151: 2296 (1993);
Skerra et al., Science 240:1038-1040 (1988);
Snibson K J; et al., Journal of the British Society for Allergy and Clinical Immunology (2005), 35(2), 146-52;
Soloman B, Curr Alzheimer Res. 2004; 1: 149;
Song et al., 1995, PDA Journal of Pharmaceutical Science &Technology 50:372-397;
Staerz, U. D., et al., Nature, 1985. 314(6012): p. 628-31;
Steinman L, et al., (2005) Trends Immunol. 26(11):565-71;
Studnicka et al., Protein Engineering 7(6):805-814 (1994);
't Hart B A, et al., (2005) J Immunol 175(7):4761-8;
Tara Karnezis, et al., Nature Neuroscience (2004) 7, 736;
Taylor, L. D., et al. (1992) Nucl. Acids Res. 20:6287-6295;
Tolstoshev, 1993, Ann. Rev. Pharmacol. Toxicol. 32:573-596;
Tuohy V K, et al., (1999) J Exp Med. 189(7): 1033-42;
Umana et al. (1999) Nat. Biotech. 17:176-1;
Urlaub and Chasin, (1980) Proc. Natl. Acad. Sci. USA 77:4216-4220;
Verhoeyen et al., Science 239:1534 (1988)),
von Mehren M, et al (2003) Annu Rev Med.; 54:343-69;
Wallick, S. C., et al., Exp. Med. (1988) 168:1099-1109;
Ward et al., (1989) Nature 341:544-546;
West et al. 2000 Biochemistry 39: 9698-708;
William L. Klein, Neurochem Int. 2002; 41:345;
Wright, A., et al., EMBO J. (1991) 10:2717 2723;
Wu and Wu, 1991, Biotherapy 3:87-95;
Wu and Wu, J. Biol. Chem. 262:4429-4432 (1987);
Wu, A. M., et al., Immunotechnology, 1996. 2(1): p. 21-36;
Wu, A. M., et al., Immunotechnology, 1996. 2(1): p. 21-36;
Wu, Peng; Grainger, David W., Biomaterials (2006), 27(11), 2450-2467;
Yelton et al. J. Immunol. 155:1994-2004 (1995);
Zapata et al. Protein Eng. 8(10): 1057-1062 (1995);

Although a number of embodiments and features have been described above, it will be understood by those skilled in the art that modifications and variations of the described embodiments and features may be made without departing from the present disclosure or the invention as defined in the appended claims. Each of the publications mentioned herein is incorporated by reference.

We claim:

1. A binding protein comprising four polypeptide chains, wherein two polypeptide chains comprise VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, and X2 is an Fc region; and two polypeptide chains comprise VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1; wherein said four polypeptide chains of said binding protein form four functional antigen binding sites.

2. The binding protein according to claim 1, wherein said binding protein is capable of binding one or more targets.

3. The binding protein according to claim 2, wherein said one or more targets is selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAI1; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYD1); CX3CR1 (V28); CXCL1 (GRO1); CXCL10(IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2;

F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; HLA-A; HLA-DRA; HM74; HMOX1; HUMCYT2A; ICEBERG; ICOSL; ID2; IFN-a; IFNA1; IFNA2; IFNA4; IFNA5; IFNA6; IFNA7; IFNB1; IFN-gamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NRII2; NRII3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; SI00A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP10; TDGF1; TEK; TGFA; TGFB1; TGFB1I1; TGFB2; TGFB3; TGFBI; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCR1 (GPR5/CCXCR1); YY1; and ZFPM2.

4. The binding protein according to claim 1, wherein said binding protein is capable of binding a two targets, wherein the two targets are selected from the group consisting of CD138 and CD20; CD138 and CD40; CD20 and CD3; CD38 & CD138; CD38 and CD20; CD38 and CD40; CD40 and CD20; CD19 and CD20; CD-8 and IL-6; PDL-1 and CTLA-4; CTLA-4 and BTNO2; CSPGs and RGM A; IGF1 and IGF2; IGF1/2 and Erb2B; IL-12 and IL-18; IL-12 and TWEAK; IL-13 and ADAM8; IL-13 and CL25; IL-13 and IL-1beta; IL-13 and IL-25; IL-13 and IL-4; IL-13 and IL-5; IL-13 and IL-9; IL-13 and LHR agonist; IL-13 and MDC; IL-13 and MIF; IL-13 and PED2; IL-13 and SPRR2a; IL-13 and SPRR2b; IL-13 and TARC; IL-13 and TGF-β; IL-1α and IL-1β; MAG and RGM A; NgR and RGM A; NogoA and RGM A; OMGp and RGM A; RGM A and RGM B; Te38 and TNFα; TNFα and IL-12; TNFα and IL-12p40; TNFα and IL-13; TNFα and IL-15; TNFα and IL-17; TNFα and IL-18; TNFα and IL-1beta; TNFα and IL-23; TNFα and MIF; TNFα and PEG2; TNFα and PGE4; TNFα and VEGF; and VEGFR and EGFR; TNFα and RANK ligand; TNFα and Blys; TNFα and GP130; TNFα and CD-22; and TNFα and CTLA-4.

5. The binding protein according to claim 2, wherein the binding protein is capable of modulating a biological function of one or more targets.

6. The binding protein according to claim 2, wherein the binding protein is capable of neutralizing one or more targets.

7. The binding protein according to claim 2, wherein said one or more targets is selected from the group consisting of cytokine, chemokine, cell surface protein, enzyme and receptor.

8. The binding protein according to claim 7 wherein the cytokine is selected from the group consisting of lymphokines, monokines, and polypeptide hormones.

9. The binding protein according to claim 8, wherein said cytokines are IL-1α and IL-1β.

10. The binding protein according to claim 9, wherein the binding protein comprises a DVD heavy chain amino acid sequence selected from the group consisting of SEQ ID NO. 33, SEQ ID NO. 37, SEQ ID NO. 41, SEQ ID NO. 45, SEQ ID NO. 47, SEQ ID NO. 51, SEQ ID NO. 53, SEQ ID NO. 55, SEQ ID NO. 57, and SEQ ID NO. 59; and a DVD light chain amino acid sequence selected from the group consisting of SEQ ID NO. 35, SEQ ID NO. 39, SEQ ID NO. 43, SEQ ID NO. 46, SEQ ID NO. 49, SEQ ID NO. 52, SEQ ID NO. 54, SEQ ID NO. 56, SEQ ID NO. 58, and SEQ ID NO. 60.

11. The binding protein according to claim 8, wherein said cytokines are TNF-α and IL-13.

12. The binding protein according to claim 8, wherein said cytokines are IL-12 and IL-18.

13. The binding protein according to claim 12, wherein the binding protein comprises a DVD heavy chain amino acid sequence selected from the group consisting of SEQ ID NO. 83, SEQ ID NO. 90, SEQ ID NO. 93, SEQ ID NO. 95, and SEQ ID NO. 114; and a DVD light chain amino acid sequence selected from the group consisting of SEQ ID NO. 86, SEQ ID NO. 91, SEQ ID NO. 94, SEQ ID NO. 46, SEQ ID NO. 96, and SEQ ID NO. 116.

14. The binding protein according to claim 7 wherein the chemokine is selected from the group consisting of CCR2, CCR5 and CXCL-13.

15. The binding protein according to claim 7 wherein the cell surface protein is an integrin.

16. The binding protein according to claim 7 wherein the cell surface proteins are CD-20 and CD3.

17. The binding protein according to claim 16, wherein the binding protein comprises a DVD heavy chain amino acid sequence is SEQ ID NO. 97, and a DVD light chain SEQ ID NO. 101.

18. The binding protein according to claim 7 wherein the enzyme is selected from the group consisting of kinases and proteases.

19. The binding protein according to claim 7 wherein the receptor is selected from the group consisting of lymphokine receptor, monokine receptor, and polypeptide hormone receptor.

20. The binding protein according to claim 7, wherein said binding protein has an on rate constant(Kon) to said one or more targets selected from the group consisting of: at least about $10^2 M^{-1} s^{-1}$; at least about $10^3 M^{-1} s^{-1}$, at least about $10^4 M^{-1} s^{-1}$; at least about $10^5 M^{-1} s^{-1}$; and at least about $10^6 M^{-1} s^{-1}$, as measured by surface plasmon resonance.

21. The binding protein according to claim 7, wherein said binding protein has an off rate constant(Koff) to said one or more targets selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance.

22. The binding protein according to claim 7, wherein said binding protein has a dissociation constant ($K_D$) to said one or more targets selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

23. A binding protein conjugate comprising a binding protein described in any one of claims 1-8, 12, and 13, said binding protein conjugate further comprising an agent selected from the group consisting of; an immunoadhension molecule, an imaging agent, a therapeutic agent, and a cytotoxic agent.

24. The binding protein conjugate according to claim 23, wherein said agent is an imaging agent selected from the group consisting of a radiolabel, an enzyme, a fluorescent label, a luminescent label, a bioluminescent label, a magnetic label, and biotin.

25. The binding protein conjugate according to claim 24, wherein said imaging agent is a radiolabel selected from the group consisting of: $^3H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$.

26. The binding protein conjugate according to claim 23, wherein said agent is a therapeutic or cytotoxic agent selected from the group consisting of; an anti-metabolite, an alkylating agent, an antibiotic, a growth factor, a cytokine, an anti-angiogenic agent, an anti-mitotic agent, an anthracycline, toxin, and an apoptotic agent.

27. The binding protein according to claim 1, wherein said binding protein is a crystallized binding protein.

28. The crystallized binding protein according to claim 27, wherein said crystal is a carrier-free pharmaceutical controlled release crystal.

29. The crystallized binding protein according to claim 27, wherein said binding protein has a greater half life in vivo than the soluble counterpart of said binding protein.

30. The crystallized binding protein according to claim 27, wherein said binding protein retains biological activity.

31. A binding protein described in claim 1 produced according to a method comprising culturing a host cell in culture medium under conditions sufficient to produce said binding protein, wherein said host cell comprises a vector, said vector comprising a nucleic acid encoding said binding protein.

32. A pharmaceutical composition comprising a binding protein of any one of claims 1-8, 12, 13, 27-30, and 31, and a pharmaceutically acceptable carrier.

33. The pharmaceutical composition of claim 32 further comprising at least one additional therapeutic agent.

34. The binding protein according to any one of claims 1-6, wherein the linker XI is selected from the group consisting of AKTTPKLEEGEFSEAR (SEQ ID NO:118); AKTTPKLEE-GEFSEARV (SEQ ID NO:119); AKTTPKLGG (SEQ ID NO: 120); SAKTTPKLGG (SEQ ID NO:121); SAKTTP (SEQ ID NO:122); RADAAP (SEQ ID NO:123); RADAAPTVS (SEQ ID NO:124); RADAAAAGGPGS (SEQ ID NO:125); RADAAAA(G4S)4 (SEQ ID NO:126); SAKTTPKLEEGEFSEARV (SEQ ID NO: 127); ADAAP (SEQ ID NO:40); ADAAPTVSIFPP (SEQ ID NO:103); TVAAP (SEQ ID NO:44); TVAAPSVFIFPP (SEQ ID NO:50); QPKAAP (SEQ ID NO:88); QPKAAPSVTLFPP (SEQ ID NO:92); AKTTPP (SEQ ID NO:38); AKTTPPSVT-PLAP (SEQ ID NO:128); AKTTAP (SEQ ID NO:129); AKT-TAPSVYPLAP (SEQ ID NO:99); ASTKGP (SEQ ID NO:42); ASTKGPSVFPLAP (SEQ ID NO:48); GGGGSGGGGSGGGGS (SEQ ID NO:130); GENKVEYA-PALMALS (SEQ ID NO:131); GPAKELTPLKEAKVS (SEQ ID NO:132); and GHEAAAVMQVQYPAS (SEQ ID NO:133).

35. The pharmaceutical composition according to claim 33, wherein said additional agent is a therapeutic or imaging agent.

36. The pharmaceutical composition of claim 35, wherein said additional agent is selected from the group consisting of: Therapeutic agent, imaging agent, cytotoxic agent, angiogenesis inhibitors; kinase inhibitors; co-stimulation molecule blockers; adhesion molecule blockers; anti-cytokine antibody or functional fragment thereof; methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

37. A pharmaceutical composition comprising a binding protein conjugate according to claim 23 and a pharmaceutically acceptable carrier.

38. The pharmaceutical composition according to claim 37, wherein said binding protein congjugate comprises an imaging agent selected from the group consisting of a radiolabel, an enxyme, a fluorescent labe, a luminescent label, a bioluminescent label, a magnetic label, and biotin.

39. The pharmaceutical composition according to claim 38, wherein said imaging agent is a radiolabel selected from the group consisting of: $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm.

40. The pharamaceutical composition according to claim 37, wherein said binding protein conjugate comprises a therapeutic or cytotoxic agent selected from the group consisting of an anti-metabolite, an alkylating agent, an antibiotic, a growth factor, a cytokine, an anti-angiogenic agent, an anti-mitotic agent, an anthracycline, a toxin, and an apoptotic agent.

41. The pharmaceutical composition of claim 37 further comprising a second agent.

42. The pharmaceutical composition of claim 41, wherein said second agent is a therapeutic or imaging agent.

43. The pharmaceutical composition of claim 42, wherein said therapeutic or imaging agent is selected from the group: cytotoxic agent, angiogenesis inhibitors, kinase inhibitors; co-stimulation molecule blockers; adhesion molecule blockers; anti-cytokine antibody or functional fragment thereof; methotrexate; cyclosporin; rapamycin; FK506; detectable label or reportor; a TNF antagonist; an antiheumatic; a muscle relaxant, a narcotic, anon-steroid anti-inflammatory dug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppresive, a growth hormone, a hormone replacement drug, a radiopharmaceutical, $^{3}$H, $^{14}$C, $^{35}$S, $^{90}$Y, $^{99}$Tc, $^{111}$In, $^{125}$I, $^{131}$I, $^{177}$Lu, $^{166}$Ho, $^{153}$Sm, a fluorescent label, a luminescent label, a bioluminescent label, a magnetic label, biotin, an antidepressant, an antipsychotic, a stimulant, an asthma medication, a beta agonist, an inhaled steroid, an epinephrine or analog, a cytokine, and a cytokine antagonist.

* * * * *

SEQUENCE LISTING

<160> NUMBER OF SEQ ID NOS: 117

<210> SEQ ID NO 1
<211> LENGTH: 122
<212> TYPE: PRT
<213> ORGANISM: Mouse
<220> FEATURE:
<221> NAME/KEY: PEPTIDE
<222> LOCATION: (1)..(122)
<223> OTHER INFORMATION: Murine monoclonal antibody 3D12 binding human
      Il-1a (VH)

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg Asn Tyr
            20                  25                  30

Gly Met Asn Trp Val Lys Gln Ala Pro Gly Lys Asp Leu Lys Arg Met
        35                  40                  45

Ala Trp Ile Asn Thr Tyr Thr Gly Glu Ser Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Ile Tyr Tyr Tyr Gly Ser Ser Tyr Ala Met Asp Tyr Trp
            100                 105                 110

Gly Gln Gly Thr Ser Val Thr Val Ser Ser
        115                 120

<210> SEQ ID NO 2
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Murine monoclonal antibody 3D12 capable of
      binding human IL-1a (VL)

<400> SEQUENCE: 2

Asn Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Cys
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Pro Tyr
                85                  90                  95

Ala Phe Gly Gly Gly Thr Lys Leu Glu Ile Asn Arg
            100                 105

<210> SEQ ID NO 3
<211> LENGTH: 118
<212> TYPE: PRT

```
<213> ORGANISM: Mouse
<220> FEATURE:
<221> NAME/KEY: PEPTIDE
<222> LOCATION: (1)..(118)
<223> OTHER INFORMATION: Murine monoclonal antibody 18F4 capable of
      binding human IL-1a (VH)

<400> SEQUENCE: 3

Glu Val Gln Leu Gln Gln Ser Gly Ala Glu Leu Val Lys Pro Gly Ala
1               5                   10                  15

Ser Val Lys Leu Ser Cys Thr Ala Ser Gly Leu Asn Ile Lys Asp Thr
            20                  25                  30

Tyr Met His Trp Leu Lys Gln Arg Pro Glu Gln Gly Leu Glu Trp Ile
        35                  40                  45

Gly Arg Ile Asp Pro Ala Asn Gly Asn Ala Lys Tyr Asp Pro Arg Phe
    50                  55                  60

Leu Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Asp Gly Asn Phe His Phe Asp Tyr Trp Gly Gln Gly Thr
            100                 105                 110

Thr Leu Thr Val Ser Ser
        115

<210> SEQ ID NO 4
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Murine monoclonal antibody 18F4 capable of
      binding human IL-1a (VL)

<400> SEQUENCE: 4

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Arg Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Val Asp Leu Ala Glu Tyr Phe Cys Gln Gln Tyr Thr Arg Tyr Pro Leu
                85                  90                  95

Thr Phe Gly Gly Gly Thr Lys Leu Glu Ile Lys Arg
            100                 105

<210> SEQ ID NO 5
<211> LENGTH: 114
<212> TYPE: PRT
<213> ORGANISM: Mouse
<220> FEATURE:
<221> NAME/KEY: PEPTIDE
<222> LOCATION: (1)..(114)
<223> OTHER INFORMATION: Murine monoclonal antibody 6H3 capable of
      binding human IL-1a (VH)

<400> SEQUENCE: 5
```

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr Leu Tyr Ser Gln Lys Phe
    50                  55                  60

Lys Asp Thr Ala Ile Leu Thr Val Asp Lys Ser Ser Thr Ala Tyr
65              70                  75                  80

Met Gln Leu Ser Ser Leu Thr Ser Glu Asp Ser Ala Val Tyr Tyr Cys
                85                  90                  95

Ala Arg Tyr Gly Phe Asp Tyr Trp Gly Gln Gly Thr Thr Leu Thr Val
            100                 105                 110

Ser Ser

<210> SEQ ID NO 6
<211> LENGTH: 107
<212> TYPE: PRT
<213> ORGANISM: Mouse
<220> FEATURE:
<221> NAME/KEY: PEPTIDE
<222> LOCATION: (1)..(107)
<223> OTHER INFORMATION: Murine monoclonal antibody 6H3 capable of
      binding human IL-1a (VL)

<400> SEQUENCE: 6

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65              70                  75                  80

Asp Ala Ala Thr Tyr Tyr Cys Gln Gln Trp Asn Ser Asn Pro Tyr Thr
                85                  90                  95

Phe Gly Gly Gly Thr Lys Leu Glu Met Lys Arg
            100                 105

<210> SEQ ID NO 7
<211> LENGTH: 121
<212> TYPE: PRT
<213> ORGANISM: Mouse
<220> FEATURE:
<221> NAME/KEY: PEPTIDE
<222> LOCATION: (1)..(121)
<223> OTHER INFORMATION: Murine monoclonal antibody 13F5 capable of
      binding human IL-1b (VH)

<400> SEQUENCE: 7

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45
```

```
Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Thr Ser Tyr
 65                  70                  75                  80

Met Gln Leu Ser Gly Leu Thr Ser Glu Asp Ser Ala Met Tyr Phe Cys
                 85                  90                  95

Val Arg Phe Pro Thr Gly Asn Asp Tyr Tyr Ala Met Asp Tyr Trp Gly
                100                 105                 110

Gln Gly Thr Ser Val Thr Val Ser Ser
        115                 120

<210> SEQ ID NO 8
<211> LENGTH: 112
<212> TYPE: PRT
<213> ORGANISM: Mouse
<220> FEATURE:
<221> NAME/KEY: PEPTIDE
<222> LOCATION: (1)..(112)
<223> OTHER INFORMATION: Murine monoclonal antibody 13F5 capable of
      binding human IL-1b (VL)

<400> SEQUENCE: 8

Asn Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
                 20                  25                  30

Gly Asn Ser Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
         50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Phe Thr Phe Gly Ser Gly Thr Lys Leu Glu Ile Lys Arg
                100                 105                 110

<210> SEQ ID NO 9
<211> LENGTH: 122
<212> TYPE: PRT
<213> ORGANISM: Mouse
<220> FEATURE:
<221> NAME/KEY: PEPTIDE
<222> LOCATION: (1)..(122)
<223> OTHER INFORMATION: Murine monoclonal antibody 1B12 capable of
      binding human IL-1b (VH)

<400> SEQUENCE: 9

Gln Val His Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Asp Tyr
                 20                  25                  30

Gly Val Ser Trp Ile Arg Gln Pro Pro Gly Lys Gly Leu Glu Trp Leu
             35                  40                  45

Gly Leu Ile Trp Gly Gly Gly Asp Thr Tyr Tyr Asn Ser Pro Leu Lys
         50                  55                  60

Ser Arg Leu Ser Ile Arg Lys Asp Asn Ser Lys Ser Gln Val Phe Leu
 65                  70                  75                  80

Lys Met Asn Ser Leu Gln Thr Asp Asp Thr Ala Val Tyr Tyr Cys Ala
```

```
                      85                  90                  95

Lys Gln Arg Thr Leu Trp Gly Tyr Asp Leu Tyr Gly Met Asp Tyr Trp
            100                 105                 110

Gly Gln Gly Thr Ser Val Thr Val Ser Ser
            115                 120

<210> SEQ ID NO 10
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Murine monoclonal antibody 1B12 capable of
      binding human IL-1b (VL)

<400> SEQUENCE: 10

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Val Asp
            20                  25                  30

Met Asn Trp Tyr Gln Gln Lys Pro Gly Glu Pro Pro Lys Leu Leu Ile
        35                  40                  45

Ser Gln Gly Asn Thr Leu Arg Pro Gly Val Pro Ser Arg Phe Ser Ser
    50                  55                  60

Ser Gly Ser Gly Thr Asp Phe Val Phe Ile Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg
            100                 105

<210> SEQ ID NO 11
<211> LENGTH: 118
<212> TYPE: PRT
<213> ORGANISM: Mouse
<220> FEATURE:
<221> NAME/KEY: PEPTIDE
<222> LOCATION: (1)..(118)
<223> OTHER INFORMATION: Murine monoclonal antibody 6B12 capable of
      binding human IL-1b (VH)

<400> SEQUENCE: 11

Glu Val Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
            20                  25                  30

Tyr Met His Trp Val Arg Gln Ser His Gly Lys Ser Leu Glu Trp Ile
        35                  40                  45

Gly Tyr Ile Ser Cys Tyr Asn Gly Phe Thr Ser Tyr Asn Pro Lys Phe
    50                  55                  60

Lys Gly Lys Ala Thr Phe Thr Val Asp Thr Ser Ser Ser Thr Ala Tyr
65                  70                  75                  80

Ile Gln Phe Ser Arg Leu Thr Ser Glu Asp Ser Ala Val Tyr Tyr Cys
                85                  90                  95

Ala Arg Ser Asp Tyr Tyr Gly Asn Asp Tyr Trp Gly Gln Gly Thr
            100                 105                 110

Thr Leu Thr Val Ser Ser
            115
```

```
<210> SEQ ID NO 12
<211> LENGTH: 107
<212> TYPE: PRT
<213> ORGANISM: Mouse
<220> FEATURE:
<221> NAME/KEY: PEPTIDE
<222> LOCATION: (1)..(107)
<223> OTHER INFORMATION: Murine monoclonal antibody 6B12 capable of
      binding human IL-1b (VL)

<400> SEQUENCE: 12

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Ala Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Arg Ser Thr Tyr Pro Tyr Thr
                85                  90                  95

Phe Gly Gly Gly Thr Lys Leu Glu Ile Lys Arg
            100                 105

<210> SEQ ID NO 13
<211> LENGTH: 22
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(22)

<400> SEQUENCE: 13
atggtgtcca cagctcagtt cc                                          22

<210> SEQ ID NO 14
<211> LENGTH: 29
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(29)

<400> SEQUENCE: 14
gcagccaccg tacgccggtt tatttccag                                   29

<210> SEQ ID NO 15
<211> LENGTH: 24
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(24)

<400> SEQUENCE: 15
cgtacggtgg ctgcaccatc tgtc                                        24
```

```
<210> SEQ ID NO 16
<211> LENGTH: 23
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(23)

<400> SEQUENCE: 16
tcaacactct cccctgttga agc                                              23

<210> SEQ ID NO 17
<211> LENGTH: 22
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(22)

<400> SEQUENCE: 17
atggcttggg tgtggacctt gc                                               22

<210> SEQ ID NO 18
<211> LENGTH: 37
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(37)

<400> SEQUENCE: 18
gggcccttgg tcgacgctga ggagacggtg actgagg                               37

<210> SEQ ID NO 19
<211> LENGTH: 28
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(28)

<400> SEQUENCE: 19
gcgtcgacca agggcccatc ggtcttcc                                         28

<210> SEQ ID NO 20
<211> LENGTH: 26
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(26)

<400> SEQUENCE: 20
tcatttaccc ggagacaggg agaggc                                           26

<210> SEQ ID NO 21
<211> LENGTH: 24
<212> TYPE: DNA
<213> ORGANISM: Artificial
```

```
<220> FEATURE:
<223> OTHER INFORMATION: PCR Primer
<220> FEATURE:
<221> NAME/KEY: primer
<222> LOCATION: (1)..(24)

<400> SEQUENCE: 21
atagaatgga gctgggtttt cctc                                            24

<210> SEQ ID NO 22
<211> LENGTH: 35
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(35)

<400> SEQUENCE: 22
gggcccttgg tcgacgctga ggagacggtg actga                                35

<210> SEQ ID NO 23
<211> LENGTH: 24
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(24)

<400> SEQUENCE: 23
atggtcctca tgtccttgct gttc                                            24

<210> SEQ ID NO 24
<211> LENGTH: 34
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(34)

<400> SEQUENCE: 24
gcagccaccg tacgccgttt tatttccagc tttg                                 34

<210> SEQ ID NO 25
<211> LENGTH: 23
<212> TYPE: DNA
<213> ORGANISM: Artificial
<220> FEATURE:
<223> OTHER INFORMATION: PCR Primer
<220> FEATURE:
<221> NAME/KEY: primer1
<222> LOCATION: (1)..(23)

<400> SEQUENCE: 25
cagatccagt tggtgcagtc tgg                                             23

<210> SEQ ID NO 26
<211> LENGTH: 35
<212> TYPE: DNA
<213> ORGANISM: Artificial
<220> FEATURE:
<223> OTHER INFORMATION: PCR Primer
<220> FEATURE:
<221> NAME/KEY: primer
```

```
<222> LOCATION: (1)..(35)

<400> SEQUENCE: 26
caccaactgg atctgtgagg agacggtgac tgagg                               35

<210> SEQ ID NO 27
<211> LENGTH: 27
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(27)

<400> SEQUENCE: 27
aatatccaga tgacacagac tacatcc                                        27

<210> SEQ ID NO 28
<211> LENGTH: 36
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(36)

<400> SEQUENCE: 28
gtgtcatctg gatattccgt tttatttcca gctttg                              36

<210> SEQ ID NO 29
<211> LENGTH: 23
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(23)

<400> SEQUENCE: 29
tgggggtgtc gttttggctg agg                                            23

<210> SEQ ID NO 30
<211> LENGTH: 36
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(36)

<400> SEQUENCE: 30
gccaaaacga cccccaca gatccagttg gtgcag                                36

<210> SEQ ID NO 31
<211> LENGTH: 27
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(27)

<400> SEQUENCE: 31
```

-continued tggtgcagca tcagcccgtt ttatttc                                        27

<210> SEQ ID NO 32
<211> LENGTH: 33
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(33)

<400> SEQUENCE: 32
gctgatgctg caccaaatat ccagatgaca cag                                 33

<210> SEQ ID NO 33
<211> LENGTH: 243
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(243)
<223> OTHER INFORMATION: DVD heavy variable hIL-1a/bDVD1-Ig region

<400> SEQUENCE: 33

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Ser Thr Ser Tyr
65                  70                  75                  80

Met Gln Leu Ser Gly Leu Thr Ser Glu Asp Ser Ala Met Tyr Phe Cys
                85                  90                  95

Val Arg Phe Pro Thr Gly Asn Asp Tyr Tyr Ala Met Asp Tyr Trp Gly
                100                 105                 110

Gln Gly Thr Ser Val Thr Val Ser Ser Gln Ile Gln Leu Val Gln Ser
            115                 120                 125

Gly Pro Glu Leu Lys Lys Pro Gly Glu Thr Val Lys Ile Ser Cys Lys
        130                 135                 140

Ala Ser Gly Tyr Thr Phe Arg Asn Tyr Gly Met Asn Trp Val Lys Gln
145                 150                 155                 160

Ala Pro Gly Lys Asp Leu Lys Arg Met Ala Trp Ile Asn Thr Tyr Thr
                165                 170                 175

Gly Glu Ser Thr Tyr Ala Asp Asp Phe Lys Gly Arg Phe Ala Phe Ser
            180                 185                 190

Leu Glu Thr Ser Ala Ser Thr Ala Tyr Leu Gln Ile Asn Asn Leu Lys
        195                 200                 205

Asn Glu Asp Thr Ala Thr Tyr Phe Cys Ala Arg Gly Ile Tyr Tyr Tyr
210                 215                 220

Gly Ser Ser Tyr Ala Met Asp Tyr Trp Gly Gln Gly Thr Ser Val Thr
225                 230                 235                 240

Val Ser Ser

```
<210> SEQ ID NO 34
<211> LENGTH: 330
<212> TYPE: PRT
<213> ORGANISM: Homo sapiens
<220> FEATURE:
<221> NAME/KEY: PEPTIDE
<222> LOCATION: (1)..(330)
<223> OTHER INFORMATION: Sequence of CH region

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 221
<212> TYPE: PRT
<213> ORGANISM: Artificial
```

```
<220> FEATURE:
<223> OTHER INFORMATION: Chimeric mouse/human VL region
<220> FEATURE:
<221> NAME/KEY: PEPTIDE
<222> LOCATION: (1)..(221)
<223> OTHER INFORMATION: DVD light variable hIL-1a/bDVD1-Ig region

<400> SEQUENCE: 35

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Phe Thr Phe Gly Ser Gly Thr Lys Leu Glu Ile Lys Arg
            100                 105                 110

Asn Ile Gln Met Thr Gln Thr Thr Ser Ser Leu Ser Ala Ser Leu Gly
        115                 120                 125

Asp Arg Val Thr Ile Ser Cys Arg Ala Ser Gln Asp Ile Ser Asn Cys
    130                 135                 140

Leu Asn Trp Tyr Gln Gln Lys Pro Asp Gly Thr Val Lys Leu Leu Ile
145                 150                 155                 160

Tyr Tyr Thr Ser Arg Leu His Ser Gly Val Pro Ser Arg Phe Ser Gly
                165                 170                 175

Ser Gly Ser Gly Thr Asp Tyr Ser Leu Thr Ile Ser Asn Leu Glu Gln
            180                 185                 190

Glu Asp Ile Ala Thr Tyr Phe Cys Gln Gln Gly Lys Thr Leu Pro Tyr
        195                 200                 205

Ala Phe Gly Gly Gly Thr Lys Leu Glu Ile Asn Arg Arg
    210                 215                 220

<210> SEQ ID NO 36
<211> LENGTH: 106
<212> TYPE: PRT
<213> ORGANISM: Homo sapiens
<220> FEATURE:
<221> NAME/KEY: PEPTIDE
<222> LOCATION: (1)..(106)
<223> OTHER INFORMATION: Sequence of CL region

<400> SEQUENCE: 36

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
```

```
                    85                  90                  95
Val Thr Lys Ser Phe Asn Arg Gly Glu Cys
            100                 105

<210> SEQ ID NO 37
<211> LENGTH: 249
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(249)
<223> OTHER INFORMATION: DVD heavy variable hIL-1a/bDVD2-Ig region

<400> SEQUENCE: 37

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ser Thr Tyr
65                  70                  75                  80

Met Gln Leu Ser Gly Leu Thr Ser Glu Asp Ser Ala Met Tyr Phe Cys
                85                  90                  95

Val Arg Phe Pro Thr Gly Asn Asp Tyr Tyr Ala Met Asp Tyr Trp Gly
            100                 105                 110

Gln Gly Thr Ser Val Thr Val Ser Ser Ala Lys Thr Thr Pro Pro Gln
        115                 120                 125

Ile Gln Leu Val Gln Ser Gly Pro Glu Leu Lys Lys Pro Gly Glu Thr
    130                 135                 140

Val Lys Ile Ser Cys Lys Ala Ser Gly Tyr Thr Phe Arg Asn Tyr Gly
145                 150                 155                 160

Met Asn Trp Val Lys Gln Ala Pro Gly Lys Asp Leu Lys Arg Met Ala
                165                 170                 175

Trp Ile Asn Thr Tyr Thr Gly Glu Ser Thr Tyr Ala Asp Asp Phe Lys
            180                 185                 190

Gly Arg Phe Ala Phe Ser Leu Glu Thr Ser Ala Ser Thr Ala Tyr Leu
        195                 200                 205

Gln Ile Asn Asn Leu Lys Asn Glu Asp Thr Ala Thr Tyr Phe Cys Ala
    210                 215                 220

Arg Gly Ile Tyr Tyr Tyr Gly Ser Ser Tyr Ala Met Asp Tyr Trp Gly
225                 230                 235                 240

Gln Gly Thr Ser Val Thr Val Ser Ser
                245

<210> SEQ ID NO 38
<211> LENGTH: 6
<212> TYPE: PRT
<213> ORGANISM: Artificial
<220> FEATURE:
<223> OTHER INFORMATION: Linker peptide
<220> FEATURE:
<221> NAME/KEY: PEPTIDE
<222> LOCATION: (1)..(6)
<223> OTHER INFORMATION: LInker peptide
```

```
<400> SEQUENCE: 38

Ala Lys Thr Thr Pro Pro
1               5

<210> SEQ ID NO 39
<211> LENGTH: 225
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(225)
<223> OTHER INFORMATION: DVD light variable hIL-1a/bDVD2-Ig region

<400> SEQUENCE: 39

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Phe Thr Phe Gly Ser Gly Thr Lys Leu Glu Ile Lys Arg
            100                 105                 110

Ala Asp Ala Ala Pro Asn Ile Gln Met Thr Gln Thr Thr Ser Ser Leu
        115                 120                 125

Ser Ala Ser Leu Gly Asp Arg Val Thr Ile Ser Cys Arg Ala Ser Gln
    130                 135                 140

Asp Ile Ser Asn Cys Leu Asn Trp Tyr Gln Gln Lys Pro Asp Gly Thr
145                 150                 155                 160

Val Lys Leu Leu Ile Tyr Tyr Thr Ser Arg Leu His Ser Gly Val Pro
                165                 170                 175

Ser Arg Phe Ser Gly Ser Gly Ser Gly Thr Asp Tyr Ser Leu Thr Ile
            180                 185                 190

Ser Asn Leu Glu Gln Glu Asp Ile Ala Thr Tyr Phe Cys Gln Gln Gly
        195                 200                 205

Lys Thr Leu Pro Tyr Ala Phe Gly Gly Gly Thr Lys Leu Glu Ile Asn
    210                 215                 220

Arg
225

<210> SEQ ID NO 40
<211> LENGTH: 5
<212> TYPE: PRT
<213> ORGANISM: Artificial
<220> FEATURE:
<223> OTHER INFORMATION: Linker peptide
<220> FEATURE:
<221> NAME/KEY: PEPTIDE
<222> LOCATION: (1)..(5)
<223> OTHER INFORMATION: Linker peptide

<400> SEQUENCE: 40

Ala Asp Ala Ala Pro
```

-continued

<210> SEQ ID NO 41
<211> LENGTH: 246
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(246)
<223> OTHER INFORMATION: DVD heavy variable hIL-1a/b DVD3a-Ig region

<400> SEQUENCE: 41

Glu Val Gln Leu Gln Gln Ser Gly Ala Glu Leu Val Lys Pro Gly Ala
1               5                   10                  15

Ser Val Lys Leu Ser Cys Thr Ala Ser Gly Leu Asn Ile Lys Asp Thr
            20                  25                  30

Tyr Met His Trp Leu Lys Gln Arg Pro Glu Gln Gly Leu Glu Trp Ile
        35                  40                  45

Gly Arg Ile Asp Pro Ala Asn Gly Asn Ala Lys Tyr Asp Pro Arg Phe
    50                  55                  60

Leu Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Asp Gly Asn Phe His Phe Asp Tyr Trp Gly Gln Gly Thr
            100                 105                 110

Thr Leu Thr Val Ser Ser Ala Ser Thr Lys Gly Pro Gln Val His Leu
        115                 120                 125

Lys Glu Ser Gly Pro Gly Leu Val Ala Pro Ser Gln Ser Leu Ser Ile
    130                 135                 140

Thr Cys Thr Val Ser Gly Phe Ser Leu Thr Asp Tyr Gly Val Ser Trp
145                 150                 155                 160

Ile Arg Gln Pro Pro Gly Lys Gly Leu Glu Trp Leu Gly Leu Ile Trp
                165                 170                 175

Gly Gly Gly Asp Thr Tyr Tyr Asn Ser Pro Leu Lys Ser Arg Leu Ser
            180                 185                 190

Ile Arg Lys Asp Asn Ser Lys Ser Gln Val Phe Leu Lys Met Asn Ser
        195                 200                 205

Leu Gln Thr Asp Asp Thr Ala Val Tyr Tyr Cys Ala Lys Gln Arg Thr
    210                 215                 220

Leu Trp Gly Tyr Asp Leu Tyr Gly Met Asp Tyr Trp Gly Gln Gly Thr
225                 230                 235                 240

Ser Val Thr Val Ser Ser
                245

<210> SEQ ID NO 42
<211> LENGTH: 6
<212> TYPE: PRT
<213> ORGANISM: Artificial
<220> FEATURE:
<223> OTHER INFORMATION: Linker peptide
<220> FEATURE:
<221> NAME/KEY: PEPTIDE
<222> LOCATION: (1)..(6)
<223> OTHER INFORMATION: Linker peptide

<400> SEQUENCE: 42

Ala Ser Thr Lys Gly Pro

```
<210> SEQ ID NO 43
<211> LENGTH: 222
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(222)
<223> OTHER INFORMATION: DVD light variable hIL-1a/b DVD3a-Ig region

<400> SEQUENCE: 43

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Arg Ala Leu Ile
        35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Val Asp Leu Ala Glu Tyr Phe Cys Gln Gln Tyr Thr Arg Tyr Pro Leu
                85                  90                  95

Thr Phe Gly Gly Gly Thr Lys Leu Glu Ile Lys Arg Thr Val Ala Ala
            100                 105                 110

Pro Glu Thr Thr Val Thr Gln Ser Pro Ala Ser Leu Ser Met Ala Ile
        115                 120                 125

Gly Glu Lys Val Thr Ile Arg Cys Ile Thr Ser Thr Asp Ile Asp Val
    130                 135                 140

Asp Met Asn Trp Tyr Gln Gln Lys Pro Gly Glu Pro Pro Lys Leu Leu
145                 150                 155                 160

Ile Ser Gln Gly Asn Thr Leu Arg Pro Gly Val Pro Ser Arg Phe Ser
                165                 170                 175

Ser Ser Gly Ser Gly Thr Asp Phe Val Phe Ile Ile Glu Asn Met Leu
            180                 185                 190

Ser Glu Asp Val Ala Asp Tyr Tyr Cys Leu Gln Ser Asp Asn Leu Pro
        195                 200                 205

Leu Thr Phe Gly Ala Gly Thr Lys Leu Glu Leu Lys Arg Arg
    210                 215                 220

<210> SEQ ID NO 44
<211> LENGTH: 5
<212> TYPE: PRT
<213> ORGANISM: Artificial
<220> FEATURE:
<223> OTHER INFORMATION: Linker peptide
<220> FEATURE:
<221> NAME/KEY: PEPTIDE
<222> LOCATION: (1)..(5)
<223> OTHER INFORMATION: Linker peptide

<400> SEQUENCE: 44

Thr Val Ala Ala Pro
1               5

<210> SEQ ID NO 45
<211> LENGTH: 246
<212> TYPE: PRT
```

<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(246)
<223> OTHER INFORMATION: DVD heavy variable hIL-1a/b DVD3b-Ig region

<400> SEQUENCE: 45

```
Gln Val His Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Ser Trp Ile Arg Gln Pro Pro Gly Lys Gly Leu Glu Trp Leu
        35                  40                  45

Gly Leu Ile Trp Gly Gly Asp Thr Tyr Tyr Asn Ser Pro Leu Lys
    50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Ser Val Thr Val Ser Ser Ala Ser Thr Lys Gly Pro
        115                 120                 125

Glu Val Gln Leu Gln Gln Ser Gly Ala Glu Leu Val Lys Pro Gly Ala
    130                 135                 140

Ser Val Lys Leu Ser Cys Thr Ala Ser Gly Leu Asn Ile Lys Asp Thr
145                 150                 155                 160

Tyr Met His Trp Leu Lys Gln Arg Pro Glu Gln Gly Leu Glu Trp Ile
                165                 170                 175

Gly Arg Ile Asp Pro Ala Asn Gly Asn Ala Lys Tyr Asp Pro Arg Phe
            180                 185                 190

Leu Gly Lys Ala Thr Ile Thr Ala Asp Thr Ser Ser Asn Thr Ala Tyr
        195                 200                 205

Leu Gln Leu Ser Ser Leu Thr Ser Glu Asp Thr Ala Val Tyr Tyr Cys
    210                 215                 220

Ala Arg Gly Asp Gly Asn Phe His Phe Asp Tyr Trp Gly Gln Gly Thr
225                 230                 235                 240

Thr Leu Thr Val Ser Ser
                245
```

<210> SEQ ID NO 46
<211> LENGTH: 221
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(221)
<223> OTHER INFORMATION: DVD light variable hIL-1a/b DVD3b-Ig region

<400> SEQUENCE: 46

```
Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Val Asp
            20                  25                  30

Met Asn Trp Tyr Gln Gln Lys Pro Gly Glu Pro Pro Lys Leu Leu Ile
```

-continued

```
                35                  40                  45
Ser Gln Gly Asn Thr Leu Arg Pro Gly Val Pro Ser Arg Phe Ser Ser
    50                  55                  60

Ser Gly Ser Gly Thr Asp Phe Val Phe Ile Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg Thr Val Ala Ala
            100                 105                 110

Pro Asp Ile Val Met Thr Gln Ser Gln Arg Phe Met Ser Thr Ser Val
        115                 120                 125

Gly Asp Arg Val Ser Val Thr Cys Lys Ala Ser Gln Asn Val Gly Thr
    130                 135                 140

Asn Ile Ala Trp Tyr Gln Gln Lys Pro Gly Gln Ser Pro Arg Ala Leu
145                 150                 155                 160

Ile Tyr Ser Ala Ser Tyr Arg Tyr Ser Gly Val Pro Asp Arg Phe Thr
                165                 170                 175

Gly Ser Gly Ser Gly Thr Asp Phe Thr Leu Thr Ile Ser Asn Val Gln
            180                 185                 190

Ser Val Asp Leu Ala Glu Tyr Phe Cys Gln Gln Tyr Thr Arg Tyr Pro
        195                 200                 205

Leu Thr Phe Gly Gly Gly Thr Lys Leu Glu Ile Lys Arg
    210                 215                 220

<210> SEQ ID NO 47
<211> LENGTH: 253
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(253)
<223> OTHER INFORMATION: DVD heavy variable hIL-1a/b DVD4a-Ig region

<400> SEQUENCE: 47

Glu Val Gln Leu Gln Gln Ser Gly Ala Glu Leu Val Lys Pro Gly Ala
1               5                   10                  15

Ser Val Lys Leu Ser Cys Thr Ala Ser Gly Leu Asn Ile Lys Asp Thr
            20                  25                  30

Tyr Met His Trp Leu Lys Gln Arg Pro Glu Gln Gly Leu Glu Trp Ile
        35                  40                  45

Gly Arg Ile Asp Pro Ala Asn Gly Asn Ala Lys Tyr Asp Pro Arg Phe
    50                  55                  60

Leu Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Asp Gly Asn Phe His Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Gln Val His Leu Lys Glu Ser Gly Pro Gly Leu Val Ala
    130                 135                 140

Pro Ser Gln Ser Leu Ser Ile Thr Cys Thr Val Ser Gly Phe Ser Leu
145                 150                 155                 160
```

```
Thr Asp Tyr Gly Val Ser Trp Ile Arg Gln Pro Gly Lys Gly Leu
                165                 170                 175

Glu Trp Leu Gly Leu Ile Trp Gly Gly Gly Asp Thr Tyr Tyr Asn Ser
            180                 185                 190

Pro Leu Lys Ser Arg Leu Ser Ile Arg Lys Asp Asn Ser Lys Ser Gln
                195                 200                 205

Val Phe Leu Lys Met Asn Ser Leu Gln Thr Asp Asp Thr Ala Val Tyr
            210                 215                 220

Tyr Cys Ala Lys Gln Arg Thr Leu Trp Gly Tyr Asp Leu Tyr Gly Met
225                 230                 235                 240

Asp Tyr Trp Gly Gln Gly Thr Ser Val Thr Val Ser Ser
                245                 250

<210> SEQ ID NO 48
<211> LENGTH: 13
<212> TYPE: PRT
<213> ORGANISM: Artificial
<220> FEATURE:
<223> OTHER INFORMATION: Linker peptide
<220> FEATURE:
<221> NAME/KEY: PEPTIDE
<222> LOCATION: (1)..(13)
<223> OTHER INFORMATION: Linker peptide

<400> SEQUENCE: 48

Ala Ser Thr Lys Gly Pro Ser Val Phe Pro Leu Ala Pro
1               5                   10

<210> SEQ ID NO 49
<211> LENGTH: 228
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(228)
<223> OTHER INFORMATION: DVD light variable hIL-1a/bDVD4a-Ig region

<400> SEQUENCE: 49

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Arg Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Val Asp Leu Ala Glu Tyr Phe Cys Gln Gln Tyr Thr Arg Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Glu Thr Thr Val Thr Gln Ser Pro
        115                 120                 125

Ala Ser Leu Ser Met Ala Ile Gly Glu Lys Val Thr Ile Arg Cys Ile
    130                 135                 140

Thr Ser Thr Asp Ile Asp Val Asp Met Asn Trp Tyr Gln Gln Lys Pro
145                 150                 155                 160
```

-continued

```
Gly Glu Pro Pro Lys Leu Leu Ile Ser Gln Gly Asn Thr Leu Arg Pro
                165                 170                 175

Gly Val Pro Ser Arg Phe Ser Ser Gly Ser Gly Thr Asp Phe Val
            180                 185                 190

Phe Ile Ile Glu Asn Met Leu Ser Glu Asp Val Ala Asp Tyr Tyr Cys
            195                 200                 205

Leu Gln Ser Asp Asn Leu Pro Leu Thr Phe Gly Ala Gly Thr Lys Leu
    210                 215                 220

Glu Leu Lys Arg
225

<210> SEQ ID NO 50
<211> LENGTH: 12
<212> TYPE: PRT
<213> ORGANISM: Artificial
<220> FEATURE:
<223> OTHER INFORMATION: Linker peptide
<220> FEATURE:
<221> NAME/KEY: PEPTIDE
<222> LOCATION: (1)..(12)
<223> OTHER INFORMATION: Linker peptide

<400> SEQUENCE: 50

Thr Val Ala Ala Pro Ser Val Phe Ile Phe Pro Pro
1               5                   10

<210> SEQ ID NO 51
<211> LENGTH: 253
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(253)
<223> OTHER INFORMATION: DVD heavy variable hIL-1a/b DVD4b-Ig region

<400> SEQUENCE: 51

Gln Val His Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
                20                  25                  30

Gly Val Ser Trp Ile Arg Gln Pro Pro Gly Lys Gly Leu Glu Trp Leu
            35                  40                  45

Gly Leu Ile Trp Gly Gly Gly Asp Thr Tyr Tyr Asn Ser Pro Leu Lys
        50                  55                  60

Ser Arg Leu Ser Ile Arg Lys Asp Asn Ser Lys Ser Gln Val Phe Leu
65                  70                  75                  80

Lys Met Asn Ser Leu Gln Thr Asp Asp Thr Ala Val Tyr Tyr Cys Ala
                85                  90                  95

Lys Gln Arg Thr Leu Trp Gly Tyr Asp Leu Tyr Gly Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Glu Val Gln Leu Gln Gln Ser Gly Ala
    130                 135                 140

Glu Leu Val Lys Pro Gly Ala Ser Val Lys Leu Ser Cys Thr Ala Ser
145                 150                 155                 160

Gly Leu Asn Ile Lys Asp Thr Tyr Met His Trp Leu Lys Gln Arg Pro
                165                 170                 175
```

```
Glu Gln Gly Leu Glu Trp Ile Gly Arg Ile Asp Pro Ala Asn Gly Asn
                180                 185                 190

Ala Lys Tyr Asp Pro Arg Phe Leu Gly Lys Ala Thr Ile Thr Ala Asp
                195                 200                 205

Thr Ser Ser Asn Thr Ala Tyr Leu Gln Leu Ser Ser Leu Thr Ser Glu
                210                 215                 220

Asp Thr Ala Val Tyr Tyr Cys Ala Arg Gly Asp Gly Asn Phe His Phe
225                 230                 235                 240

Asp Tyr Trp Gly Gln Gly Thr Thr Leu Thr Val Ser Ser
                245                 250
```

<210> SEQ ID NO 52
<211> LENGTH: 228
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(228)
<223> OTHER INFORMATION: DVD light variable hIL-1a/b DVD4b-Ig region

<400> SEQUENCE: 52

```
Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Val Asp
                20                  25                  30

Met Asn Trp Tyr Gln Gln Lys Pro Gly Glu Pro Pro Lys Leu Leu Ile
                35                  40                  45

Ser Gln Gly Asn Thr Leu Arg Pro Gly Val Pro Ser Arg Phe Ser Ser
        50                  55                  60

Ser Gly Ser Gly Thr Asp Phe Val Phe Ile Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Asp Ile Val Met Thr Gln Ser Gln
                115                 120                 125

Arg Phe Met Ser Thr Ser Val Gly Asp Arg Val Ser Val Thr Cys Lys
            130                 135                 140

Ala Ser Gln Asn Val Gly Thr Asn Ile Ala Trp Tyr Gln Gln Lys Pro
145                 150                 155                 160

Gly Gln Ser Pro Arg Ala Leu Ile Tyr Ser Ala Ser Tyr Arg Tyr Ser
                165                 170                 175

Gly Val Pro Asp Arg Phe Thr Gly Ser Gly Ser Gly Thr Asp Phe Thr
                180                 185                 190

Leu Thr Ile Ser Asn Val Gln Ser Val Asp Leu Ala Glu Tyr Phe Cys
                195                 200                 205

Gln Gln Tyr Thr Arg Tyr Pro Leu Thr Phe Gly Gly Gly Thr Lys Leu
            210                 215                 220

Glu Ile Lys Arg
225
```

<210> SEQ ID NO 53
<211> LENGTH: 238
<212> TYPE: PRT
<213> ORGANISM: Artificial

```
<220> FEATURE:
<223> OTHER INFORMATION: Chimeric mouse/human VH region
<220> FEATURE:
<221> NAME/KEY: PEPTIDE
<222> LOCATION: (1)..(238)
<223> OTHER INFORMATION: DVD heavy variable hIL-1a/b DVD5a-Ig region

<400> SEQUENCE: 53

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr Leu Tyr Ser Gln Lys Phe
    50                  55                  60

Lys Asp Thr Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Gly Phe Asp Tyr Trp Gly Gln Gly Thr Thr Leu Thr Val
            100                 105                 110

Ser Ser Ala Ser Thr Lys Gly Pro Glu Val Gln Leu Gln Gln Ser Gly
        115                 120                 125

Pro Glu Leu Val Lys Thr Gly Thr Ser Val Lys Ile Ser Cys Lys Ala
    130                 135                 140

Ser Gly Tyr Ser Phe Thr Gly Tyr Tyr Met His Trp Val Arg Gln Ser
145                 150                 155                 160

His Gly Lys Ser Leu Glu Trp Ile Gly Tyr Ile Ser Cys Tyr Asn Gly
                165                 170                 175

Phe Thr Ser Tyr Asn Pro Lys Phe Lys Gly Lys Ala Thr Phe Thr Val
            180                 185                 190

Asp Thr Ser Ser Ser Thr Ala Tyr Ile Gln Phe Ser Arg Leu Thr Ser
        195                 200                 205

Glu Asp Ser Ala Val Tyr Tyr Cys Ala Arg Ser Asp Tyr Tyr Gly Thr
    210                 215                 220

Asn Asp Tyr Trp Gly Gln Gly Thr Thr Leu Thr Val Ser Ser
225                 230                 235

<210> SEQ ID NO 54
<211> LENGTH: 219
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(219)
<223> OTHER INFORMATION: DVD light variable hIL-1a/b DVD5a-Ig region

<400> SEQUENCE: 54

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Asn Ser Asn Pro Tyr Thr
                 85                  90                  95

Phe Gly Gly Gly Thr Lys Leu Glu Met Lys Arg Thr Val Ala Ala Pro
            100                 105                 110

Gln Ile Val Leu Thr Gln Ser Pro Ala Ile Met Ser Ala Ser Pro Gly
            115                 120                 125

Glu Lys Val Thr Ile Thr Cys Ser Ala Ser Ser Ser Val Ser Tyr Met
130                 135                 140

His Trp Phe Gln Gln Lys Pro Gly Ala Ser Pro Lys Leu Trp Ile Tyr
145                 150                 155                 160

Ser Thr Ser Asn Leu Ala Ser Gly Val Pro Ala Arg Phe Ser Gly Ser
                165                 170                 175

Gly Ser Gly Thr Ser Tyr Ser Leu Thr Val Ser Arg Met Glu Ala Glu
                180                 185                 190

Asp Ala Ala Thr Tyr Tyr Cys Gln Gln Arg Ser Thr Tyr Pro Tyr Thr
                195                 200                 205

Phe Gly Gly Gly Thr Lys Leu Glu Ile Lys Arg
            210                 215

<210> SEQ ID NO 55
<211> LENGTH: 238
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(238)
<223> OTHER INFORMATION: DVD heavy variable  hIL-1a/b DVD5b-Ig region

<400> SEQUENCE: 55

Glu Val Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
                20                  25                  30

Tyr Met His Trp Val Arg Gln Ser His Gly Lys Ser Leu Glu Trp Ile
            35                  40                  45

Gly Tyr Ile Ser Cys Tyr Asn Gly Phe Thr Ser Tyr Asn Pro Lys Phe
        50                  55                  60

Lys Gly Lys Ala Thr Phe Thr Val Asp Thr Ser Ser Ser Thr Ala Tyr
 65                  70                  75                  80

Ile Gln Phe Ser Arg Leu Thr Ser Glu Asp Ser Ala Val Tyr Tyr Cys
                 85                  90                  95

Ala Arg Ser Asp Tyr Tyr Gly Thr Asn Asp Tyr Trp Gly Gln Gly Thr
            100                 105                 110

Thr Leu Thr Val Ser Ser Ala Ser Thr Lys Gly Pro Gln Val Gln Leu
        115                 120                 125

Gln Gln Pro Gly Ala Glu Leu Val Arg Pro Gly Ala Ser Val Lys Leu
130                 135                 140

Ser Cys Lys Ala Ser Gly Tyr Thr Phe Thr Thr Tyr Trp Met Asn Trp
145                 150                 155                 160

Val Lys Gln Arg Pro Glu Gln Gly Leu Glu Trp Ile Gly Arg Ile Asp
                165                 170                 175

Pro Tyr Asp Ser Glu Thr Leu Tyr Ser Gln Lys Phe Lys Asp Thr Ala
```

-continued

```
                180                 185                 190
Ile Leu Thr Val Asp Lys Ser Ser Thr Ala Tyr Met Gln Leu Ser
        195                 200                 205

Ser Leu Thr Ser Glu Asp Ser Ala Val Tyr Tyr Cys Ala Arg Tyr Gly
    210                 215                 220

Phe Asp Tyr Trp Gly Gln Gly Thr Thr Leu Thr Val Ser Ser
225                 230                 235
```

<210> SEQ ID NO 56
<211> LENGTH: 219
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(219)
<223> OTHER INFORMATION: DVD light variable hIL-1a/b DVD5b-Ig region

<400> SEQUENCE: 56

```
Gln Ile Val Leu Thr Gln Ser Pro Ala Ile Met Ser Ala Ser Pro Gly
1               5                  10                  15

Glu Lys Val Thr Ile Thr Cys Ser Ala Ser Ser Ser Val Ser Tyr Met
            20                  25                  30

His Trp Phe Gln Gln Lys Pro Gly Ala Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Arg Ser Thr Tyr Pro Tyr Thr
                85                  90                  95

Phe Gly Gly Gly Thr Lys Leu Glu Ile Lys Arg Thr Val Ala Ala Pro
            100                 105                 110

Gln Ile Val Leu Thr Gln Ser Pro Ala Leu Met Ser Ala Ser Pro Gly
        115                 120                 125

Glu Lys Val Thr Met Thr Cys Ser Ala Ser Ser Ser Val Asn Tyr Met
    130                 135                 140

Tyr Trp Tyr Gln Gln Lys Pro Arg Ser Ser Pro Lys Pro Trp Ile Tyr
145                 150                 155                 160

Leu Thr Ser Asn Leu Ala Ser Gly Val Pro Ala Arg Phe Ser Gly Ser
                165                 170                 175

Gly Ser Gly Thr Ser Tyr Ser Leu Thr Ile Ser Ser Met Glu Ala Glu
            180                 185                 190

Asp Ala Ala Thr Tyr Tyr Cys Gln Gln Trp Asn Ser Asn Pro Tyr Thr
        195                 200                 205

Phe Gly Gly Gly Thr Lys Leu Glu Met Lys Arg
    210                 215
```

<210> SEQ ID NO 57
<211> LENGTH: 245
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(245)
<223> OTHER INFORMATION: DVD heavy variable hIL-1a/b DVD6a-Ig region

```
<400> SEQUENCE: 57

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr Leu Tyr Ser Gln Lys Phe
    50                  55                  60

Lys Asp Thr Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Gly Phe Asp Tyr Trp Gly Gln Gly Thr Thr Leu Thr Val
            100                 105                 110

Ser Ser Ala Ser Thr Lys Gly Pro Ser Val Phe Pro Leu Ala Pro Glu
        115                 120                 125

Val Gln Leu Gln Gln Ser Gly Pro Glu Leu Val Lys Thr Gly Thr Ser
    130                 135                 140

Val Lys Ile Ser Cys Lys Ala Ser Gly Tyr Ser Phe Thr Gly Tyr Tyr
145                 150                 155                 160

Met His Trp Val Arg Gln Ser His Gly Lys Ser Leu Glu Trp Ile Gly
                165                 170                 175

Tyr Ile Ser Cys Tyr Asn Gly Phe Thr Ser Tyr Asn Pro Lys Phe Lys
            180                 185                 190

Gly Lys Ala Thr Phe Thr Val Asp Thr Ser Ser Ser Thr Ala Tyr Ile
        195                 200                 205

Gln Phe Ser Arg Leu Thr Ser Glu Asp Ser Ala Val Tyr Tyr Cys Ala
    210                 215                 220

Arg Ser Asp Tyr Tyr Gly Thr Asn Asp Tyr Trp Gly Gln Gly Thr Thr
225                 230                 235                 240

Leu Thr Val Ser Ser
                245

<210> SEQ ID NO 58
<211> LENGTH: 227
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(227)
<223> OTHER INFORMATION: DVD light variable hIL-1a/b DVD 6a-Ig region

<400> SEQUENCE: 58

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80
```

```
Asp Ala Ala Thr Tyr Tyr Cys Gln Gln Trp Asn Ser Asn Pro Tyr Thr
                85                  90                  95

Phe Gly Gly Gly Thr Lys Leu Glu Met Lys Arg Thr Val Ala Ala Pro
            100                 105                 110

Ser Val Phe Ile Phe Pro Pro Gln Ile Val Leu Thr Gln Ser Pro Ala
        115                 120                 125

Ile Met Ser Ala Ser Pro Gly Glu Lys Val Thr Ile Thr Cys Ser Ala
    130                 135                 140

Ser Ser Ser Val Ser Tyr Met His Trp Phe Gln Gln Lys Pro Gly Ala
145                 150                 155                 160

Ser Pro Lys Leu Trp Ile Tyr Ser Thr Ser Asn Leu Ala Ser Gly Val
                165                 170                 175

Pro Ala Arg Phe Ser Gly Ser Gly Ser Gly Thr Ser Tyr Ser Leu Thr
            180                 185                 190

Val Ser Arg Met Glu Ala Glu Asp Ala Ala Thr Tyr Tyr Cys Gln Gln
        195                 200                 205

Arg Ser Thr Tyr Pro Tyr Thr Phe Gly Gly Gly Thr Lys Leu Glu Ile
    210                 215                 220

Lys Arg Arg
225

<210> SEQ ID NO 59
<211> LENGTH: 245
<212> TYPE: PRT
<213> ORGANISM: Artificial
<220> FEATURE:
<223> OTHER INFORMATION: Chimeric mouse/human VH region
<220> FEATURE:
<221> NAME/KEY: PEPTIDE
<222> LOCATION: (1)..(245)
<223> OTHER INFORMATION: DVD heavy variable hIL-1a/b DVD6b-Ig region

<400> SEQUENCE: 59

Glu Val Gln Leu Gln Gln Ser Gly Pro Glu Leu Val Lys Thr Gly Thr
1               5                   10                  15

Ser Val Lys Ile Ser Cys Lys Ala Ser Gly Tyr Ser Phe Thr Gly Tyr
            20                  25                  30

Tyr Met His Trp Val Arg Gln Ser His Gly Lys Ser Leu Glu Trp Ile
        35                  40                  45

Gly Tyr Ile Ser Cys Tyr Asn Gly Phe Thr Ser Tyr Asn Pro Lys Phe
    50                  55                  60

Lys Gly Lys Ala Thr Phe Thr Val Asp Thr Ser Ser Thr Ala Tyr
65                  70                  75                  80

Ile Gln Phe Ser Arg Leu Thr Ser Glu Asp Ser Ala Val Tyr Tyr Cys
                85                  90                  95

Ala Arg Ser Asp Tyr Tyr Gly Thr Asn Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Gln Val Gln Leu Gln Gln Pro Gly Ala Glu Leu Val Arg
    130                 135                 140

Pro Gly Ala Ser Val Lys Leu Ser Cys Lys Ala Ser Gly Tyr Thr Phe
145                 150                 155                 160

Thr Thr Tyr Trp Met Asn Trp Val Lys Gln Arg Pro Gln Gln Gly Leu
                165                 170                 175

Glu Trp Ile Gly Arg Ile Asp Pro Tyr Asp Ser Glu Thr Leu Tyr Ser
            180                 185                 190
```

```
Gln Lys Phe Lys Asp Thr Ala Ile Leu Thr Val Asp Lys Ser Ser Ser
        195                 200                 205

Thr Ala Tyr Met Gln Leu Ser Ser Leu Thr Ser Glu Asp Ser Ala Val
        210                 215                 220

Tyr Tyr Cys Ala Arg Tyr Gly Phe Asp Tyr Trp Gly Gln Gly Thr Thr
225                 230                 235                 240

Leu Thr Val Ser Ser
                245

<210> SEQ ID NO 60
<211> LENGTH: 227
<212> TYPE: PRT
<213> ORGANISM: Artificial
<220> FEATURE:
<223> OTHER INFORMATION: Chimeric mouse/human VL region
<220> FEATURE:
<221> NAME/KEY: PEPTIDE
<222> LOCATION: (1)..(227)
<223> OTHER INFORMATION: DVD light varibale hIL-1a/b DVD6b-Ig region

<400> SEQUENCE: 60

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Ala Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Val Ser Arg Met Glu Ala Glu
65                  70                  75                  80

Asp Ala Ala Thr Tyr Tyr Cys Gln Gln Arg Ser Thr Tyr Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Gln Ile Val Leu Thr Gln Ser Pro Ala
        115                 120                 125

Leu Met Ser Ala Ser Pro Gly Glu Lys Val Thr Met Thr Cys Ser Ala
    130                 135                 140

Ser Ser Ser Val Asn Tyr Met Tyr Trp Tyr Gln Gln Lys Pro Arg Ser
145                 150                 155                 160

Ser Pro Lys Pro Trp Ile Tyr Leu Thr Ser Asn Leu Ala Ser Gly Val
                165                 170                 175

Pro Ala Arg Phe Ser Gly Ser Gly Ser Gly Thr Ser Tyr Ser Leu Thr
            180                 185                 190

Ile Ser Ser Met Glu Ala Glu Asp Ala Ala Thr Tyr Tyr Cys Gln Gln
        195                 200                 205

Trp Asn Ser Asn Pro Tyr Thr Phe Gly Gly Gly Thr Lys Leu Glu Met
    210                 215                 220

Lys Arg Arg
225

<210> SEQ ID NO 61
<211> LENGTH: 62
<212> TYPE: DNA
<213> ORGANISM: Artificial
<220> FEATURE:
<223> OTHER INFORMATION: PCR Primer
```

```
<220> FEATURE:
<221> NAME/KEY: primer
<222> LOCATION: (1)..(62)

<400> SEQUENCE: 61
tagagatccc tcgacctcga gatccattgt gcccgggcgc caccatggag tttgggctga    60
gc                                                                  62

<210> SEQ ID NO 62
<211> LENGTH: 45
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(45)

<400> SEQUENCE: 62
cacctctggg cccttggtcg acgctgaaga gacggtgacc attgt                    45

<210> SEQ ID NO 63
<211> LENGTH: 60
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(60)

<400> SEQUENCE: 63
gggtgccagg gggaagaccg atgggccctt ggtcgacgct gaagagacgg tgaccattgt    60

<210> SEQ ID NO 64
<211> LENGTH: 45
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(45)

<400> SEQUENCE: 64
tcttcagcgt cgaccaaggg cccagaggtg cagctggtgc agtct                    45

<210> SEQ ID NO 65
<211> LENGTH: 60
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(60)

<400> SEQUENCE: 65
gcgtcgacca agggcccatc ggtcttcccc ctggcacccg aggtgcagct ggtgcagtct    60

<210> SEQ ID NO 66
<211> LENGTH: 21
<212> TYPE: DNA
<213> ORGANISM: Artificial
<220> FEATURE:
<223> OTHER INFORMATION: PCR Primer
<220> FEATURE:
<221> NAME/KEY: primer
```

```
<222> LOCATION: (1)..(21)

<400> SEQUENCE: 66
gtagtccttg accaggcagc c                                              21

<210> SEQ ID NO 67
<211> LENGTH: 62
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(62)

<400> SEQUENCE: 67
tagagatccc tcgacctcga gatccattgt gcccgggcgc caccatgact tggacccac    60 tc                                                                   62

<210> SEQ ID NO 68
<211> LENGTH: 45
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(45)

<400> SEQUENCE: 68
tatttcgggg gcagccttgg gctgacctag tactgtgacc ttggt                    45

<210> SEQ ID NO 69
<211> LENGTH: 60
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(60)

<400> SEQUENCE: 69
gggcgggaac agagtgaccg aggggcagc cttgggctga cctagtactg tgaccttggt    60

<210> SEQ ID NO 70
<211> LENGTH: 45
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(45)

<400> SEQUENCE: 70
ctaggtcagc ccaaggctgc ccccgaaata gtgatgacgc agtct                    45

<210> SEQ ID NO 71
<211> LENGTH: 60
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(60)
```

<400> SEQUENCE: 71
cagcccaagg ctgcccctc ggtcactctg ttcccgcccg aaatagtgat gacgcagtct    60

<210> SEQ ID NO 72
<211> LENGTH: 59
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(59)

<400> SEQUENCE: 72
gtcccaggtg gggaccctca ctctagagtc gcggccgcct aacactctcc cctgttgaa     59

<210> SEQ ID NO 73
<211> LENGTH: 45
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(45)

<400> SEQUENCE: 73
cacctgtggg cccttggtcg acgctgaaga gacggtgacc attgt                    45

<210> SEQ ID NO 74
<211> LENGTH: 60
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(60)

<400> SEQUENCE: 74
gggtgccagg gggaagaccg atgggcccct ggtcgacgct gaagagacgg tgaccattgt    60

<210> SEQ ID NO 75
<211> LENGTH: 45
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(45)

<400> SEQUENCE: 75
tcttcagcgt cgaccaaggg cccacaggtg cagctggtgg agtct                    45

<210> SEQ ID NO 76
<211> LENGTH: 60
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(60)

<400> SEQUENCE: 76
gcgtcgacca agggcccatc ggtcttcccc ctggcacccc aggtgcagct ggtggagtct    60

<210> SEQ ID NO 77
<211> LENGTH: 65
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(65)

<400> SEQUENCE: 77
tagagatccc tcgacctcga gatccattgt gcccgggcgc caccatggaa gccccagcgc    60
agctt    65

<210> SEQ ID NO 78
<211> LENGTH: 42
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(42)

<400> SEQUENCE: 78
agactgtggt gcagccacag ttcgtttaat ctccagtcgt gt    42

<210> SEQ ID NO 79
<211> LENGTH: 57
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(57)

<400> SEQUENCE: 79
tggcgggaag atgaagacag atggtgcagc cacagttcgt ttaatctcca gtcgtgt    57

<210> SEQ ID NO 80
<211> LENGTH: 42
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(42)

<400> SEQUENCE: 80
aaacgaactg tggctgcacc acagtctgtg ctgactcagc cc    42

<210> SEQ ID NO 81
<211> LENGTH: 57
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(57)

<400> SEQUENCE: 81
actgtggctg caccatctgt cttcatcttc ccgccacagt ctgtgctgac tcagccc    57

<210> SEQ ID NO 82

```
<211> LENGTH: 59
<212> TYPE: DNA
<213> ORGANISM: Artificial
<220> FEATURE:
<223> OTHER INFORMATION: PCR Primer
<220> FEATURE:
<221> NAME/KEY: primer
<222> LOCATION: (1)..(59)

<400> SEQUENCE: 82
gtcccaggtg gggaccctca ctctagagtc gcggccgctc atgaacattc tgtaggggc      59

<210> SEQ ID NO 83
<211> LENGTH: 242
<212> TYPE: PRT
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(242)
<223> OTHER INFORMATION: DVD heavy variable DVD1218HC-SL region

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Ala Ser Thr Lys Gly Pro Glu Val Gln Leu Val Gln Ser
        115                 120                 125

Gly Thr Glu Val Lys Lys Pro Gly Glu Ser Leu Lys Ile Ser Cys Lys
    130                 135                 140

Gly Ser Gly Tyr Thr Val Thr Ser Tyr Trp Ile Gly Trp Val Arg Gln
145                 150                 155                 160

Met Pro Gly Lys Gly Leu Glu Trp Met Gly Phe Ile Tyr Pro Gly Asp
                165                 170                 175

Ser Glu Thr Arg Tyr Ser Pro Thr Phe Gln Gly Gln Val Thr Ile Ser
            180                 185                 190

Ala Asp Lys Ser Phe Asn Thr Ala Phe Leu Gln Trp Ser Ser Leu Lys
        195                 200                 205

Ala Ser Asp Thr Ala Met Tyr Tyr Cys Ala Arg Val Gly Ser Gly Trp
    210                 215                 220

Tyr Pro Tyr Thr Phe Asp Ile Trp Gly Gln Gly Thr Met Val Thr Val
225                 230                 235                 240

Ser Ser

<210> SEQ ID NO 84
<211> LENGTH: 115
<212> TYPE: PRT
<213> ORGANISM: Homo sapiens
```

```
<220> FEATURE:
<221> NAME/KEY: PEPTIDE
<222> LOCATION: (1)..(115)
<223> OTHER INFORMATION: Sequence of ABT-874 VH region

<400> SEQUENCE: 84

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 85
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Sequence of ABT-325 VH region

<400> SEQUENCE: 85

Glu Val Gln Leu Val Gln Ser Gly Thr Glu Val Lys Lys Pro Gly Glu
1               5                   10                  15

Ser Leu Lys Ile Ser Cys Lys Gly Ser Gly Tyr Thr Val Thr Ser Tyr
            20                  25                  30

Trp Ile Gly Trp Val Arg Gln Met Pro Gly Lys Gly Leu Glu Trp Met
        35                  40                  45

Gly Phe Ile Tyr Pro Gly Asp Ser Glu Thr Arg Tyr Ser Pro Thr Phe
    50                  55                  60

Gln Gly Gln Val Thr Ile Ser Ala Asp Lys Ser Phe Asn Thr Ala Phe
65                  70                  75                  80

Leu Gln Trp Ser Ser Leu Lys Ala Ser Asp Thr Ala Met Tyr Tyr Cys
                85                  90                  95

Ala Arg Val Gly Ser Gly Trp Tyr Pro Tyr Thr Phe Asp Ile Trp Gly
            100                 105                 110

Gln Gly Thr Met Val Thr Val Ser Ser
        115                 120

<210> SEQ ID NO 86
<211> LENGTH: 247
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(247)
<223> OTHER INFORMATION: DVD light variable DVD1218LC-SL region
```

```
<400> SEQUENCE: 86

Met Thr Trp Thr Pro Leu Leu Phe Leu Thr Leu Leu His Cys Thr
1               5                   10                  15

Gly Ser Leu Ser Gln Ser Val Leu Thr Gln Pro Pro Ser Val Ser Gly
            20                  25                  30

Ala Pro Gly Gln Arg Val Thr Ile Ser Cys Ser Gly Ser Arg Ser Asn
        35                  40                  45

Ile Gly Ser Asn Thr Val Lys Trp Tyr Gln Gln Leu Pro Gly Thr Ala
50                  55                  60

Pro Lys Leu Leu Ile Tyr Tyr Asn Asp Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
            100                 105                 110

Asp Arg Tyr Thr His Pro Ala Leu Leu Phe Gly Thr Gly Thr Lys Val
        115                 120                 125

Thr Val Leu Gly Gln Pro Lys Ala Ala Pro Glu Ile Val Met Thr Gln
130                 135                 140

Ser Pro Ala Thr Leu Ser Val Ser Pro Gly Glu Arg Ala Thr Leu Ser
145                 150                 155                 160

Cys Arg Ala Ser Glu Ser Ile Ser Ser Asn Leu Ala Trp Tyr Gln Gln
                165                 170                 175

Lys Pro Gly Gln Ala Pro Arg Leu Phe Ile Tyr Thr Ala Ser Thr Arg
            180                 185                 190

Ala Thr Asp Ile Pro Ala Arg Phe Ser Gly Ser Gly Ser Gly Thr Glu
        195                 200                 205

Phe Thr Leu Thr Ile Ser Ser Leu Gln Ser Glu Asp Phe Ala Val Tyr
210                 215                 220

Tyr Cys Gln Gln Tyr Asn Asn Trp Pro Ser Ile Thr Phe Gly Gln Gly
225                 230                 235                 240

Thr Arg Leu Glu Ile Lys Arg
                245

<210> SEQ ID NO 87
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: Sequence of ABT-874 VL region

<400> SEQUENCE: 87

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95
```

```
His Pro Ala Leu Leu Phe Gly Thr Gly Thr Lys Val Thr Val Leu Gly
            100                 105                 110

<210> SEQ ID NO 88
<211> LENGTH: 6
<212> TYPE: PRT
<213> ORGANISM: Artificial
<220> FEATURE:
<223> OTHER INFORMATION: linker region
<220> FEATURE:
<221> NAME/KEY: PEPTIDE
<222> LOCATION: (1)..(6)
<223> OTHER INFORMATION: Linker peptide

<400> SEQUENCE: 88

Gln Pro Lys Ala Ala Pro
1               5

<210> SEQ ID NO 89
<211> LENGTH: 109
<212> TYPE: PRT
<213> ORGANISM: Homo sapiens
<220> FEATURE:
<221> NAME/KEY: PEPTIDE
<222> LOCATION: (1)..(109)
<223> OTHER INFORMATION: Sequence of ABT-325 VL region

<400> SEQUENCE: 89

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Ile Ser Ser Asn
            20                  25                  30

Leu Ala Trp Tyr Gln Gln Lys Pro Gly Gln Ala Pro Arg Leu Phe Ile
        35                  40                  45

Tyr Thr Ala Ser Thr Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ser
                85                  90                  95

Ile Thr Phe Gly Gln Gly Thr Arg Leu Glu Ile Lys Arg
            100                 105

<210> SEQ ID NO 90
<211> LENGTH: 249
<212> TYPE: PRT
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(109)
<223> OTHER INFORMATION: DVD heavy variable DVD1218LC-LL region

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60
```

-continued

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Lys Thr His Gly Ser His Asp Asn Trp Gly Gln Gly Thr Met Val Thr
         100                 105                 110

Val Ser Ser Ala Ser Thr Lys Gly Pro Ser Val Phe Pro Leu Ala Pro
     115                 120                 125

Glu Val Gln Leu Val Gln Ser Gly Thr Glu Val Lys Lys Pro Gly Glu
 130                 135                 140

Ser Leu Lys Ile Ser Cys Lys Gly Ser Gly Tyr Thr Val Thr Ser Tyr
145                 150                 155                 160

Trp Ile Gly Trp Val Arg Gln Met Pro Gly Lys Gly Leu Glu Trp Met
                 165                 170                 175

Gly Phe Ile Tyr Pro Gly Asp Ser Glu Thr Arg Tyr Ser Pro Thr Phe
             180                 185                 190

Gln Gly Gln Val Thr Ile Ser Ala Asp Lys Ser Phe Asn Thr Ala Phe
         195                 200                 205

Leu Gln Trp Ser Ser Leu Lys Ala Ser Asp Thr Ala Met Tyr Tyr Cys
     210                 215                 220

Ala Arg Val Gly Ser Gly Trp Tyr Pro Tyr Thr Phe Asp Ile Trp Gly
225                 230                 235                 240

Gln Gly Thr Met Val Thr Val Ser Ser
                 245

<210> SEQ ID NO 91
<211> LENGTH: 234
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(234)
<223> OTHER INFORMATION: DVD light variable DVD1218LC-LL region

<400> SEQUENCE: 91

Gln Ser Val Leu Thr Gln Pro Pro Ser Val Ser Gly Ala Pro Gly Gln
  1               5                  10                  15

Arg Val Thr Ile Ser Cys Ser Gly Ser Arg Ser Asn Ile Gly Ser Asn
                 20                  25                  30

Thr Val Lys Trp Tyr Gln Gln Leu Pro Gly Thr Ala Pro Lys Leu Leu
             35                  40                  45

Ile Tyr Tyr Asn Asp Gln Arg Pro Ser Gly Val Pro Asp Arg Phe Ser
         50                  55                  60

Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Gln Ser Tyr Asp Arg Tyr Thr
             85                  90                  95

His Pro Ala Leu Leu Phe Gly Thr Gly Thr Lys Val Thr Val Leu Gly
         100                 105                 110

Gln Pro Lys Ala Ala Pro Ser Val Thr Leu Phe Pro Pro Glu Ile Val
     115                 120                 125

Met Thr Gln Ser Pro Ala Thr Leu Ser Val Ser Pro Gly Glu Arg Ala
 130                 135                 140

Thr Leu Ser Cys Arg Ala Ser Glu Ser Ile Ser Ser Asn Leu Ala Trp

```
                 145                 150                 155                 160
Tyr Gln Gln Lys Pro Gly Gln Ala Pro Arg Leu Phe Ile Tyr Thr Ala
                165                 170                 175

Ser Thr Arg Ala Thr Asp Ile Pro Ala Arg Phe Ser Gly Ser Gly Ser
            180                 185                 190

Gly Thr Glu Phe Thr Leu Thr Ile Ser Ser Leu Gln Ser Glu Asp Phe
        195                 200                 205

Ala Val Tyr Tyr Cys Gln Gln Tyr Asn Asn Trp Pro Ser Ile Thr Phe
    210                 215                 220

Gly Gln Gly Thr Arg Leu Glu Ile Lys Arg
225                 230

<210> SEQ ID NO 92
<211> LENGTH: 13
<212> TYPE: PRT
<213> ORGANISM: Artificial
<220> FEATURE:
<223> OTHER INFORMATION: linker region
<220> FEATURE:
<221> NAME/KEY: PEPTIDE
<222> LOCATION: (1)..(13)
<223> OTHER INFORMATION: Linker peptide

<400> SEQUENCE: 92

Gln Pro Lys Ala Ala Pro Ser Val Thr Leu Phe Pro Pro
1               5                   10

<210> SEQ ID NO 93
<211> LENGTH: 242
<212> TYPE: PRT
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(242)
<223> OTHER INFORMATION: DVD heavy variable DVD1812HC-SL region

<400> SEQUENCE: 93

Glu Val Gln Leu Val Gln Ser Gly Thr Glu Val Lys Lys Pro Gly Glu
1               5                   10                  15

Ser Leu Lys Ile Ser Cys Lys Gly Ser Gly Tyr Thr Val Thr Ser Tyr
            20                  25                  30

Trp Ile Gly Trp Val Arg Gln Met Pro Gly Lys Gly Leu Glu Trp Met
        35                  40                  45

Gly Phe Ile Tyr Pro Gly Asp Ser Glu Thr Arg Tyr Ser Pro Thr Phe
    50                  55                  60

Gln Gly Gln Val Thr Ile Ser Ala Asp Lys Ser Phe Asn Thr Ala Phe
65                  70                  75                  80

Leu Gln Trp Ser Ser Leu Lys Ala Ser Asp Thr Ala Met Tyr Tyr Cys
                85                  90                  95

Ala Arg Val Gly Ser Gly Trp Tyr Pro Tyr Thr Phe Asp Ile Trp Gly
            100                 105                 110

Gln Gly Thr Met Val Thr Val Ser Ser Ala Ser Thr Lys Gly Pro Gln
        115                 120                 125

Val Gln Leu Val Glu Ser Gly Gly Val Val Gln Pro Gly Arg Ser
    130                 135                 140

Leu Arg Leu Ser Cys Ala Ala Ser Gly Phe Thr Phe Ser Ser Tyr Gly
145                 150                 155                 160

Met His Trp Val Arg Gln Ala Pro Gly Lys Gly Leu Glu Trp Val Ala
```

```
                165                 170                 175
Phe Ile Arg Tyr Asp Gly Ser Asn Lys Tyr Tyr Ala Asp Ser Val Lys
            180                 185                 190

Gly Arg Phe Thr Ile Ser Arg Asp Asn Ser Lys Asn Thr Leu Tyr Leu
            195                 200                 205

Gln Met Asn Ser Leu Arg Ala Glu Asp Thr Ala Val Tyr Tyr Cys Lys
            210                 215                 220

Thr His Gly Ser His Asp Asn Trp Gly Gln Gly Thr Met Val Thr Val
225                 230                 235                 240

Ser Ser

<210> SEQ ID NO 94
<211> LENGTH: 226
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(226)
<223> OTHER INFORMATION: DVD light variable DVD1812LC-SL region

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Ile Ser Ser Asn
            20                  25                  30

Leu Ala Trp Tyr Gln Gln Lys Pro Gly Gln Ala Pro Arg Leu Phe Ile
        35                  40                  45

Tyr Thr Ala Ser Thr Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ser
                85                  90                  95

Ile Thr Phe Gly Gln Gly Thr Arg Leu Glu Ile Lys Arg Thr Val Ala
            100                 105                 110

Ala Pro Gln Ser Val Leu Thr Gln Pro Pro Ser Val Ser Gly Ala Pro
        115                 120                 125

Gly Gln Arg Val Thr Ile Ser Cys Ser Gly Ser Arg Ser Asn Ile Gly
    130                 135                 140

Ser Asn Thr Val Lys Trp Tyr Gln Gln Leu Pro Gly Thr Ala Pro Lys
145                 150                 155                 160

Leu Leu Ile Tyr Tyr Asn Asp Gln Arg Pro Ser Gly Val Pro Asp Arg
                165                 170                 175

Phe Ser Gly Ser Lys Ser Gly Thr Ser Ala Ser Leu Ala Ile Thr Gly
            180                 185                 190

Leu Gln Ala Glu Asp Glu Ala Asp Tyr Tyr Cys Gln Ser Tyr Asp Arg
        195                 200                 205

Tyr Thr His Pro Ala Leu Leu Phe Gly Thr Gly Thr Lys Val Thr Val
    210                 215                 220

Leu Gly
225

<210> SEQ ID NO 95
<211> LENGTH: 249
<212> TYPE: PRT
```

```
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(249)
<223> OTHER INFORMATION: DVD heavy variable DVD1812HC-LL region

<400> SEQUENCE: 95
```

Glu Val Gln Leu Val Gln Ser Gly Thr Glu Val Lys Lys Pro Gly Glu
1               5                   10                  15

Ser Leu Lys Ile Ser Cys Lys Gly Ser Gly Tyr Thr Val Thr Ser Tyr
            20                  25                  30

Trp Ile Gly Trp Val Arg Gln Met Pro Gly Lys Gly Leu Glu Trp Met
        35                  40                  45

Gly Phe Ile Tyr Pro Gly Asp Ser Glu Thr Arg Tyr Ser Pro Thr Phe
    50                  55                  60

Gln Gly Gln Val Thr Ile Ser Ala Asp Lys Ser Phe Asn Thr Ala Phe
65                  70                  75                  80

Leu Gln Trp Ser Ser Leu Lys Ala Ser Asp Thr Ala Met Tyr Tyr Cys
                85                  90                  95

Ala Arg Val Gly Ser Gly Trp Tyr Pro Tyr Thr Phe Asp Ile Trp Gly
            100                 105                 110

Gln Gly Thr Met Val Thr Val Ser Ala Ser Thr Lys Gly Pro Ser
        115                 120                 125

Val Phe Pro Leu Ala Pro Gln Val Gln Leu Val Glu Ser Gly Gly Gly
    130                 135                 140

Val Val Gln Pro Gly Arg Ser Leu Arg Leu Ser Cys Ala Ala Ser Gly
145                 150                 155                 160

Phe Thr Phe Ser Ser Tyr Gly Met His Trp Val Arg Gln Ala Pro Gly
                165                 170                 175

Lys Gly Leu Glu Trp Val Ala Phe Ile Arg Tyr Asp Gly Ser Asn Lys
            180                 185                 190

Tyr Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Lys Thr His Gly Ser His Asp Asn Trp Gly
225                 230                 235                 240

Gln Gly Thr Met Val Thr Val Ser Ser
                245

```
<210> SEQ ID NO 96
<211> LENGTH: 233
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(233)
<223> OTHER INFORMATION: DVD light variable DVD1812LC-LL region

<400> SEQUENCE: 96
```

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Ile Ser Ser Asn
            20                  25                  30

Leu Ala Trp Tyr Gln Gln Lys Pro Gly Gln Ala Pro Arg Leu Phe Ile

-continued

```
                35                  40                  45
Tyr Thr Ala Ser Thr Arg Ala Thr Asp Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Ser
                 85                  90                  95

Ile Thr Phe Gly Gln Gly Thr Arg Leu Glu Ile Lys Arg Thr Val Ala
                100                 105                 110

Ala Pro Ser Val Phe Ile Phe Pro Pro Gln Ser Val Leu Thr Gln Pro
                115                 120                 125

Pro Ser Val Ser Gly Ala Pro Gly Gln Arg Val Thr Ile Ser Cys Ser
130                 135                 140

Gly Ser Arg Ser Asn Ile Gly Ser Asn Thr Val Lys Trp Tyr Gln Gln
145                 150                 155                 160

Leu Pro Gly Thr Ala Pro Lys Leu Leu Ile Tyr Tyr Asn Asp Gln Arg
                165                 170                 175

Pro Ser Gly Val Pro Asp Arg Phe Ser Gly Ser Lys Ser Gly Thr Ser
                180                 185                 190

Ala Ser Leu Ala Ile Thr Gly Leu Gln Ala Glu Asp Glu Ala Asp Tyr
                195                 200                 205

Tyr Cys Gln Ser Tyr Asp Arg Tyr Thr His Pro Ala Leu Leu Phe Gly
210                 215                 220

Thr Gly Thr Lys Val Thr Val Leu Gly
225                 230
```

```
<210> SEQ ID NO 97
<211> LENGTH: 254
<212> TYPE: PRT
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(254)
<223> OTHER INFORMATION: DVD heavy variable CD20CD3DVD-Ig region

<400> SEQUENCE: 97
```

```
Gln Val Gln Leu Arg Gln Pro Gly Ala Glu Leu Val Lys Pro Gly Ala
 1                5                  10                  15

Ser Val Lys Met Ser Cys Lys Ala Ser Gly Tyr Thr Phe Thr Ser Tyr
                 20                  25                  30

Asn Met His Trp Val Lys Gln Thr Pro Gly Gln Gly Leu Glu Trp Ile
                 35                  40                  45

Gly Ala Ile Tyr Pro Gly Asn Gly Asp Thr Ser Tyr Asn Gln Lys Phe
 50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser His Tyr Gly Ser Asn Tyr Val Asp Tyr Phe Asp Tyr Trp
                100                 105                 110

Gly Gln Gly Thr Thr Leu Thr Val Ser Ser Ala Lys Thr Thr Ala Pro
                115                 120                 125

Ser Val Tyr Pro Leu Ala Pro Gln Val Gln Leu Gln Gln Ser Gly Ala
130                 135                 140
```

-continued

```
Glu Leu Ala Arg Pro Gly Ala Ser Val Lys Met Ser Cys Lys Ala Ser
145                 150                 155                 160

Gly Tyr Thr Phe Thr Arg Tyr Thr Met His Trp Val Lys Gln Arg Pro
                165                 170                 175

Gly Gln Gly Leu Glu Trp Ile Gly Tyr Ile Asn Pro Ser Arg Gly Tyr
            180                 185                 190

Thr Asn Tyr Asn Gln Lys Phe Lys Asp Lys Ala Thr Leu Thr Thr Asp
        195                 200                 205

Lys Ser Ser Ser Thr Ala Tyr Met Gln Leu Ser Ser Leu Thr Ser Glu
    210                 215                 220

Asp Ser Ala Val Tyr Tyr Cys Ala Arg Tyr Tyr Asp Asp His Tyr Cys
225                 230                 235                 240

Leu Asp Tyr Trp Gly Gln Gly Thr Thr Leu Thr Val Ser Ser
                245                 250

<210> SEQ ID NO 98
<211> LENGTH: 122
<212> TYPE: PRT
<213> ORGANISM: Homo sapiens
<220> FEATURE:
<221> NAME/KEY: PEPTIDE
<222> LOCATION: (1)..(122)
<223> OTHER INFORMATION: Sequence of 5F1 VH region

<400> SEQUENCE: 98

Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Thr Leu Thr Val Ser Ser
        115                 120

<210> SEQ ID NO 99
<211> LENGTH: 13
<212> TYPE: PRT
<213> ORGANISM: Artificial
<220> FEATURE:
<223> OTHER INFORMATION: linker region
<220> FEATURE:
<221> NAME/KEY: PEPTIDE
<222> LOCATION: (1)..(13)
<223> OTHER INFORMATION: Linker peptide

<400> SEQUENCE: 99

Ala Lys Thr Thr Ala Pro Ser Val Tyr Pro Leu Ala Pro
1               5                   10

<210> SEQ ID NO 100
<211> LENGTH: 119
<212> TYPE: PRT
<213> ORGANISM: Homo sapiens
```

```
<220> FEATURE:
<221> NAME/KEY: PEPTIDE
<222> LOCATION: (1)..(119)
<223> OTHER INFORMATION: Sequence of OKT3 VH region

<400> SEQUENCE: 100

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 101
<211> LENGTH: 226
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(226)
<223> OTHER INFORMATION: Sequence of CD20CD3DVD-Ig light variable region

<400> SEQUENCE: 101

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Gln Ile Val Leu Thr Gln Ser Pro Ala
        115                 120                 125

Ile Met Ser Ala Ser Pro Gly Glu Lys Val Thr Met Thr Cys Ser Ala
    130                 135                 140

Ser Ser Ser Val Ser Tyr Met Asn Trp Tyr Gln Gln Lys Ser Gly Thr
145                 150                 155                 160

Ser Pro Lys Arg Trp Ile Tyr Asp Thr Ser Lys Leu Ala Ser Gly Val
                165                 170                 175

Pro Ala His Phe Arg Gly Ser Gly Ser Gly Thr Ser Tyr Ser Leu Thr
```

```
                  180               185               190
Ile Ser Gly Met Glu Ala Glu Asp Ala Ala Thr Tyr Tyr Cys Gln Gln
            195               200               205

Trp Ser Ser Asn Pro Phe Thr Phe Gly Ser Gly Thr Lys Leu Glu Ile
    210               215               220

Asn Arg
225

<210> SEQ ID NO 102
<211> LENGTH: 107
<212> TYPE: PRT
<213> ORGANISM: Homo sapiens
<220> FEATURE:
<221> NAME/KEY: PEPTIDE
<222> LOCATION: (1)..(107)
<223> OTHER INFORMATION: Sequence of 5F1 VL region

<400> SEQUENCE: 102

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys Arg
            100                 105

<210> SEQ ID NO 103
<211> LENGTH: 12
<212> TYPE: PRT
<213> ORGANISM: Artificial
<220> FEATURE:
<223> OTHER INFORMATION: linker region
<220> FEATURE:
<221> NAME/KEY: PEPTIDE
<222> LOCATION: (1)..(12)
<223> OTHER INFORMATION: Linker peptide

<400> SEQUENCE: 103

Ala Asp Ala Ala Pro Thr Val Ser Ile Phe Pro Pro
1               5                   10

<210> SEQ ID NO 104
<211> LENGTH: 107
<212> TYPE: PRT
<213> ORGANISM: Homo sapiens
<220> FEATURE:
<221> NAME/KEY: PEPTIDE
<222> LOCATION: (1)..(107)
<223> OTHER INFORMATION: Sequence of OKT3 VL region

<400> SEQUENCE: 104

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30
```

```
Asn Trp Tyr Gln Gln Lys Ser Gly Thr Ser Pro Lys Arg Trp Ile Tyr
         35                  40                  45

Asp Thr Ser Lys Leu Ala Ser Gly Val Pro Ala His Phe Arg Gly Ser
     50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn Arg
                100                 105

<210> SEQ ID NO 105
<211> LENGTH: 249
<212> TYPE: PRT
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(243)
<223> OTHER INFORMATION: Sequence of mIL-1a/b DVD-Ig heavy variable
      region

<400> SEQUENCE: 105

Glu Val Gln Leu Gln Gln Ser Gly Pro Glu Leu Val Lys Pro Gly Thr
 1               5                  10                  15

Ser Val Lys Met Ser Cys Lys Thr Ser Gly Tyr Thr Phe Thr Ser Tyr
                 20                  25                  30

Val Met His Trp Val Lys Gln Lys Pro Gly Gln Gly Leu Glu Trp Ile
             35                  40                  45

Gly Tyr Ile Ile Pro Tyr Asn Asp Asn Thr Lys Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Arg Asn Glu Tyr Tyr Gly Ser Ser Phe Phe Asp Tyr Trp Gly
                100                 105                 110

Gln Gly Thr Thr Leu Thr Val Ser Ser Ala Lys Thr Thr Ala Pro Ser
            115                 120                 125

Val Tyr Pro Leu Ala Pro Gln Val Ile Leu Lys Glu Ser Gly Pro Gly
        130                 135                 140

Ile Leu Gln Pro Ser Gln Thr Leu Ser Leu Thr Cys Ser Phe Ser Gly
145                 150                 155                 160

Phe Ser Leu Ser Thr Tyr Gly Thr Ala Val Asn Trp Ile Arg Gln Pro
                165                 170                 175

Ser Gly Lys Gly Leu Glu Trp Leu Ala Gln Ile Gly Ser Asp Asp Arg
            180                 185                 190

Lys Leu Tyr Asn Pro Phe Leu Lys Ser Arg Ile Thr Leu Ser Glu Asp
        195                 200                 205

Thr Ser Asn Ser Gln Val Phe Leu Lys Ile Thr Ser Val Asp Thr Glu
    210                 215                 220

Asp Ser Ala Thr Tyr Tyr Cys Ala Asn Gly Val Met Glu Tyr Trp Gly
225                 230                 235                 240

Leu Gly Thr Ser Val Thr Val Ser Ser
                245
```

-continued

```
<210> SEQ ID NO 106
<211> LENGTH: 121
<212> TYPE: PRT
<213> ORGANISM: Homo sapiens
<220> FEATURE:
<221> NAME/KEY: PEPTIDE
<222> LOCATION: (1)..(121)
<223> OTHER INFORMATION: Sequence of 10G11 VH region

<400> SEQUENCE: 106

Glu Val Gln Leu Gln Gln Ser Gly Pro Glu Leu Val Lys Pro Gly Thr
 1               5                  10                  15

Ser Val Lys Met Ser Cys Lys Thr Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Asn Thr Lys Tyr Asn Glu Lys Phe
    50                  55                  60

Lys Gly Lys Ala Thr Leu Thr Ser Asp Lys Ser Ser Thr Ala Tyr
 65                 70                  75                  80

Met Glu Leu Ser Ser Leu Thr Ser Glu Asp Ser Ala Val Tyr Tyr Cys
                85                  90                  95

Ala Arg Arg Asn Glu Tyr Tyr Gly Ser Ser Phe Phe Asp Tyr Trp Gly
            100                 105                 110

Gln Gly Thr Thr Leu Thr Val Ser Ser
        115                 120

<210> SEQ ID NO 107
<211> LENGTH: 115
<212> TYPE: PRT
<213> ORGANISM: Homo sapiens
<220> FEATURE:
<221> NAME/KEY: PEPTIDE
<222> LOCATION: (1)..(115)
<223> OTHER INFORMATION: Sequence of 9H10 VH region

<400> SEQUENCE: 107

Gln Val Ile Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Tyr
            20                  25                  30

Gly Thr Ala Val Asn Trp Ile Arg Gln Pro Ser Gly Lys Gly Leu Glu
        35                  40                  45

Trp Leu Ala Gln Ile Gly Ser Asp Asp Arg Lys Leu Tyr Asn Pro Phe
    50                  55                  60

Leu Lys Ser Arg Ile Thr Leu Ser Glu Asp Thr Ser Asn Ser Gln Val
 65                 70                  75                  80

Phe Leu Lys Ile Thr Ser Val Asp Thr Glu Asp Ser Ala Thr Tyr Tyr
                85                  90                  95

Cys Ala Asn Gly Val Met Glu Tyr Trp Gly Leu Gly Thr Ser Val Thr
            100                 105                 110

Val Ser Ser
        115

<210> SEQ ID NO 108
<211> LENGTH: 330
<212> TYPE: PRT
<213> ORGANISM: Mouse
<220> FEATURE:
<221> NAME/KEY: PEPTIDE
<222> LOCATION: (1)..(320)
```

<223> OTHER INFORMATION: Sequence of CH region

<400> SEQUENCE: 108

| | | | | | | | | | | | | | | | |
|---|---|---|---|---|---|---|---|---|---|---|---|---|---|---|---|
| Ala | Lys | Thr | Thr | Ala | Pro | Ser | Val | Tyr | Pro | Leu | Ala | Pro | Val | Cys | Gly |
| 1 | | | | 5 | | | | | 10 | | | | | 15 | |
| Asp | Thr | Thr | Gly | Ser | Ser | Val | Thr | Leu | Gly | Cys | Leu | Val | Lys | Gly | Tyr |
| | | | 20 | | | | | 25 | | | | | 30 | | |
| Phe | Pro | Glu | Pro | Val | Thr | Leu | Thr | Trp | Asn | Ser | Gly | Ser | Leu | Ser | Ser |
| | | | | 35 | | | | | 40 | | | | | 45 | |
| Gly | Val | His | Thr | Phe | Pro | Ala | Val | Leu | Gln | Ser | Asp | Leu | Tyr | Thr | Leu |
| | | 50 | | | | | 55 | | | | | 60 | | | |
| Ser | Ser | Ser | Val | Thr | Val | Thr | Ser | Ser | Thr | Trp | Pro | Ser | Gln | Ser | Ile |
| 65 | | | | | 70 | | | | | 75 | | | | | 80 |
| Thr | Cys | Asn | Val | Ala | His | Pro | Ala | Ser | Ser | Thr | Lys | Val | Asp | Lys | Lys |
| | | | | 85 | | | | | 90 | | | | | 95 | |
| Ile | Glu | Pro | Arg | Gly | Pro | Thr | Ile | Lys | Pro | Cys | Pro | Pro | Cys | Lys | Cys |
| | | | 100 | | | | | 105 | | | | | 110 | | |
| Pro | Ala | Pro | Asn | Leu | Leu | Gly | Gly | Pro | Ser | Val | Phe | Ile | Phe | Pro | Pro |
| | | 115 | | | | | 120 | | | | | 125 | | | |
| Lys | Ile | Lys | Asp | Val | Leu | Met | Ile | Ser | Leu | Ser | Pro | Ile | Val | Thr | Cys |
| | 130 | | | | | 135 | | | | | 140 | | | | |
| Val | Val | Val | Asp | Val | Ser | Glu | Asp | Asp | Pro | Asp | Val | Gln | Ile | Ser | Trp |
| 145 | | | | | 150 | | | | | 155 | | | | | 160 |
| Phe | Val | Asn | Asn | Val | Glu | Val | His | Thr | Ala | Gln | Thr | Gln | Thr | His | Arg |
| | | | | 165 | | | | | 170 | | | | | 175 | |
| Glu | Asp | Tyr | Asn | Ser | Thr | Leu | Arg | Val | Val | Ser | Ala | Leu | Pro | Ile | Gln |
| | | | 180 | | | | | 185 | | | | | 190 | | |
| His | Gln | Asp | Trp | Met | Ser | Gly | Lys | Glu | Phe | Lys | Cys | Lys | Val | Asn | Asn |
| | | | | 195 | | | | | 200 | | | | | 205 | |
| Lys | Asp | Leu | Pro | Ala | Pro | Ile | Glu | Arg | Thr | Ile | Ser | Lys | Pro | Lys | Gly |
| | | 210 | | | | | 215 | | | | | 220 | | | |
| Ser | Val | Arg | Ala | Pro | Gln | Val | Tyr | Val | Leu | Pro | Pro | Pro | Glu | Glu | Glu |
| 225 | | | | | 230 | | | | | 235 | | | | | 240 |
| Met | Thr | Lys | Lys | Gln | Val | Thr | Leu | Thr | Cys | Met | Val | Thr | Asp | Phe | Met |
| | | | | 245 | | | | | 250 | | | | | 255 | |
| Pro | Glu | Asp | Ile | Tyr | Val | Glu | Trp | Thr | Asn | Asn | Gly | Lys | Thr | Glu | Leu |
| | | | 260 | | | | | 265 | | | | | 270 | | |
| Asn | Tyr | Lys | Asn | Thr | Glu | Pro | Val | Leu | Asp | Ser | Asp | Gly | Ser | Tyr | Phe |
| | | | | 275 | | | | | 280 | | | | | 285 | |
| Met | Tyr | Ser | Lys | Leu | Arg | Val | Glu | Lys | Lys | Asn | Trp | Val | Glu | Arg | Asn |
| | | 290 | | | | | 295 | | | | | 300 | | | |
| Ser | Tyr | Ser | Cys | Ser | Val | Val | His | Glu | Gly | Leu | His | Asn | His | His | Thr |
| 305 | | | | | 310 | | | | | 315 | | | | | 320 |
| Thr | Lys | Ser | Phe | Ser | Arg | Thr | Pro | Gly | Lys | | | | | | |
| | | | | 325 | | | | | 330 | | | | | | |

<210> SEQ ID NO 109
<211> LENGTH: 228
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(228)
<223> OTHER INFORMATION: Sequence of mIL-1a/b DVD-Ig light variable
    region

```
<400> SEQUENCE: 109

Asp Ile Gln Met Thr Gln Ser Pro Ala Ser Leu Ser Ala Ser Val Gly
 1               5                  10                  15

Glu Thr Val Thr Ile Thr Cys Arg Gly Ser Gly Ile Leu His Asn Tyr
             20                  25                  30

Leu Val Trp Tyr Gln Gln Lys Gln Gly Lys Ser Pro Gln Leu Leu Val
         35                  40                  45

Tyr Ser Ala Lys Ile Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Phe
                 85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ile Val Met Thr Gln Thr Pro
            115                 120                 125

Lys Phe Leu Leu Val Ser Ala Gly Asp Arg Val Thr Ile Thr Cys Lys
        130                 135                 140

Ala Ser Gln Ser Val Asn His Asp Val Ala Trp Tyr Gln Gln Met Pro
145                 150                 155                 160

Gly Gln Ser Pro Lys Leu Leu Ile Tyr Phe Ala Ser Asn Arg Tyr Thr
                165                 170                 175

Gly Val Pro Asp Arg Phe Thr Gly Ser Gly Tyr Gly Thr Asp Phe Thr
            180                 185                 190

Phe Thr Ile Ser Thr Val Gln Ala Glu Asp Leu Ala Val Tyr Phe Cys
        195                 200                 205

Gln Gln Asp Tyr Ser Ser Pro Tyr Thr Phe Gly Gly Gly Thr Lys Leu
    210                 215                 220

Glu Ile Lys Arg
225

<210> SEQ ID NO 110
<211> LENGTH: 108
<212> TYPE: PRT
<213> ORGANISM: Homo sapiens
<220> FEATURE:
<221> NAME/KEY: PEPTIDE
<222> LOCATION: (1)..(108)
<223> OTHER INFORMATION: Sequence of 10G11 VL region

<400> SEQUENCE: 110

Asp Ile Gln Met Thr Gln Ser Pro Ala Ser Leu Ser Ala Ser Val Gly
 1               5                  10                  15

Glu Thr Val Thr Ile Thr Cys Arg Gly Ser Gly Ile Leu His Asn Tyr
             20                  25                  30

Leu Val Trp Tyr Gln Gln Lys Gln Gly Lys Ser Pro Gln Leu Leu Val
         35                  40                  45

Tyr Ser Ala Lys Ile Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Phe
                 85                  90                  95

Thr Phe Gly Ser Gly Thr Lys Leu Glu Ile Lys Arg
```

<210> SEQ ID NO 111
<211> LENGTH: 12
<212> TYPE: PRT
<213> ORGANISM: Artificial
<220> FEATURE:
<223> OTHER INFORMATION: linker region
<220> FEATURE:
<221> NAME/KEY: PEPTIDE
<222> LOCATION: (1)..(12)
<223> OTHER INFORMATION: Linker peptide

<400> SEQUENCE: 111

```
Ala Asp Ala Ala Pro Thr Val Ser Ile Phe Pro Pro
 1               5                  10
```

<210> SEQ ID NO 112
<211> LENGTH: 108
<212> TYPE: PRT
<213> ORGANISM: Homo sapiens
<220> FEATURE:
<221> NAME/KEY: PEPTIDE
<222> LOCATION: (1)..(108)
<223> OTHER INFORMATION: Sequence of 9H10 VL region

<400> SEQUENCE: 112

```
Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Asn His Asp
            20                  25                  30

Val Ala Trp Tyr Gln Gln Met Pro Gly Gln Ser Pro Lys Leu Leu Ile
        35                  40                  45

Tyr Phe Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg
            100                 105
```

<210> SEQ ID NO 113
<211> LENGTH: 106
<212> TYPE: PRT
<213> ORGANISM: Mouse
<220> FEATURE:
<221> NAME/KEY: PEPTIDE
<222> LOCATION: (1)..(106)
<223> OTHER INFORMATION: Sequence of CL region

<400> SEQUENCE: 113

```
Ala Asp Ala Ala Pro Thr Val Ser Ile Phe Pro Pro Ser Ser Glu Gln
 1               5                  10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80
```

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 114
<211> LENGTH: 246
<212> TYPE: PRT
<213> ORGANISM: Artificial
<220> FEATURE:
<223> OTHER INFORMATION: antibody VH region
<220> FEATURE:
<221> NAME/KEY: PEPTIDE
<222> LOCATION: (1)..(246)
<223> OTHER INFORMATION: Sequence of 1D4.1-ABT325 DVD-Ig heavy variable
      region

<400> SEQUENCE: 114

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly Ile Arg Ser Ala Met Asp Tyr Trp Gly Gln Gly
            100                 105                 110

Thr Thr Val Thr Val Ser Ser Ala Ser Thr Lys Gly Pro Glu Val Gln
        115                 120                 125

Leu Val Gln Ser Gly Thr Glu Val Lys Lys Pro Gly Glu Ser Leu Lys
    130                 135                 140

Ile Ser Cys Lys Gly Ser Gly Tyr Thr Val Thr Ser Tyr Trp Ile Gly
145                 150                 155                 160

Trp Val Arg Gln Met Pro Gly Lys Gly Leu Glu Trp Met Gly Phe Ile
                165                 170                 175

Tyr Pro Gly Asp Ser Glu Thr Arg Tyr Ser Pro Thr Phe Gln Gly Gln
            180                 185                 190

Val Thr Ile Ser Ala Asp Lys Ser Phe Asn Thr Ala Phe Leu Gln Trp
        195                 200                 205

Ser Ser Leu Lys Ala Ser Asp Thr Ala Met Tyr Tyr Cys Ala Arg Val
    210                 215                 220

Gly Ser Gly Trp Tyr Pro Tyr Thr Phe Asp Ile Trp Gly Gln Gly Thr
225                 230                 235                 240

Met Val Thr Val Ser Ser
                245

<210> SEQ ID NO 115
<211> LENGTH: 119
<212> TYPE: PRT
<213> ORGANISM: Homo sapiens
<220> FEATURE:
<221> NAME/KEY: PEPTIDE
<222> LOCATION: (1)..(119)
<223> OTHER INFORMATION: Sequence of 1D4.1 VH region

```
<400> SEQUENCE: 115

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly Ile Arg Ser Ala Met Asp Tyr Trp Gly Gln Gly
            100                 105                 110

Thr Thr Val Thr Val Ser Ser
            115

<210> SEQ ID NO 116
<211> LENGTH: 222
<212> TYPE: PRT
<213> ORGANISM: Artificial
<220> FEATURE:
<223> OTHER INFORMATION: antibody VL region
<220> FEATURE:
<221> NAME/KEY: PEPTIDE
<222> LOCATION: (1)..(222)
<223> OTHER INFORMATION: Sequence of 1D4.1-ABT325 DVD-Ig light variable
      region

<400> SEQUENCE: 116

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg Thr Val Ala Ala
            100                 105                 110

Pro Glu Ile Val Met Thr Gln Ser Pro Ala Thr Leu Ser Val Ser Pro
            115                 120                 125

Gly Glu Arg Ala Thr Leu Ser Cys Arg Ala Ser Glu Ser Ile Ser Ser
        130                 135                 140

Asn Leu Ala Trp Tyr Gln Gln Lys Pro Gly Gln Ala Pro Arg Leu Phe
145                 150                 155                 160

Ile Tyr Thr Ala Ser Thr Arg Ala Thr Asp Ile Pro Ala Arg Phe Ser
                165                 170                 175

Gly Ser Gly Ser Gly Thr Glu Phe Thr Leu Thr Ile Ser Ser Leu Gln
            180                 185                 190

Ser Glu Asp Phe Ala Val Tyr Tyr Cys Gln Gln Tyr Asn Asn Trp Pro
        195                 200                 205
```

```
Ser Ile Thr Phe Gly Gln Gly Thr Arg Leu Glu Ile Lys Arg
    210                 215                 220
```

<210> SEQ ID NO 117
<211> LENGTH: 108
<212> TYPE: PRT
<213> ORGANISM: Homo sapiens
<220> FEATURE:
<221> NAME/KEY: PEPTIDE
<222> LOCATION: (1)..(108)
<223> OTHER INFORMATION: Sequence of 1D4.1 VL region

<400> SEQUENCE: 117

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105
```